US010822354B2

(12) United States Patent
Yamasaki et al.

(10) Patent No.: US 10,822,354 B2
(45) Date of Patent: Nov. 3, 2020

(54) METHOD FOR PRODUCING 7H-PYRROLO[2, 3-D]PYRIMIDINE DERIVATIVE AND INTERMEDIATE THEREOF

(71) Applicant: JAPAN TOBACCO INC., Tokyo (JP)

(72) Inventors: Takahiro Yamasaki, Osaka (JP); Yoshinori Hara, Osaka (JP); Takayuki Sakai, Osaka (JP); Kengo Murakami, Osaka (JP); Katsuyoshi Hara, Osaka (JP); Naoki Manta, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 15/741,926

(22) PCT Filed: Jul. 6, 2016

(86) PCT No.: PCT/JP2016/070046
§ 371 (c)(1),
(2) Date: Nov. 5, 2018

(87) PCT Pub. No.: WO2017/006968
PCT Pub. Date: Jan. 12, 2017

(65) Prior Publication Data
US 2019/0062346 A1 Feb. 28, 2019

(30) Foreign Application Priority Data

Jul. 7, 2015 (JP) .................................. 2015-136196

(51) Int. Cl.
| | |
|---|---|
| C07D 205/04 | (2006.01) |
| C07D 519/00 | (2006.01) |
| C07D 487/10 | (2006.01) |
| A61K 31/519 | (2006.01) |
| C07B 61/00 | (2006.01) |

(52) U.S. Cl.
CPC ......... C07D 519/00 (2013.01); C07D 205/04 (2013.01); C07D 487/10 (2013.01); *A61K 31/519* (2013.01); *C07B 61/00* (2013.01); *C07B 2200/13* (2013.01); *Y02P 20/55* (2015.11)

(58) Field of Classification Search
CPC .......................... C07B 2200/13; C07D 205/04
See application file for complete search history.

(56) References Cited

U.S. PATENT DOCUMENTS

| 8,609,647 B2 | 12/2013 | Noji et al. |
| 2006/0128789 A1 | 6/2006 | Chand et al. |
| 2008/0076753 A1 | 3/2008 | Xiang et al. |
| 2011/0136778 A1 | 6/2011 | Satoru et al. |
| 2014/0256702 A1 | 9/2014 | Fenster et al. |
| 2019/0062346 A1 | 2/2019 | Yamasaki et al. |

FOREIGN PATENT DOCUMENTS

| CN | 103570601 | 2/2014 |
| EP | 3321271 | 5/2018 |
| JP | 2010504351 | 2/2010 |
| JP | 2016512195 | 4/2016 |
| WO | WO 2008/036755 | 3/2008 |
| WO | WO 2011/013785 | 2/2011 |
| WO | WO2012/098033 | 7/2012 |
| WO | WO2014/138053 | 9/2014 |
| WO | WO 2017/006968 | 1/2017 |
| WO | WO 2018/117152 | 6/2018 |

OTHER PUBLICATIONS

Bhattacharya et al. (Brittain, ed. Polymorphism in Pharmaceutical Solids, 2009, p. 334.*
EPO Partial Supplementary European Search Report in European Application No. 16821437.7, dated Jan. 31, 2019, 11 pages.
Perez-Faginas et al., "Synthesis and SAR studies on azetidine-containing dipeptides as HCMV inhibitors", Bioorganic & Medicinal Chemistry, 2011, pp. 1155-1161.
Bańkowski et al., "Synthesis, biological activity and resistance to proteolytic digestion of new cyclic dermorphin/deltorphin analogues," European Journal of Medicinal Chemistry, (2013), 63:457-467.
Berge, et al., "Pharmaceutical Salts," Journal of Pharmaceutical Sciences, Jan. 1977, 66(1):1-19.
Drouillat et al., "Insight into the Regioselectivity of Nucleophilic Ring-Opening of Azetidinium Ions Containing Quaternary Carbon Atoms," European Journal of Organic Chemistry, (2012), 2012(30):6005-6012.
Hirayama et al., Handbook of Organic Compound Crystal Production, 2008, pp. 10, 11, 57-72 and 78-81 (English Summary).
International Search Report in International Application No. PCT/JP2016/070046, dated Sep. 27, 2016, 2 pages (English Translation).
International Search Report in International Application No. PCT/JP2017/045729, dated Mar. 20, 2018, 5 pages (English Translation).
Kawabata et al., "Stereochemical Diversity in Asymmetric Cyclization via Memory of Chirality," Journal of the American Chemical Society, Nov. 9, 2006, 128(48):15394-15395.
Kunz et al., "Formation of 4-, 5- and 6-membered heterocycles by ambidoselective cyclization of enolate anions," Helvetica Chimica Acta, (1979), 62(3):872-881 (with English Abstract).

(Continued)

*Primary Examiner* — Susanna Moore

(74) *Attorney, Agent, or Firm* — Fish & Richardson P.C.

(57) ABSTRACT

The present invention provides a method for producing a 7H-pyrrolo[2,3-d]pyrimidine derivative that is useful as a janus kinase (JAK) inhibitor; an intermediate of the 7H-pyrrolo[2,3-d]pyrimidine derivative; and a method for producing the intermediate. The present invention provides a method for producing 3-[(3S,4R)-3-methyl-6-(7H-pyrrolo[2,3-d]pyrimidin-4-yl)-1,6-diazaspiro[3.4]octan-1-yl]-3-oxopropanenitrile, which uses a salt of an organic acid and (3S,4R)-3-methyl-1,6-diazaspiro[3.4]octane-1-carboxylic acid benzyl.

6 Claims, 4 Drawing Sheets

(56) References Cited

OTHER PUBLICATIONS

Loh et al., "A remote substituent as a control element in indium-mediated allylation reactions in aqueous media: highly diastereoselective synthesis of 1,3-amino alcohols," Tetrahedron Letters, (2000), 41:6511-6515.

Majer et al., "Synthesis and Absolute Configuration of 1,7-diazaspiro[4,4]nonane-2,6-dione," Collection of Czechoslovak Chemical Communications, (1982), 47(3):950-960.

Núñez-Villanueva et al., "Quaternary α,α-2-Oxoazepane α-Amino Acids: Synthesis from Ornithine-Derived β-Lactams and Incorporation into Model Dipeptides," Journal of Organic Chemistry, (2011), 76:6592-6603.

Van Nispen et al., "Synthesis and Biological Activities of Two ACTH-Analogues Containing L-Norarginine in Position 8," International Journal of Peptide and Protein Research, (1977), 9(3):193-202.

Written Opinion in International Application No. PCT/JP2016/070046, dated Sep. 27, 2016, 7 pages (English Translation).

Written Opinion in International Application No. PCT/JP2017/045729, dated Mar. 20, 2018, 7 pages (Machine Translation).

U.S. Appl. No. 16/470,888, filed Jun. 18, 2019, Takiguchi.

Bhattacharya et al., "Polymorphism in Pharmaceutical Solids", Drugs and the Pharmaceutical Sciences, Second Edition, 2009, 192:334.

English translation of International Preliminary Report on Patentability in International Application No. PCT/JP2017/045729 dated Mar. 20, 2018.

Stacy et al., "Synthesis and biological evaluation of triazole-containng N-acyl homoserine lactones as quorum sensing modulators", Org. Biomol. Chem., Feb. 2013, 11(6):938-954.

* cited by examiner

[Figure 1]
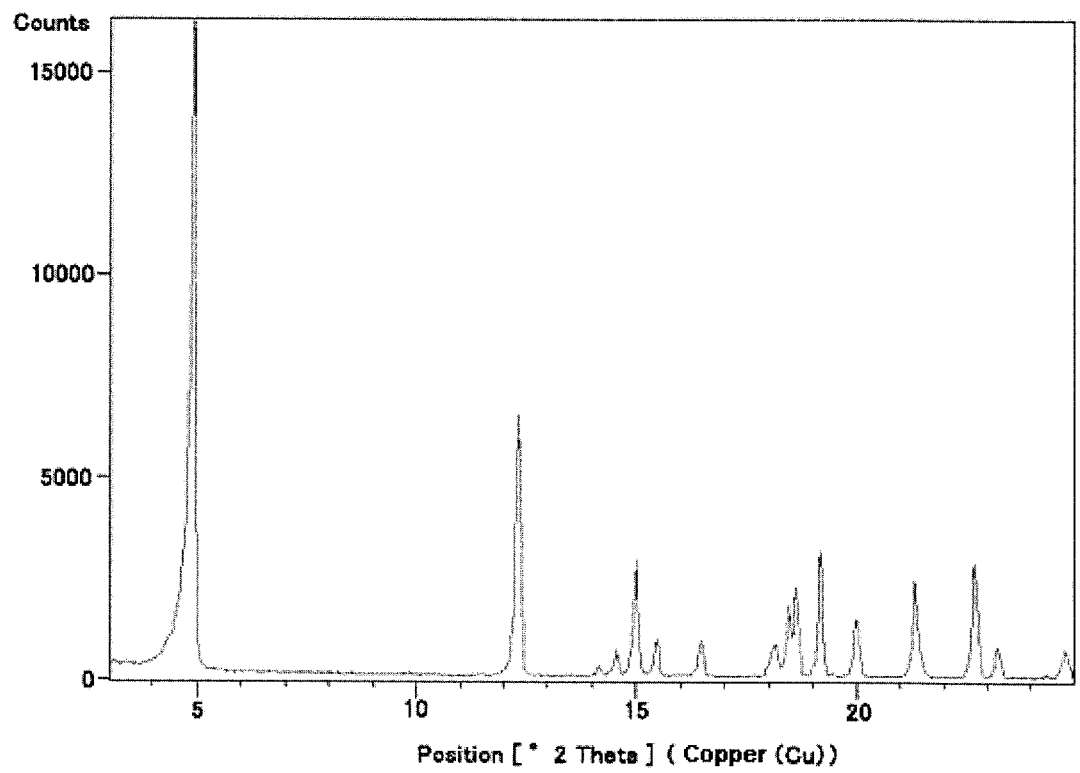
[Figure 2]
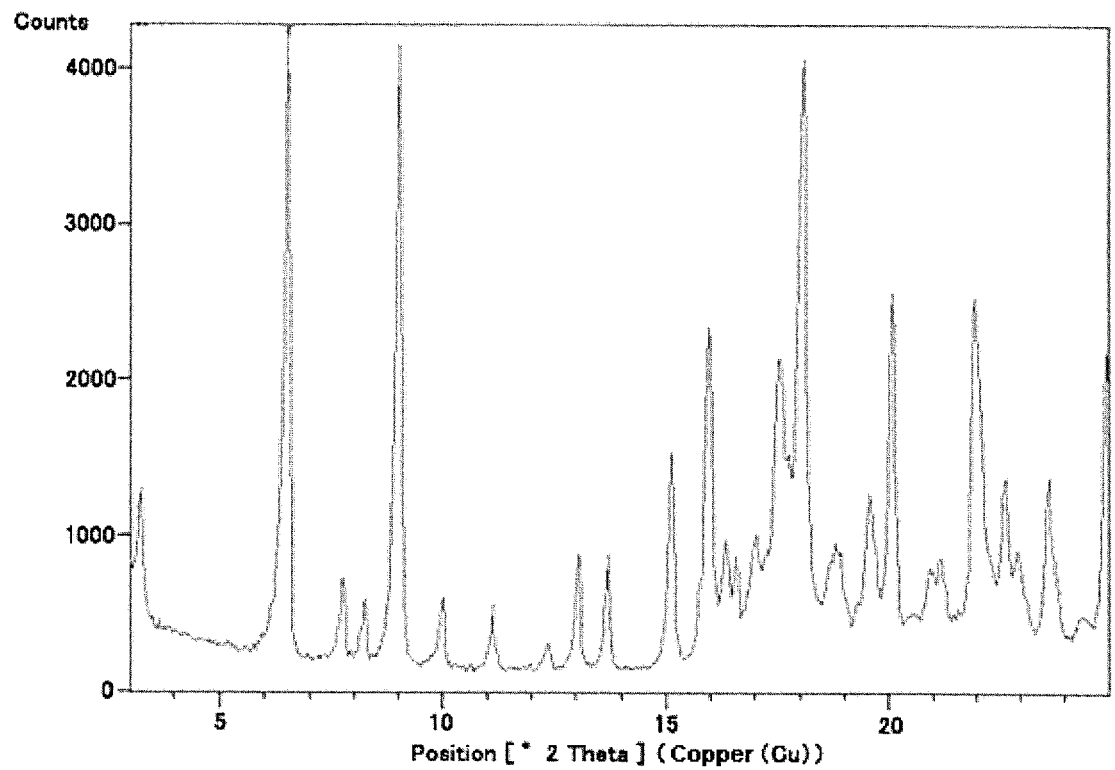

[Figure 3]
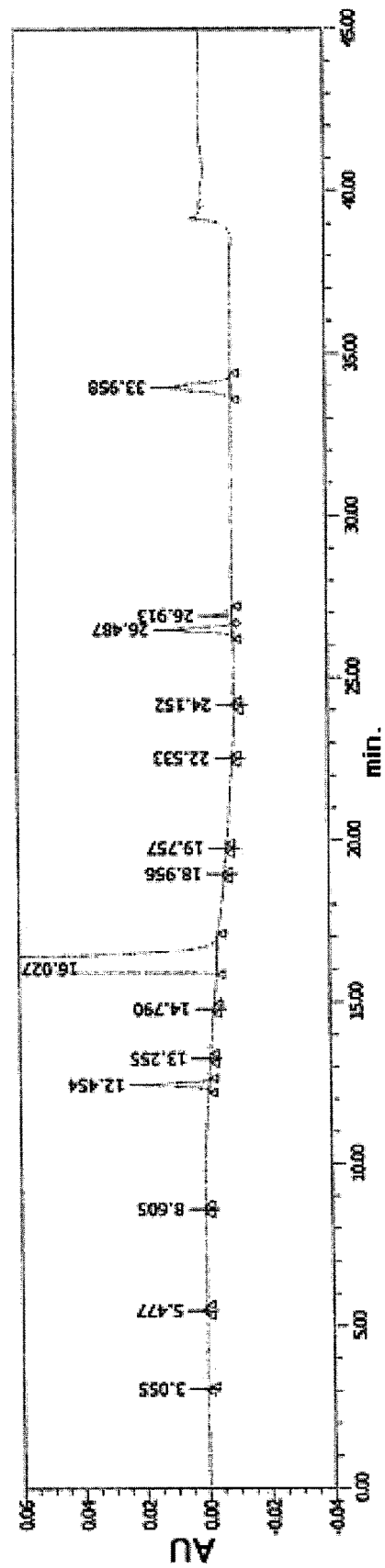

[Figure 4]
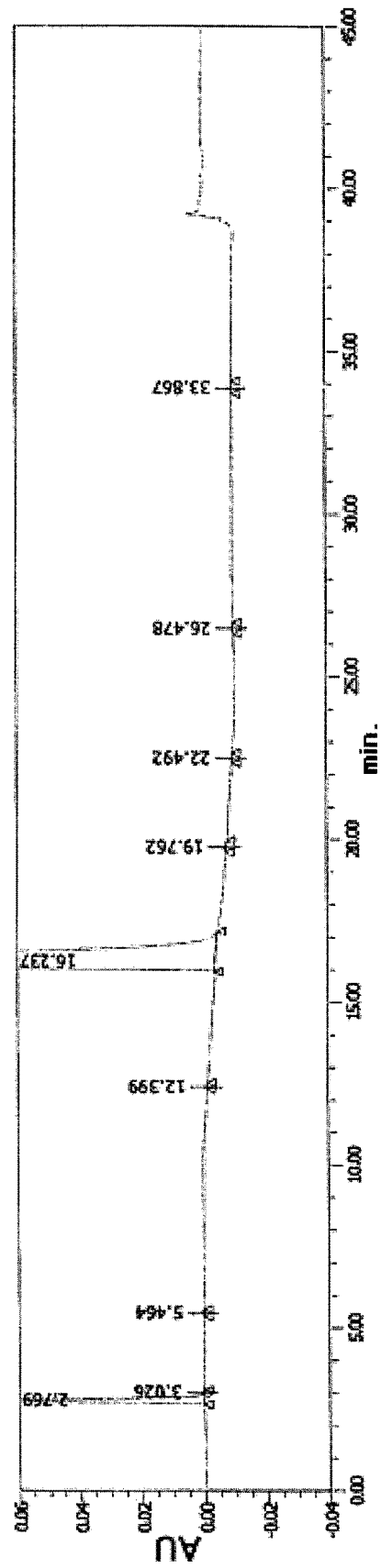

[Figure 5]
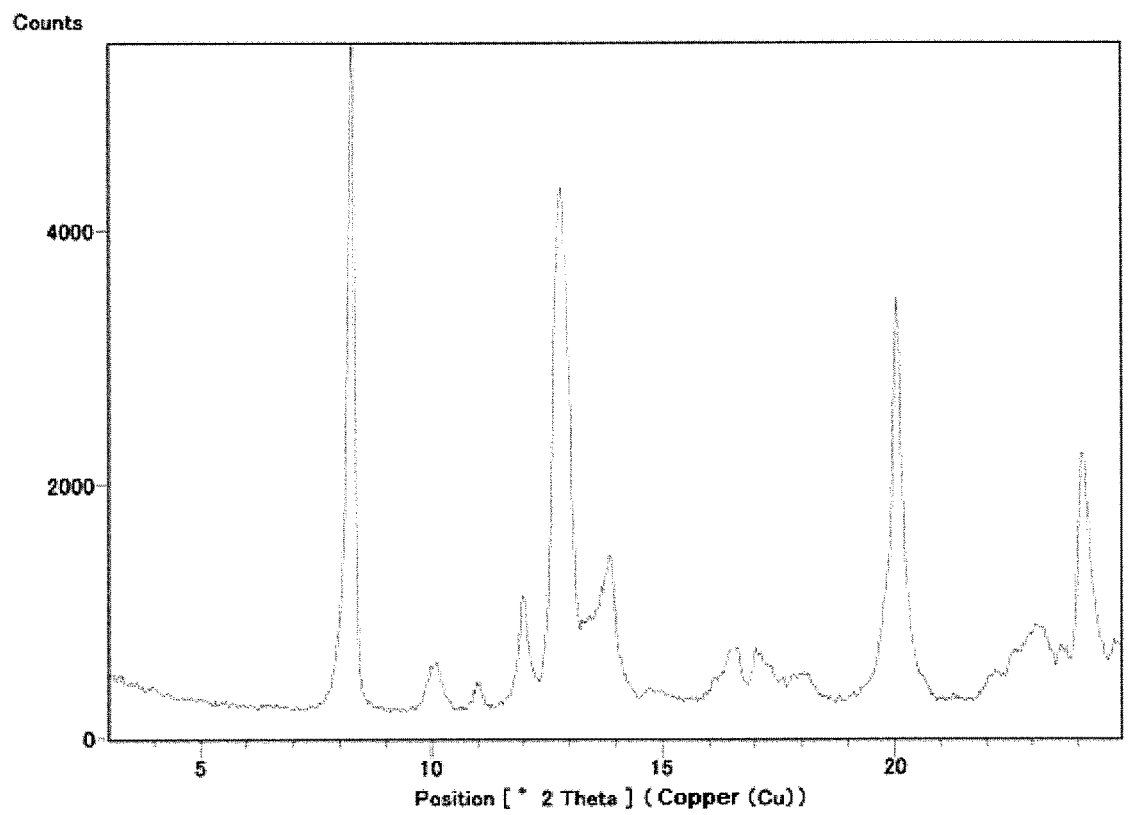
[Figure 6]
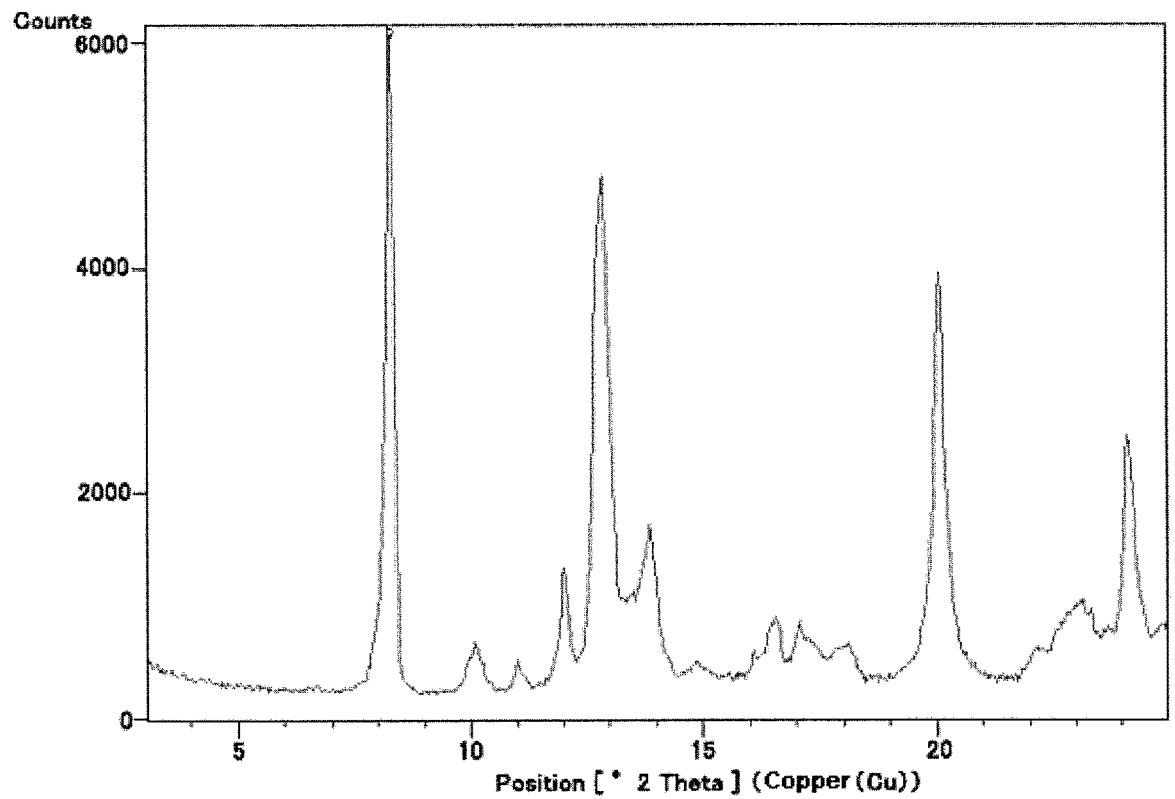

METHOD FOR PRODUCING 7H-PYRROLO[2,3-D]PYRIMIDINE DERIVATIVE AND INTERMEDIATE THEREOF

CROSS-REFERENCE TO RELATED APPLICATIONS

This application is the U.S. National Stage of International Application No. PCT/JP2016/070046, filed on Jul. 6, 2016, which claims the benefit of Japanese Application No. 2015-136196, filed on Jul. 7, 2015. The contents of each of these applications are incorporated herein by reference in their entirety.

TECHNICAL FIELD

The present invention relates to process for preparing 7H-pyrrolo[2,3-d]pyrimidine derivatives, which are useful as a Janus kinase (JAK) inhibitor, intermediates thereof, and process for preparing the intermediates.

BACKGROUND

JAK belongs to a cytoplasmic protein tyrosine kinase family, and for example, includes JAK1, JAK2, JAK3, and TYK2.

Patent literature 1 discloses Compound A (Compound [19]: 3-[(3S,4R)-3-methyl-6-(7H-pyrrolo[2,3-d]pyrimidin-4-yl)-1,6-diazaspiro[3.4]octan-1-yl]-3-oxopropanenitrile) useful for a JAK inhibitor.

CONVENTIONAL ART LITERATURE

Patent Literature

Patent literature 1: WO 2011/013785

SUMMARY OF INVENTION

Problem to be Solved by the Invention

The present invention provides processes for preparing 7H-pyrrolo[2,3-d]pyrimidine derivatives which are useful as a JAK inhibitor, intermediates of the derivatives, and processes for preparing the intermediates.

Means for Solving the Problem

The present invention includes the following embodiment:

A process for preparing a compound of formula [19]

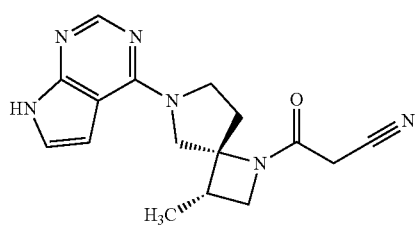

[19]

or its salt, or a solvate thereof using a compound of formula [14]

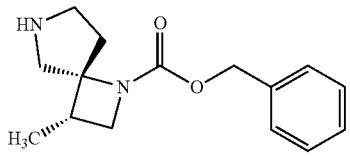

[14]

or a salt thereof with an organic acid, comprising the following steps:

(1) the step of reacting the compound of formula [14] or a salt thereof with an organic acid with a compound of formula [20]

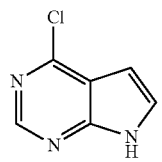

[20]

or a salt thereof to give a compound of formula [16]

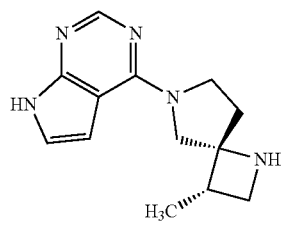

[16]

or its salt, (2) the step of removing a protecting group from the compound of formula [16] or its salt to give a compound of formula [17]

[17]

or its salt, and (3) the step of reacting the compound of formula [17] or its salt with a compound of formula [21]

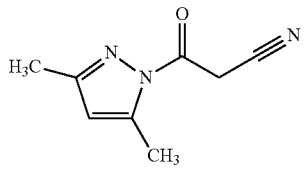

[21]

to give the compound of formula [19] or its salt, or a solvate thereof.

BRIEF DESCRIPTION OF DRAWINGS

FIG. 1 shows a multiple record for powder X-ray diffraction pattern of RS-ZMAA-DN.2H$_2$O. Diffraction intensity (cps: counts per second) is shown in the vertical axis, and diffraction angle 2θ (°) is shown in the horizontal axis.

FIG. 2 shows a multiple record for powder X-ray diffraction pattern of SR-MDOZ-OX. Diffraction intensity (cps: counts per second) is shown in the vertical axis, and diffraction angle 2θ (°) is shown in the horizontal axis.

FIG. 3 shows analytical results of HPLC for SR-MDOZ in Example 10. Absorbance (AU) is shown in the vertical axis, and retention time (min) is shown in the horizontal axis.

FIG. 4 shows analytical results of HPLC for SR-MDOZ-OX via the crystallization step in Example 11. Absorbance (AU) is shown in the vertical axis, and retention time (min) is shown in the horizontal axis.

FIG. 5 shows a multiple record for powder X-ray diffraction pattern of 1-ethanolate of Compound A. Diffraction intensity (cps: counts per second) is shown in the vertical axis, and diffraction angle 2θ (0) is shown in the horizontal axis.

FIG. 6 shows a multiple record for powder X-ray diffraction pattern of 1-ethanolate of Compound A. Diffraction intensity (cps: counts per second) is shown in the vertical axis, and diffraction angle 2θ (°) is shown in the horizontal axis.

DESCRIPTION OF EMBODIMENTS

The definitions of the terms herein are as below.

A compound of formula [14] may be, for example, referred to as Compound [14] herein.

The term "halogen" includes, for example, fluorine, chlorine, bromine, or iodine. A preferable halogen is bromine.

Salts of compounds may be any salts if such salts can be formed with the compound of the present invention, and includes, for example, salts with inorganic acids, salts with organic acids, salts with inorganic bases, salts with organic bases, salts with amino acids.

The inorganic acids include, for example, hydrochloric acid, nitric acid, sulfuric acid, phosphoric acid, hydrobromic acid. Preferable inorganic acids are sulfuric acid or hydrochloric acid.

The organic acids include, for example, oxalic acid, malonic acid, maleic acid, citric acid, fumaric acid, terephthalic acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid. Preferable organic acids are oxalic acid, fumaric acid, terephthalic acid, L-tartaric acid or D-tartaric acid. More preferable organic acids are oxalic acid, L-tartaric acid or D-tartaric acid.

The salts with inorganic bases include, for example, sodium salt, potassium salt, calcium salt, magnesium salt, ammonium salt. Preferable salts with inorganic bases are sodium salt, potassium salt, or calcium salt.

The organic bases include, for example, methylamine, diethylamine, trimethylamine, triethylamine, ethanolamine, diethanolamine, triethanolamine, ethylenediamine, tris(hydroxymethyl)methylamine, dicyclohexylamine, N,N-dibenzylethylenediamine, guanidine, pyridine, picoline, choline, cinchonine, meglumine. A preferable organic base is dicyclohexylamine.

The amino acids include, for example, lysine, arginine, aspartic acid, glutamic acid.

According to known methods, a compound of the present invention may be reacted with inorganic bases, organic bases, inorganic acids, organic acids, or amino acids to give salts of the compound of the present invention.

A chlorinating agent includes, for example, methanesulfonyl chloride, thionyl chloride. A preferable chlorinating agent is methanesulfonyl chloride.

A mesylating agent includes, for example, methanesulfonyl chloride, methanesulfonic acid anhydride. A preferable mesylating agent is methanesulfonyl chloride.

A compound or its salt of the present invention may exist as its solvate.

The solvate is a compound where a molecule of a solvent coordinates to the compound or its salt of the present invention, and includes a hydrate. A preferable solvate is a pharmaceutically acceptable solvate, and includes, for example, a hydrate, an ethanolate, a solvate with dimethylsulfoxide, a propanolate, an isopropanolate, a solvate with chloroform, a solvate with dioxane, a solvate with anisole, a solvate with acetone, a solvate with ethyleneglycol, or a solvate with dimethylacetamide of a compound or its salt of the present invention.

According to known methods, a solvate of a compound or its salt of the present invention may be obtained.

A compound of the present invention may exist as a tautomer. In such case, the compound of the present invention may exist as a single tautomer or a mixture of individual tautomers.

A compound of the present invention may have a carbon-carbon double bond. In such case, the compound of the present invention may exist as E form, Z from, or a mixture of E form and Z form.

A compound of the present invention may exist as a stereoisomer to be identified as a cis/trans isomer. In such case, the compound of the present invention may exist as a cis form, trans form, or a mixture of a cis form and a trans form.

A compound of the present invention may have one or more asymmetric carbon atoms. In such case, the compound of the present invention may exist as a single enatiomer, a single diastereomer, a mixture of enantiomers, or a mixture of diastereomers.

A compound of the present invention may exist as an atropisomer. In such case, the compound of the present invention may exist as a single atropisomer, or a mixture of individual atropisomers.

A compound of the present invention may simultaneously include several structural features causing the above isomers. A compound of the present invention may include the above isomers in any ratios.

In the absence of other reference such as annotation and the like, the formulae, chemical structures and compound names referred hereto without specifying a stereochemistry thereof may encompass all the above-mentioned isomers that may exist.

A chemical bond shown in a wavy line represents that the compound is a mixture of stereoisomers or any of stereoisomers. For example, a compound of formula [4]

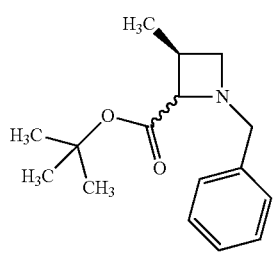

[4]

represents a mixture of formulae [4-1] and [4-2]

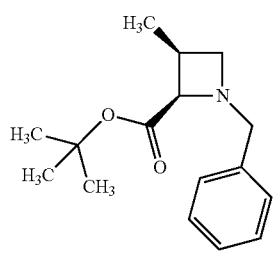

[4-1]

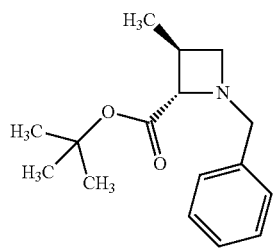

[4-2]

or any one of the isomers.

A diastereomeric mixture may be separated into each diastereomer by a conventional method such as chromatography or crystallization. Each diastereomer may be also obtained from a stereochemically single starting material or by a synthetic method comprising a stereoselective reaction.

A separation of enantiomeric mixture into each single enantiomer may be carried out by well-known methods in the field.

For example, a diastereomer with a higher isomeric ratio or a substantially pure single diastereomer may be separated from a diastereomeric mixture which is formed by reacting an enantiomeric mixture with a chiral auxiliary which is a substantially pure enantiomer according to a standard method such as fractional crystallization or chromatography. The separated diastereomer may be converted into the desired enantiomer by removing off the added chiral auxiliary in a cleavage reaction.

The desired enantiomer may be also obtained by directly separating an enantiomeric mixture by a chromatography using a chiral solid phase well known in the field.

Alternatively, the desired enantiomer may be also obtained from a substantially pure optically active starting material or by a stereoselective synthesis using a chiral auxiliary or asymmetric catalyst to a prochiral intermediate, i.e. asymmetric induction.

An absolute configuration may be determined by X-ray crystal analysis of a crystalline product or intermediate. If necessary, an absolute configuration may be determined from a crystalline product or intermediate derivatized with a reagent having an asymmetric center of which a steric configuration is known. The configuration herein was specified by X-ray crystal analysis of a crystallline chloroformate of Compound [19].

A compound of the present invention may be crystalline or amorphous.

A compound of the present invention may be labelled with an isotope including $^{3}H$, $^{14}C$, $^{35}S$.

Processes for preparing a compound of the present invention or its salt, or a solvate thereof is illustrated as below.

In each step, each reaction may be carried out in a solvent.

A compound obtained in each step may be isolated and purified by a known method such as distillation, recrystallization, column chromatography, if needed, or may be optionally used in a subsequent step without isolation or purification.

The room temperature herein represents a condition wherein a temperature is not controlled, and represents 1° C. to 40° C. as one embodiment. The reaction temperature may include the temperature as described ±5° C., preferably ±2° C.

[Process for Preparation 1] Preparation of Compound of Formula [4] or its Salt

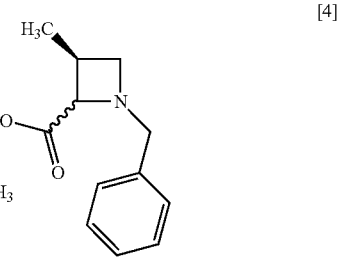

[4]

Step 1

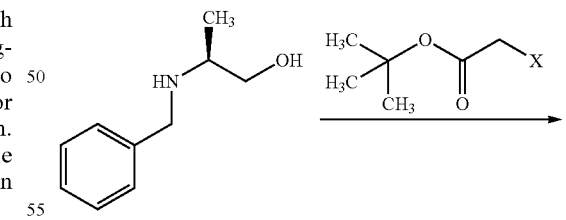

[1]

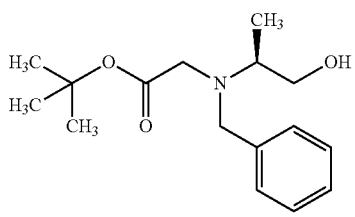

[2]

[In the formula, X is halogen.]

The compound of formula [2] may be prepared by reacting the compound of formula [1] with halogenated acetic acid tert-butyl ester in the presence of a base. Benzyl group in the compound of formula [1] may be substituted with an amine protecting group such as 4-chlorobenzyl group, 3-chlorobenzyl group, 4-methoxybenzyl group, 3-methoxybenzyl group, 4-methylbenzyl group, 3-methylbenzyl group, benzhydryl group, trityl group.

The halogenated acetic acid tert-butyl ester includes, for example, bromoacetic acid tert-butyl ester (TBBA), chloroacetic acid tert-butyl ester. The halogenated acetic acid tert-butyl ester may be substituted with halogenated acetic acid methyl ester, halogenated acetic acid ethyl ester. The preferable halogenated acetic acid tert-butyl ester is TBBA.

The solvent includes, for example, a mixed solvent of toluene-water, tetrahydrofuran. The preferable solvent is a mixed solvent of toluene-water.

The base includes, for example, potassium carbonate, N,N-diisopropylethylamine. The preferable base is potassium carbonate. The base may be, for example, used in an amount of 1.0 to 2.0 equivalents to the compound of formula [1], preferably 1.1 equivalents.

The reaction temperature is, for example, room temperature to 80° C., preferably 65° C.±5° C.

The reaction time is, for example, 5 to 48 hours, preferably 10 to 24 hours.
Step 2

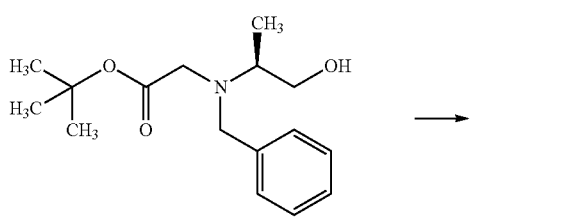

[2]

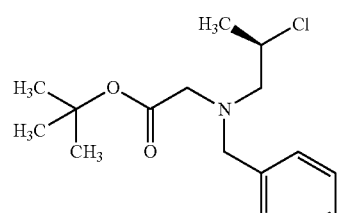

[3]

The compound of formula [3] may be prepared by reacting the compound of formula [2] with a chlorinating agent in the presence of a base according to the method of SYNLETT 2006, No. 5, pp 0781-0785.

The chlorinating agent includes, for example, methanesulfonyl chloride, thionyl chloride. The preferable chlorinating agent is methanesulfonyl chloride.

The solvent includes, for example, toluene, tetrahydrofuran, and a mixture thereof. The preferable solvent is a mixed solvent of toluene-tetrahydrofuran.

The base includes, for example, triethylamine, N,N-diisopropylethylamine. The preferable base is triethylamine. The base may be, for example, used in an amount of 1.0 to 1.5 equivalents to the compound of formula [2], preferably 1.2 equivalents.

The reaction temperature is, for example, 0° C. to 80° C., preferably 65° C.±5° C. The reaction time is, for example, 5 to 30 hours, preferably 8 to 24 hours.
Step 3

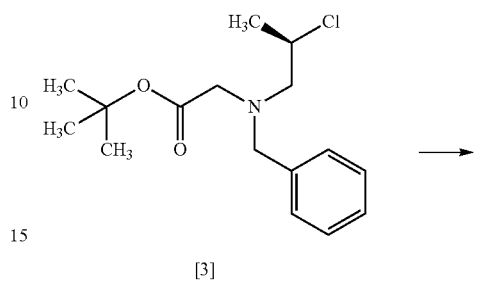

[3]

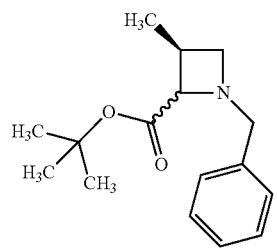

[4]

The compound of formula [4] may be prepared by cyclizing the compound of formula [3] in the presence of a base.

The solvent includes, for example, tetrahydrofuran, toluene, and a mixed solvent of these solvents. The preferable solvent is tetrahydrofuran or a mixed solvent of tetrahydrofuran and toluene.

The base includes, for example, lithium bis(trimethylsilyl)amide, lithium diisopropylamide. The preferable base is lithium bis(trimethylsilyl)amide. The base may be, for example, used in an amount of 0.95 to 1.3 equivalents to the compound of formula [3], preferably 1.1 equivalents.

The reaction temperature is, for example, −10° C. to 10° C., preferably 0° C. to 5° C.

The reaction time is, for example, 1 to 5 hours, preferably 1 to 2 hours. The compound of formula [4] may be obtained as a crystal by forming a salt with an acid.

The acid includes, for example, hydrochloric acid, nitric acid, sulfuric acid, phosphoric acid, hydrobromic acid. The preferable acid is hydrochloric acid. For example, a monohydrochloride of the compound of formula [4] may be obtained by adding hydrochloric acid to the compound of formula [4].

[Process for Preparation 2] Preparation of the Compound of Formula [6]

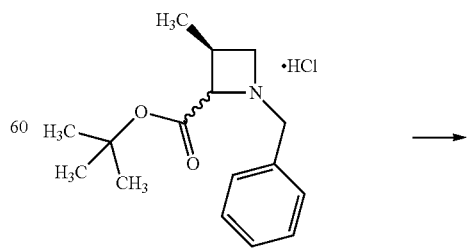

[5]

[6]

The compound of formula [6] may be prepared by removing a protecting group in the compound of formula [5] which is a hydrochloride of the compound of formula [4]. Any known method may be used for deprotecting, and for example, the compound of formula [5] may be hydrogenated in the presence of 5% palladium carbon (wetted with 50% water) as a catalyst to give a compound of formula [6].

The free form of the compound of formula [6] may be prepared from the compound of formula [4] in a similar manner. The formation of a salt from the free form and the formation of the free form from a salt may be carried out according to known methods.

The solvent includes, for example, methanol, ethanol. The preferable solvent is methanol.

The catalyst includes, for example, 5% palladium carbon (wetted with 50% water), palladium carbon, palladium hydroxide on carbon or palladium black. The preferable catalyst includes 5% palladium carbon (wetted with 50% water). The catalyst may be, for example, used in an amount of 0.1 to 0.3 folds to the weight of the compound of formula [5], preferably 0.2±0.05 folds.

The hydrogen gas pressure is, for example, 0.1 MPa to 0.5 MPa, preferably 0.4 MPa±0.1 MPa.

The reaction temperature is room temperature.

The reaction time is, for example, 5 to 24 hours, preferably 8 to 12 hours.

[Process for Preparation 3] Preparation of the Compound of Formula [7]

[6]
→
[7]

The compound of formula [7] may be prepared by reacting the compound of formula [6] or its free form with halogenated formic acid benzyl ester in the presence of a base. The benzyloxycarbonyl group in formula [7] may be substituted with an amine protecting group such as tert-butyloxycarbonyl group, 9-fluorenylmethyloxycarbonyl group.

The solvent includes, for example, methanol, tetrahydrofuran, toluene, and a mixed solvent thereof. The preferable solvent is a mixed solvent of methanol-tetrahydrofuran.

The base includes, for example, N,N-diisopropylethylamine, triethylamine. The preferable base is N,N-diisopropylethylamine.

The halogenated formic acid benzyl ester includes benzyl chloroformate. The preferable halogenated formic acid benzyl ester is benzyl chloroformate. The amount of the halogenated formic acid benzyl ester is 0.95 to 1.10 equivalents to the compound of formula [6], preferably 1.05±0.05 equivalents.

The reaction temperature is, for example, −5° C. to 10° C., preferably 0° C.±5° C.

The reaction time is, for example, 1 to 5 hours, preferably 1 to 2 hours.

[Process for Preparation 4] Preparation of the Compound of Formula [8]

[7]
→
[8]

[In the formula, X is halogen.]

The compound of formula [8] may be prepared by reacting the compound of formula [7] with halogenated acetic acid tert-butyl ester in the presence of a base under a low temperature.

The halogenated acetic acid tert-butyl ester includes, for example, bromoacetic acid tert-butyl ester (TBBA), chloroacetic acid tert-butyl ester. The halogenated acetic acid tert-butyl ester may be substituted with halogenated acetic acid methyl ester, halogenated acetic acid ethyl ester. The preferable halogenated acetic acid tert-butyl ester is TBBA.

The solvent includes, for example, tetrahydrofuran, hexane, and a mixed solvent of tetrahydrofuran and toluene. The preferable solvent is tetrahydrofuran or a mixed solvent of tetrahydrofuran and toluene.

The base includes, for example, lithium bis(trimethylsilyl)amide, lithium diisopropylamide. The preferable base is lithium bis(trimethylsilyl)amide. The base may be, for example, used in an amount of 0.95 to 1.2 equivalents to the compound of formula [7], preferably 1.05±0.05 equivalents.

The reaction temperature is, for example, −70° C. to −40° C., preferably −70° C. to −60° C.

The reaction time is, for example, 1 to 5 hours, preferably 1 to 3 hours.

[Process for Preparation 5] Preparation of the Compound of Formula [9]

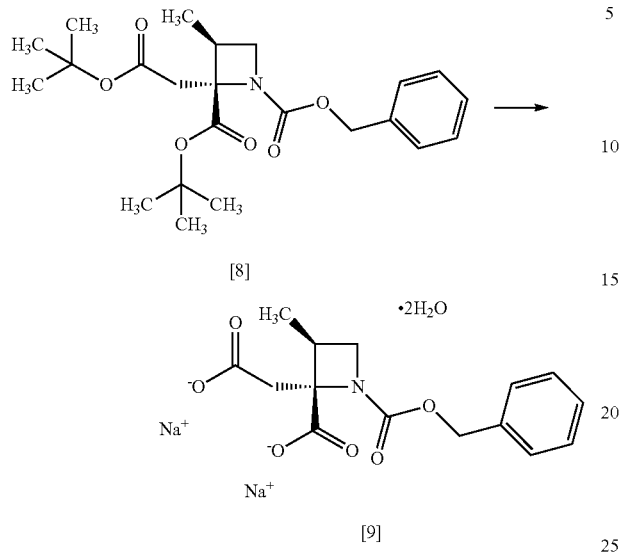

The compound of formula [9] may be prepared by a cleavage of tert-butyl ester in the compound of formula [8] in the presence of an acid, followed by the formation of a salt with sodium hydroxide. Other salts as well as the sodium salt may be formed from the compound of formula [8].

The compound of formula [9] in the form of a disodium salt dihydrate is preferable since SS-ZMAA, a diastereomer of RS-ZMAA, can be selectively removed by a crystallization.

The solvent includes, for example, acetonitrile, water, and a mixed solvent thereof. The preferable solvent is a mixed solvent of acetonitrile-water.

The acid includes, for example, p-toluenesulfonic acid, phosphoric acid. The preferable acid is p-toluenesulfonic acid. The acid may be, for example, used in an amount of 1.0 to 3.0 equivalents to the compound of formula [8], preferably 2.0±0.5 equivalents.

The reaction temperature is, for example, 40° C. to 60° C., preferably 40° C. to 55° C.

The reaction time is, for example, 5 to 24 hours, preferably 8 to 12 hours.

The compound of formula [9] is, for example, a crystal showing a powder X-ray diffraction pattern having at least one peak at 4.9°±0.2°, 12.3°±0.2°, 15.0°±0.2°, 19.2°±0.2°, or 22.7°+0.2° of the diffraction angle (2θ) measured using CuKα radiation.

Preferably, the compound of formula [9] is a crystal showing a powder X-ray diffraction pattern having at least one peak at 4.9°±0.1°, 12.3°±0.1°, 15.0°±00.1°, 19.2°±0.1, or 22.7°±0.1° of the diffraction angle (2θ) measured using CuKα radiation.

More preferably, the compound of formula [9] is a crystal showing a powder X-ray diffraction pattern having at least one peak at 4.90°±0.06°, 12.30°±0.06°, 15.0°±0.06°, 19.2°±0.06°, or 22.70±0.06° of the diffraction angle (2θ) measured using CuKα radiation.

[Process for Preparation 6] Preparation of the Compound of Formula [10]

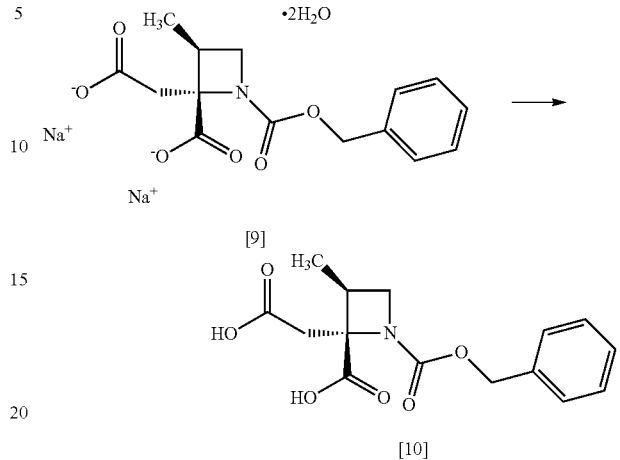

The compound of formula [10] may be prepared by neutralizing the compound of formula [9] with an acid.

The solvent includes, for example, acetonitrile, ethyl acetate, cyclopentylmethylether, a mixed solvent of ethyl acetate-acetonitrile, and a mixed solvent of cyclopentylmethylether-acetonitrile. The preferable solvent is a mixed solvent of ethyl acetate-acetonitrile.

The acid includes, for example, hydrochloric acid, sulfuric acid. The preferable acid is hydrochloric acid.

The compound of formula [10] may be also directly prepared without isolating the compound of formula [9] from the compound of formula [8].

[Process for Preparation 7] Preparation of the Compound of Formula [11]

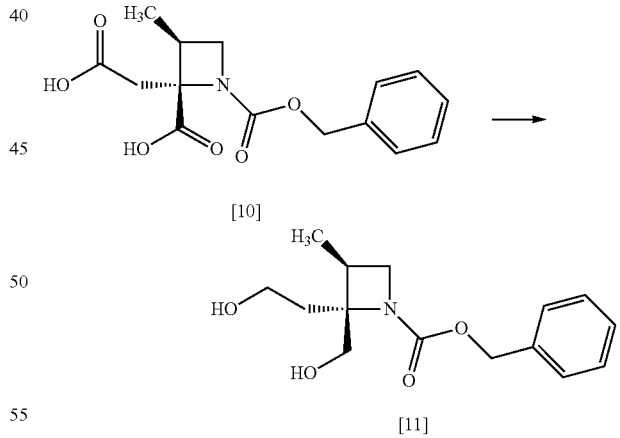

The compound of formula [11] may be prepared by reducing the compound of formula [10].

The solvent includes, for example, tetrahydrofuran, cyclopentylmethylether, toluene. The preferable solvent is tetrahydrofuran.

The reducing agent includes, for example, borane-tetrahydrofuran complex, sodium borohydride. The preferable reducing agent is borane-tetrahydrofuran complex. The reducing agent may be, for example, used in an amount of 1.9 to 3.0 to the compound of formula [10], preferably 2.25±0.25 equivalents. The acid to be added in the reaction includes, for example, boron trifluoride diethylether complex, methanesulfonic acid. The preferable acid is boron trifluoride diethylether complex. The yields of SR-MDOZ-OX may be improved in the case where borane-tetrahydrofuran complex is used as the reducing agent in the presence of boron trifluoride diethylether complex than the case where sodium borohydride is used as the reducing agent in the presence of boron trifluoride diethylether complex.

The reaction temperature is, for example, −5° C. to 30° C., preferably 20° C. to 25° C.

The reaction time is, for example, 5 to 24 hours, preferably 8 to 15 hours.

[Process for Preparation 8] Preparation of the Compound of Formula [11]

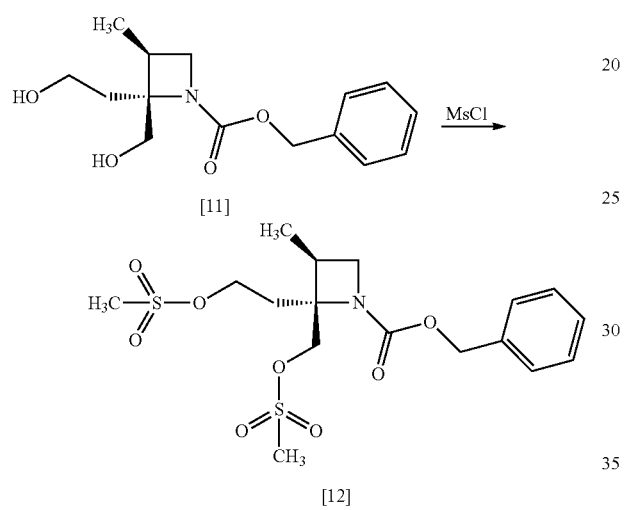

The compound of formula [12] may be prepared by sulfonylating the compound of formula [11] in the presence of a base. Instead of the sulfonylating agent having mesyl group as shown, a sulfonylating agent having a leaving group such as tosyl group, benzenesulfonyl group, 3-nitrobenzenesulfonyl group, 4-nitrobenzenesulfonyl group, and trifluoromethanesulfonyl group may also be used.

The solvent includes, for example, toluene, ethyl acetate. The preferable solvent is toluene.

The base includes, for example, triethylamine, N,N-diisopropylethylamine. The preferable base is triethylamine.

The sulfonylating agent includes, for example, methanesulfonyl chloride, methanesulfonic acid anhydride, p-toluenesulfonyl chloride, p-toluenesulfonyl bromide, benzenesulfonyl chloride, benzenesulfonyl bromide, 3-nitrobenzenesulfonyl chloride, 4-nitrobenzenesulfonyl chloride, and trifluoromethanesulfonyl chloride. The preferable one is methanesulfonyl chloride. The sulfonylating agent may be, for example, used in an amount of 1.9 to 2.2 equivalents to the compound of formula [11], preferably 2.1±0.05 equivalents.

The reaction temperature is, for example, −10° C. to 15° C., preferably 0° C. to 10° C.

The reaction time is, for example, 0.5 to 5 hours, preferably 1 to 2 hours.

The compound of formula [11] may be halogenated, instead of sulfonylation. The halogenation may be carried out according to conventional methods.

The halogenating agent includes, for example, thionyl chloride, oxalyl chloride, phosphorus tribromide, and a combination of carbon tetrabromide and triphenylphosphine.

[Process for Preparation 9] Preparation of the Compound of Formula [13]

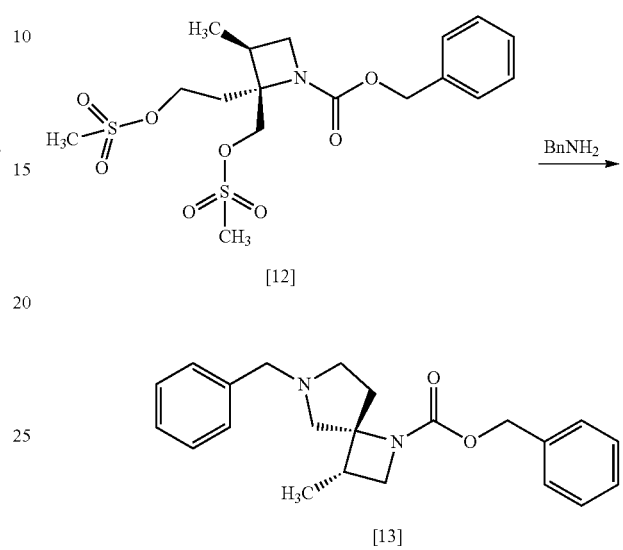

The compound of formula [13] may be prepared by cyclizing the compound of formula [12] with an amine compound.

The solvent includes, for example, toluene, acetonitrile. The preferable solvent is toluene.

The amine compound includes, for example, benzylamine. Benzylamine may be substituted with 3-methoxybenzyl amine, 4-methoxybenzyl amine, 3-methylbenzyl amine, 4-methylbenzyl amine, 3-chlorobenzyl amine, 4-chlorobenzyl amine, benzhydryl amine, triphenylmethylamine. The amine compound may be, for example, used in an amount of 6.0 to 8.0 equivalents to the compound of formula [12], preferably 7.0±0.5 equivalents.

The compound that benzyloxycarbonyl group is replaced with tert-butyloxycarbonyl group in the compound of formula [13] may be also prepared in a similar manner to the present method.

The reaction temperature is, for example, room temperature to 110° C., preferably 55° C. to 80° C.

The reaction time is, for example, 1 to 24 hours, preferably 8 to 16 hours.

[Process for Preparation 10] Preparation of the Compound of Formula [14]

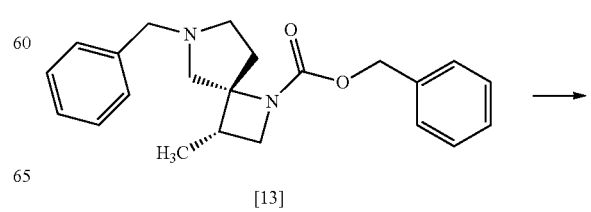

-continued

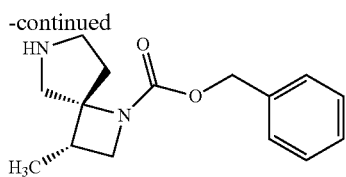

[14]

The compound of formula [14] may be prepared by removing the protecting group from the compound of formula [13] in the presence of 1-chloroethyl chloroformate, a base, and an alcohol.

The solvent includes, for example, toluene, ethyl acetate. The preferable solvent is toluene.

The base includes, for example, triethylamine, N,N-diisopropylethylamine. The preferable base is triethylamine.

The alcohol includes methyl alcohol, ethyl alcohol. The preferable alcohol is methyl alcohol.

The amount of 1-chloroethyl chloroformate is in the range of 1.0 to 2.0 equivalents to the compound of formula [13], preferably 1.1 equivalents.

The reaction temperature is, for example, from 0° C. to 80° C., preferably from room temperature to 60° C.

The reaction time is, for example, from 4 to 24 hours, preferably from 8 to 12 hours.

[Process for Preparation 11] Preparation of a Salt of the Compound of Formula

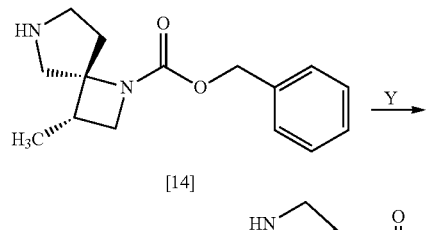

[In the formula, Y is an acid, n is any number of 0.5 to 2, for example 0.5, 1, 2.]

The compound of formula [15] may be prepared by forming a salt of the compound of formula [14] with an acid.

The solvent includes, for example, tetrahydrofuran, ethyl acetate. The preferable solvent is tetrahydorofuran.

The acid includes, for example, organic acid or inorganic acid.

The organic acid includes, for example, oxalic acid, malonic acid, maleic acid, citric acid, fumaric acid, terephthalic acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid. The preferable organic acid is oxalic acid, fumaric acid, terephthalic acid, L-tartaric acid, or D-tartaric acid. The more preferable organic acid is oxalic acid, L-tartaric acid, or D-tartaric acid.

The inorganic acid includes, for example, hydrochloric acid, nitric acid, sulfuric acid, phosphoric acid, hydrobromic acid. The preferable inorganic acid is sulfuric acid or hydrochloric acid.

The reaction temperature is, for example, room temperature to 60° C., preferably 15° C. to 60° C.

The reaction time is, for example, 4 to 24 hours, preferably 6 to 15 hours.

The compound of formula [15] includes, for example, monooxalate of the compound of formula [14], mono-L-tartrate of the compound of formula [14], mono-D-tartrate of the compound of formula [14], 0.5 terephthalate.0.5 ethanolate of the compound of formula [14], 0.5 terephthalate of the compound of formula [14](anhydrous crystal), 0.5 sulfate of the compound of formula [14], 0.5 oxalate of the compound of formula [14], monofumarate of the compound of formula [14]. Preferably, the compound of formula [15] is monooxalate of the compound of formula [14], mono-L-tartrate of the compound of formula [14], mono-D-tartrate of the compound of formula [14].

The compound of formula [15] is, for example, monooxalate of the compound of formula [14] which is a crystal showing a powder X-ray diffraction pattern having at least one peak at 6.5°±0.2', 9.0°±0.2°, 18.1°±0.2°, 20.1°±0.2θ, or 21.2°±0.2° of the diffraction angle (2θ) measured using CuKα radiation. Preferably, the compound of formula [15] is monooxalate of the compound of formula [14] which is a crystal showing a powder X-ray diffraction pattern having at least one peak at 6.5'±0.1°, 9.0°±0.1°, 18.1°±0.1°, 20.1°±0.1°, or 21.2°±0.1° of the diffraction angle (2θ) measured using CuKα radiation.

More preferably, the compound of formula [15] is monooxalate of the compound of formula [14] which is a crystal showing a powder X-ray diffraction pattern having at least one peak at 6.5°±0.06°, 9.0°±0.06°, 18.1°±0.06°, 20.1°±0.06°, or 21.2°±0.06° of the diffraction angle (2θ) measured using CuKα radiation.

[Process for Preparation 12] Preparation of the Compound of Formula [16]

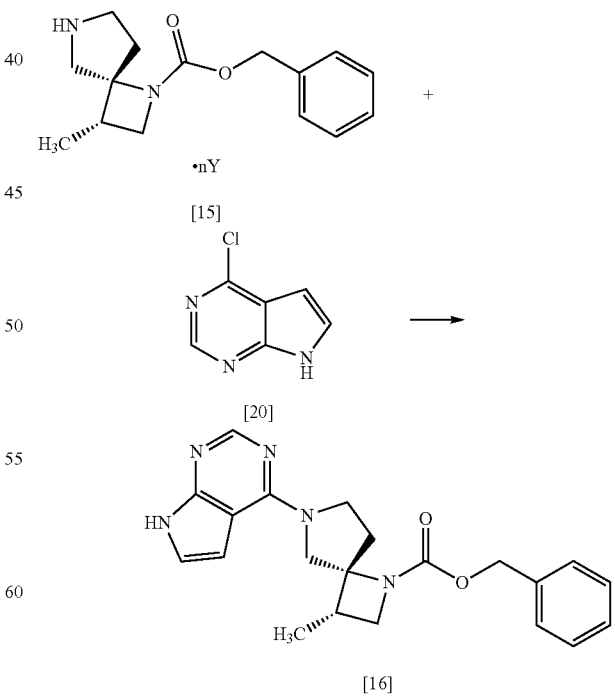

The compound of formula [16] may be prepared by condensing the compound of formula [15] with 4-chloro- 7H-pyrrolo[2,3-d]pyrimidine (CPPY) [20] in the presence of a base. The compound of formula [15] may be substituted with the compound of formula [14].

The solvent includes, for example, ethanol, methanol, and a mixed solvent of ethanol and water. The preferable solvent is ethanol or a mixed solvent of ethanol and water.

The base includes, for example, potassium phosphate, potassium carbonate. The preferable base is potassium phosphate. The more preferable base is tripotassium phosphate.

CPPY may be, for example, used in an amount of 0.95 to 1.10 equivalents to the compound of formula [15], preferably 1.02±0.02 equivalents.

The reaction temperature is, for example, room temperature to 85° C., preferably 80° C.±5° C.

The reaction time is, for example, 3 to 15 hours, preferably 4 to 8 hours.

[Process for Preparation 13] Preparation of the Compound of Formula [17]

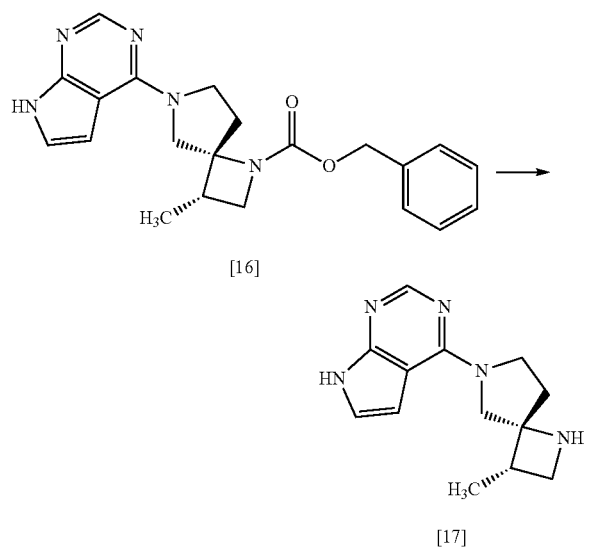

The compound of formula [17] may be prepared by removing a protecting group from the compound of formula [16]. Deprotecting may be carried out according to known methods, and for example, the compound of formula [17] may be prepared by adding ammonium formate to the compound of formula [16] in the presence of 10% palladium carbon (wetted with 50% water) as a catalyst. The compound of formula [16] and the compound of formula [17] may be respectively substituted with their salts, and the formation of a salt from a free form and the formation of a free form from a salt may be carried out according to known methods.

The solvent includes, for example, tert-butanol, water, ethanol, and a mixed solvent thereof. The preferable solvent is a mixed solvent of tert-butanol-water.

The catalyst includes, for example, 5% palladium carbon (wetted with 50% water), palladium carbon, palladium hydroxide on carbon or palladium black. The preferable catalyst includes 5% palladium carbon (wetted with 50% water). The catalyst may be, for example, used in an amount of 0.05 to 0.5 folds to the weight of the compound of formula [15], preferably 0.1±0.05 folds.

Ammonium formate may be, for example, used in an amount of 2.0 to 10 equivalents to the compound of formula [15], preferably 5.0±1.0 equivalents.

The reaction temperature is, for example, room temperature to 60° C., preferably 40° C. to 50° C.

The reaction time is, for example, 2 to 24 hours, preferably 5 to 15 hours.

[Process for Preparation 14] Preparation of the Compound of Formula [19]

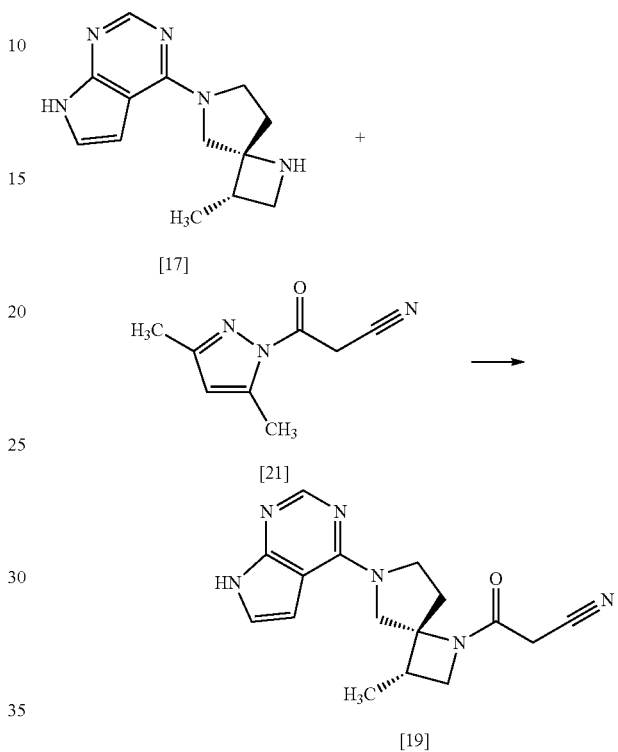

The compound of formula [19] may be prepared by condensing the compound of formula [17] with 1-cyanoacetyl-3,5-dimethyl-1H-pyrazole (DPCN) [21] in the presence of a base. The compound of formula [17] and the compound of formula [19] may be respectively substituted with their salts, and the formation of a salt from a free form and the formation of a free form from a salt may be carried out according to known methods.

The solvent includes, for example, acetonitrile, tetrahydrofuran. The preferable solvent is acetonitrile.

The base includes, for example, triethylamine, N,N-diisopropylethylamine. The preferable base is triethylamine.

DPCN may be, for example, used in an amount of 0.95 to 1.2 equivalents to the compound of formula [17], preferably 1.1±0.05 equivalents.

The reaction temperature is, for example, room temperature to 60° C., preferably 40° C. to 50° C.

The reaction time is, for example, 2 to 12 hours, preferably 3 to 6 hours.

In this reaction, the compound of formula [19] may be also prepared by condensing the compound of formula [17] with 1-cyanoacetyl-3,5-dimethyl-1H-pyrazole (DPCN) [21] without using the base. The compounds of formula [17] and formula [19] may be respectively substituted with their salts. The formation of such salts from their free forms may be carried out according to known methods, and vice versa.

The solvent includes, for example, acetonitrile and tetrahydrofuran. The preferable solvent is acetonitrile.

DPCN may be used in an amount of 0.95 to 1.2 equivalents to the compound of formula [17], preferably 1.05±0.05 equivalents.

The reaction temperature is, for example, room temperature to 80° C., preferably 70° C. to 80° C.

The reaction time is, for example, 0.5 to 12 hours, preferably 0.5 to 6 hours.

[Process for Preparation 15] Preparation of the Compound of Formula [18]

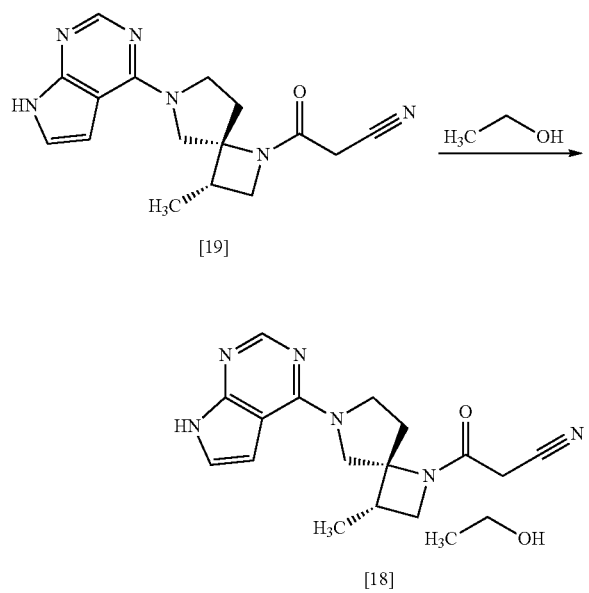

The compound of formula [18] may be prepared by crystallizing the compound of formula [19] with using a solvent. Ethanol in the compound of formula [18] may be substituted with propanol, isopropanol, chloroform, dioxane, anisole, acetone, ethyleneglycol, dimethylacetamide, water.

The solvent includes, for example, ethanol, propanol, isopropanol, chlroform, dioxane, anisole, acetone, ethyleneglycol, dimethylacetamide, water. The preferable solvent is ethanol.

The present step may not be necessary for the preparation of Compound [19], and may be carried out to improve the purity fo Compound [19].

The compound of formula [18] is, for example, a crystal showing a powder X-ray diffraction pattern having at least one peak at 8.3°±0.2°, 12.7°±0.2°, 13.0°±0.2°, 20.0°±0.2°, or 24.1°±0.2° of the diffraction angle (2θ) measured using CuKα radiation.

Preferably, the compound of formula [18] is a crystal showing a powder X-ray diffraction pattern having at least one peak at 8.3°±0.1°, 12.7°±0.1°, 13.0°±0.1°, 20.0°±0.1°, or 24.1°±0.1° of the diffraction angle (2θ) measured using CuKα radiation.

More preferably, the compound of formula [18] is a crystal showing a powder X-ray diffraction pattern having at least one peak at 8.3°±0.06°, 12.7°±0.06°, 13.0°±0.06°, 20.0°±0.06°, or 24.1°±0.06° of the diffraction angle (2θ) measured using CuKα radiation.

[Process for Preparation 16] Purification of the Compound of Formula [19]

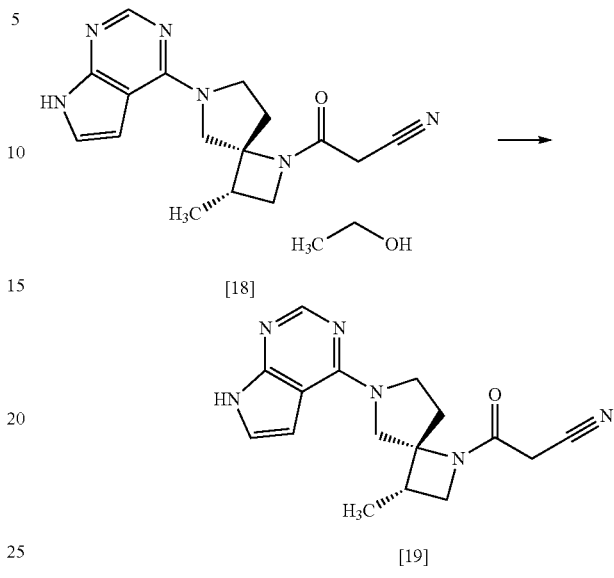

The compound of formula [19] may be purified by recrystallizing the compound of formula [18].

The solvent includes, for example, n-butanol, n-propanol. The preferable solvent is n-butanol. The solvent may be, for example, used in an amount of 8.0 to 20 folds to the weight of the compound of formula [18], preferably 8.5±0.5 folds.

The temperature that the crystal dissolves is, for example, 100° C. to 117° C., preferably 110° C.±5° C.

The time for recrystallization is, for example, 15 to 48 hours, preferably 18 to 24 hours.

The compound of formula [19] may be also purified by recrystallizing the compound of formula [19].

The solvent used herein includes, for example, n-butanol and n-propanol. The preferable solvent is n-butanol. The solvent may be used in an amount of 18 to 22 folds to the weight of the compound of formula [19], preferably 20±0.5 folds.

The temperature that the crystal dissolves is, for example, 85° C. to 100° C., preferably 90° C. to 100° C.

The time for recrystallization is, for example, 10 to 48 hours, preferably 10 to 24 hours.

The method for preparing the compound or its salt or a solvate thereof in the present invention may have the following advantages over the Preparation 6 in Patent literature 1.

(1) The present method is a synthetic route via SR-MDOZ [14] from S-ZMAB [7] avoiding ozone oxidation reaction and LAH reduction reaction which are inappropriate for a large-scale synthesis.

(2) The preparation of Compound A with a high optical purity may be achieved via the isolation step utilizing RS-ZMAA [9] in the present method.

(3) The preparation of Compound A with a high purity may be achieved via the isolation step utilizing a salt of SR-MDOZ [14].

Embodiments of the present invention include the following embodiments:

Item 1: A process for preparing a compound of formula [19]

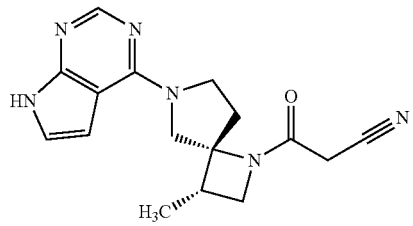

[19]

or its salt, or a solvate thereof using a compound of formula [14]

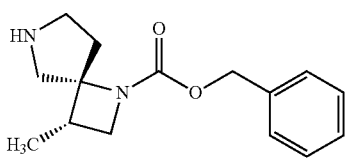

[14]

or a salt thereof with an organic acid, comprising the following steps:

(1) the step of reacting the compound of formula [14] or a salt thereof with an organic acid with a compound of formula [20]

[20]

or a salt thereof to give a compound of formula [16]

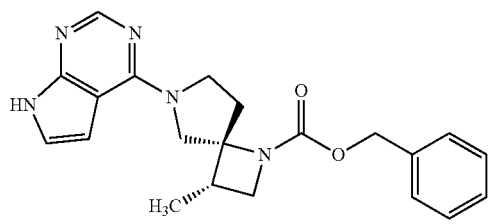

[16]

or its salt, (2) the step of removing a protecting group from the compound of formula [16] or its salt to give a compound of formula [17]

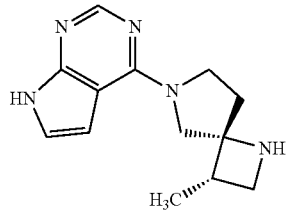

[17]

or its salt, and (3) the step of reacting the compound of formula [17] or its salt with a compound of formula [21]

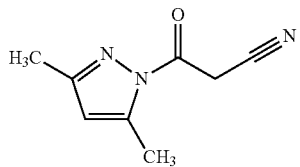

[21]

to give the compound of formula [19] or its salt, or a solvate thereof.

Item 2: The process of Item 1, further comprising the step of adding an organic acid to the compound of formula [14] to give a salt of the compound of formula [14] with the organic acid.

Item 3: The process of Item 1 or 2, further comprising the step of removing $R^1$ group from a compound of formula [13']

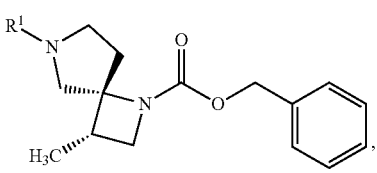

[13']

wherein $R^1$ is benzyl, 3-methoxybenzyl, 4-methoxybenzyl, 3-methylbenzyl, 4-methylbenzyl, 3-chlorobenzyl, 4-chlorobenzyl, benzhydryl or trityl, to give the compound of formula [14].

Item 4: The process of Item 1 or 2, further comprising the step of removing benzyl group from a compound of formula [13]

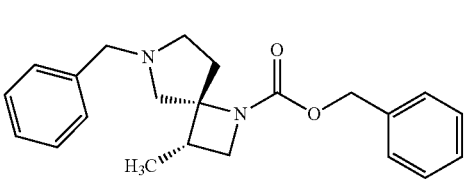

[13]

to give the compound of formula [14].

Item 5: The process of Item 3, further comprising the step of reacting a compound of formula [12']

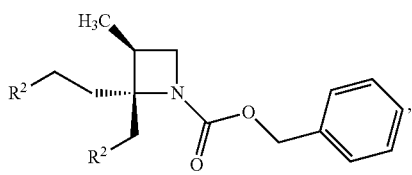

wherein R² is methanesulfonyloxy, p-toluenesulfonyloxy, benzenesulfonyloxy, 3-nitrobenzenesulfonyloxy, 4-nitrobenzenesulfonyloxy, trifluoromethanesulfonyloxy, chloro or bromo, with R¹—NH₂ to give the compound of formula [13'].

Item 6: The process of Item 4, further comprising the step of reacting a compound of formula [12]

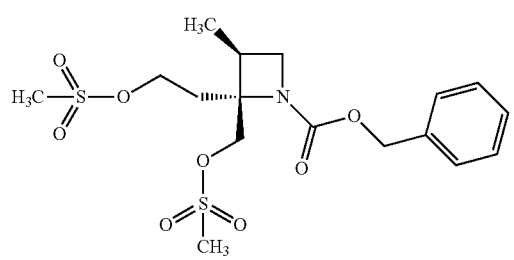

with benzylamine to give the compound of formula [13].

Item 7: The process of Item 5, further comprising the step of reacting a compound of formula [11]

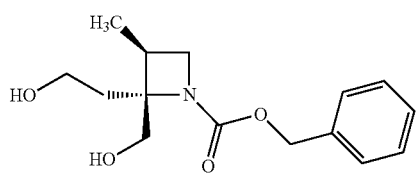

with a sulfonylating agent or a halogenating agent to give the compound of formula [12'].

Item 8: The process of Item 6, further comprising the step of reacting a compound of formula [11]

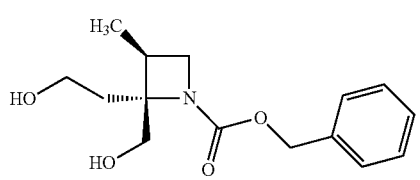

with a mesylating agent to give the compound of formula [12].

Item 9: The process of Item 7 or 8, further comprising the step of reducing a compound of formula [10]

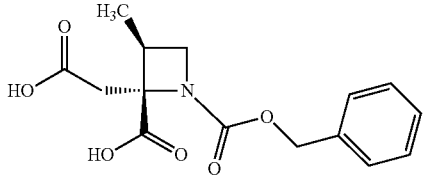

to give the compound of formula [11].

Item 10: The process of Item 9, wherein the reduction is carried out in the presence of boron trifluoride-diethyl ether complex and borane-tetrahydrofuran complex.

Item 11: The process of either Item 9 or 10, further comprising the step of removing a salt and a solvent from a disodium salt dihydrate of the compound of formula [10]

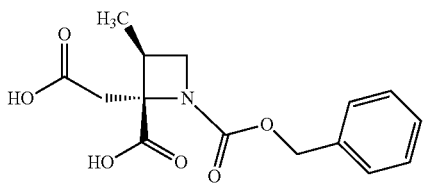

to give the compound of formula [10].

Item 12: The process of Item 11, further comprising the step of obtaining the disodium salt dihydrate of the compound of formula [10] from a compound of formula [8']

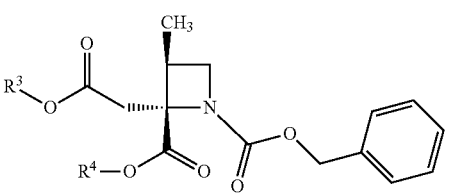

wherein R³ and R⁴ are each independently methyl, ethyl or tert-butyl.

Item 13: The process of Item 11, further comprising the step of obtaining the disodium salt dihydrate of the compound of formula [10] from a compound of formula [8]

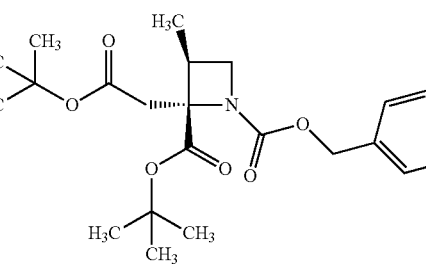

Item 14: The process of Item 12, further comprising the step of reacting a compound of formula [7']

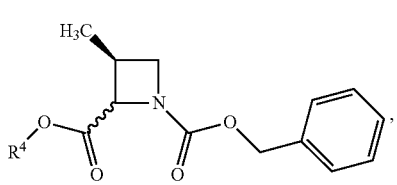
[7']

wherein $R^4$ is the same as defined above, with halogenated acetic acid alkyl ester wherein the alkyl is methyl, ethyl or tert-butyl to give the compound of formula [8'].

Item 15: The process of Item 13, further comprising the step of reacting a compound of formula [7]

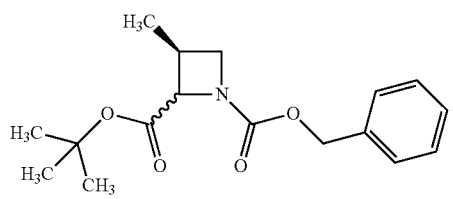
[7]

with halogenated acetic acid tert-butyl ester to give the compound of formula [8].

Item 16: The process of Item 14, further comprising the step of reacting a compound of formula [6']

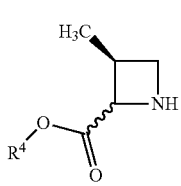
[6']

wherein $R^4$ is the same as defined above, or a salt thereof with halogenated formic acid benzyl ester to give the compound of formula [7'].

Item 17: The process of Item 15, further comprising the step of reacting a compound of formula [6]

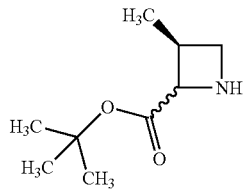
[6]

or its salt with halogenated formic acid benzyl ester to give the compound of formula [7].

Item 18: The process of Item 16, further comprising the step of removing $P^N$ group from a compound of formula [4']

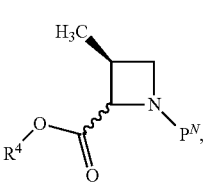
[4']

wherein $P^N$ is benzyl, 4-chlorobenzyl, 3-chlorobenzyl, 4-methoxybenzyl, 3-methoxybenzyl, 4-methylbenzyl, 3-methylbenzyl, benzhydryl or trityl, and $R^4$ is the same as defined above, or a salt thereof to give the compound of formula [6'] or a salt thereof.

Item 19: The process of Item 17, further comprising the step of removing a protecting group from a compound of formula [4]

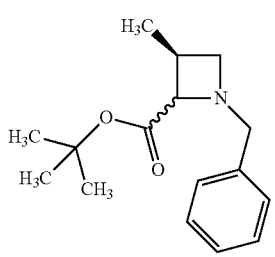
[4]

or its salt to give the compound of formula [6] or its salt.

Item 20: A compound of formula [14]

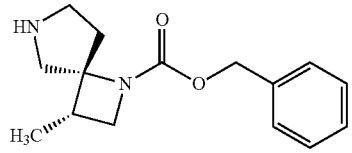
[14]

or its salt with an organic acid.

Item 21: A crystal of monooxalate of a compound of formula [14]

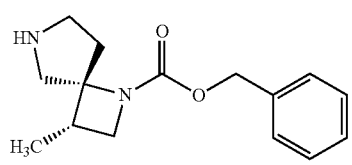
[14]

showing a powder X-ray diffraction pattern having at least one peak at 6.5°±0.2°, 9.0°±0.2°, 18.1°±0.2°, 20.1°±0.2°, or 21.2°±0.2° of a diffraction angle (2θ) determined by using CuKα radiation.

Item 22: The salt of Item 20, wherein the salt with an organic acid is monooxalate.

Item 23: The salt of Item 20, wherein the salt with an organic acid is monofumarate.

Item 24: The salt of Item 20, wherein the salt with an organic acid is mono-L-tartrate.

Item 25: The salt of Item 20, wherein the salt with an organic acid is mono-D-tartrate.

Item 26: A process for preparing a compound of formula [14]

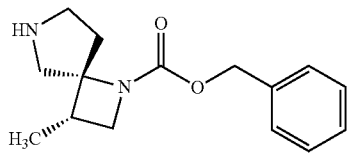

or its salt, or a solvate thereof, comprising the step of adding an organic acid to the compound of formula [14] to give a salt of the compound of formula [14] with the organic acid.

Item 27: The process of Item 26, further comprising the step of removing $R^1$ group from a compound of formula [13']

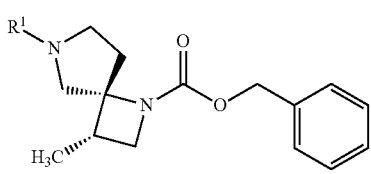

wherein $R^1$ is the same as defined above to give the compound of formula [14].

Item 28: The process of Item 26, further comprising the step of removing benzyl group from a compound of formula [13]

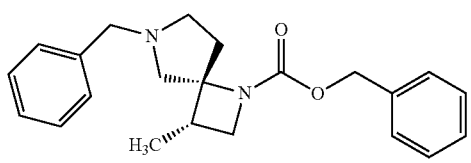

to give the compound of formula [14].

Item 29: The process of Item 27, further comprising the step of reacting a compound of formula [12']

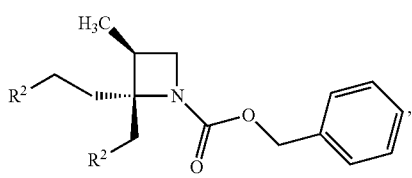

wherein $R^2$ is the same as defined above, with $R^1$—$NH_2$ to give the compound of formula [13'].

Item 30: The process of Item 28, further comprising the step of reacting a compound of formula [12]

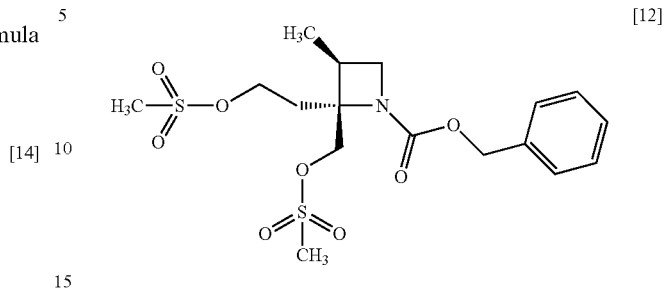

with benzylamine to give the compound of formula [13].

Item 31: The process of Item 29, further comprising the step of reacting a compound of formula [11]

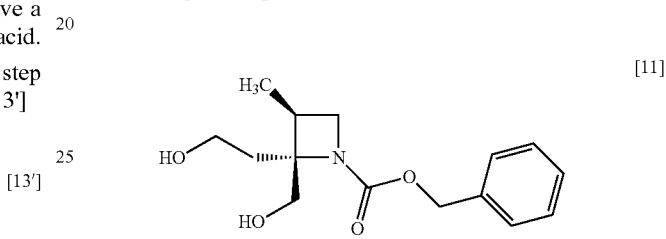

with a sulfonylating agent or a halogenating agent to give the compound of formula [12'].

Item 32: The process of Item 30, further comprising the step of reacting a compound of formula [11]

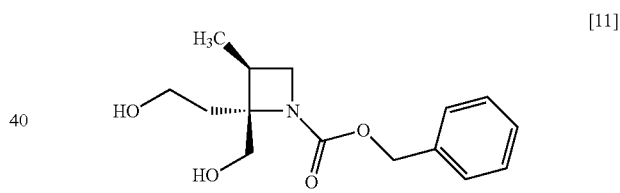

with a mesylating agent to give the compound of formula [12].

Item 33: The process of Item 31 or 32, further comprising the step of reducing a compound of formula [10]

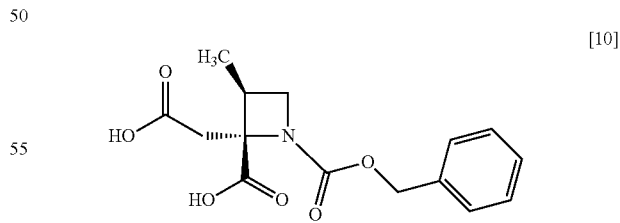

to give the compound of formula [11].

Item 34: The process of Item 33, wherein the reduction is carried out in the presence of boron trifluoride-diethyl ether complex and borane-tetrahydrofuran complex.

Item 35: The process of either Item 33 or 34, further comprising the step of removing a salt and a solvent from a disodium salt dihydrate of the compound of formula [10] to give the compound of formula [10].

Item 36: The process of Item 35, further comprising the step of obtaining the disodium salt dihydrate of the compound of formula [10] from a compound of formula [8']

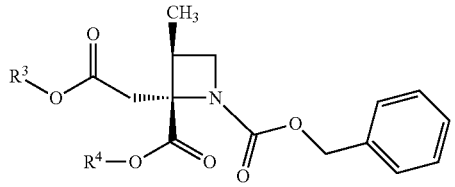

wherein $R^3$ and $R^4$ are the same as defined above.

Item 37: The process of Item 35, further comprising the step of obtaining the disodium salt dihydrate of the compound of formula [10] from a compound of formula [8]

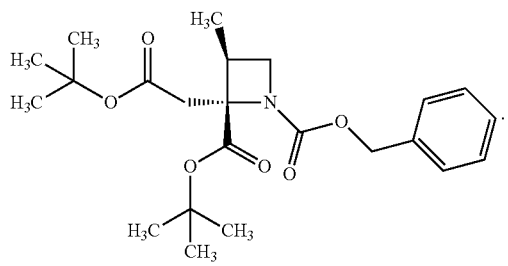

Item 38: The process of Item 36, further comprising the step of reacting a compound of formula [7']

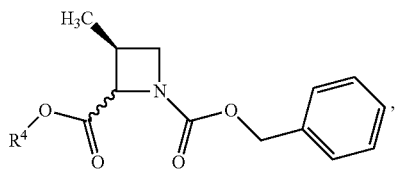

wherein $R^4$ is the same as defined above, with halogenated acetic acid alkyl ester wherein the alkyl is methyl, ethyl or tert-butyl to give the compound of formula [8'].

Item 39: The process of Item 37, further comprising the step of reacting a compound of formula [7]

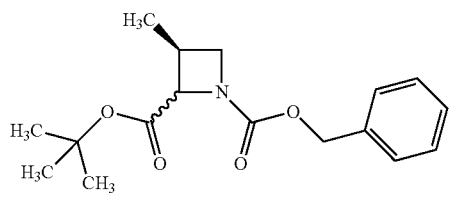

with halogenated acetic acid tert-butyl ester to give the compound of formula [8].

Item 40: The process of Item 38, further comprising the step of reacting a compound of formula [6']

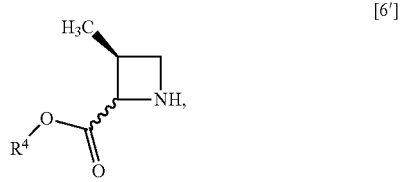

wherein $R^4$ is the same as defined above, or a salt thereof with halogenated formic acid benzyl ester to give the compound of formula [7'].

Item 41: The process of Item 39, further comprising the step of reacting a compound of formula [6]

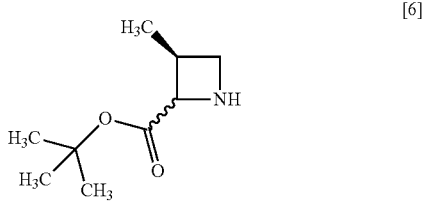

or its salt with halogenated formic acid benzyl ester to give the compound of formula [7].

Item 42: The process of Item 40, further comprising the step of removing $P^N$ group from a compound of formula [4']

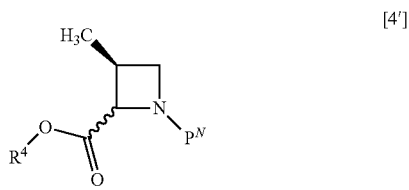

wherein $R^4$ and $P^N$ are the same as defined above, or a salt thereof to give the compound of formula [6'] or a salt thereof.

Item 43: The process of Item 41, further comprising the step of removing a protecting group from a compound of formula [4]

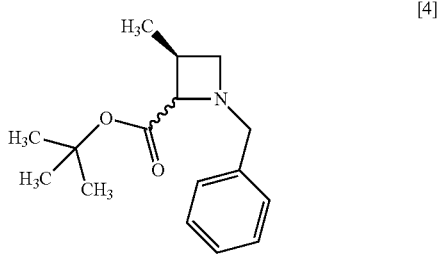 [SMILES: C[C@H]1CN(Cc2ccccc2)C1C(=O)OC(C)(C)C]

or its salt to give the compound of formula [6].

Item 44: A disodium salt dihydrate of a compound of formula [10]

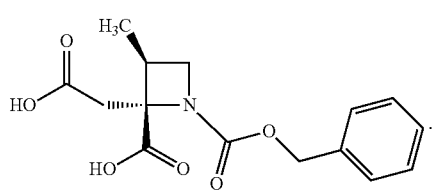
[10]

Item 45: A crystal of a disodium salt dihydrate of a compound of formula [10]

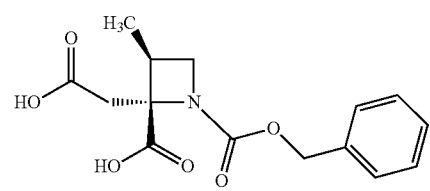
[10]

showing a powder X-ray diffraction pattern having at least one peak at 4.9°±0.2°, 12.3°±0.2°, 15.0°±0.2°, 19.2°±0.2°, or 22.7°±0.2° of a diffraction angle (2θ) determined by using CuKα radiation.

Item 46: A process for preparing a disodium salt dihydrate of a compound of formula [10]

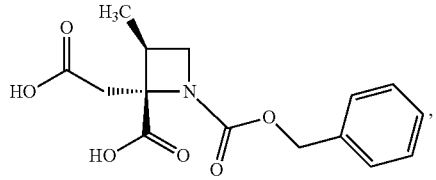
[10]

comprising the step of obtaining the disodium salt dihydrate of a compound of formula [10] from a compound of formula [8']

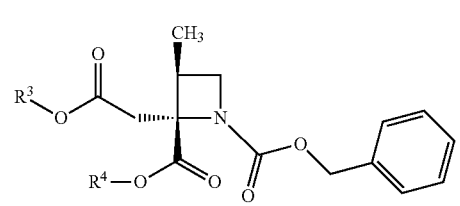
[8']

wherein $R^3$ and $R^4$ is the same as defined above.

Item 47: A process for preparing a disodium salt dihydrate of a compound of formula [10]

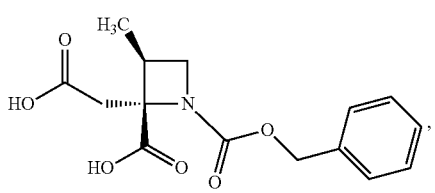
[10]

comprising the step of obtaining the disodium salt dihydrate of the compound of formula [10] from a compound of formula [8]

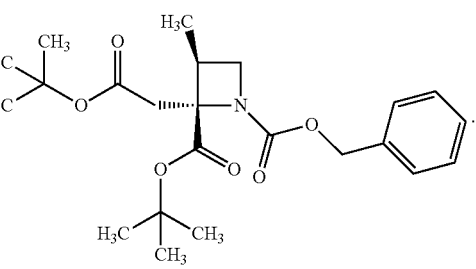
[8]

Item 48: The process of Item 46, further comprising the step of reacting a compound of formula [7']

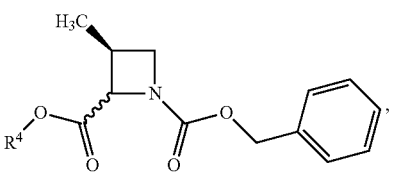
[7']

wherein $R^4$ is the same as defined above, with halogenated acetic acid alkyl ester wherein the alkyl is methyl, ethyl or tert-butyl to give a compound of formula [8'].

Item 49: The process of Item 47, further comprising the step of reacting a compound of formula [7]

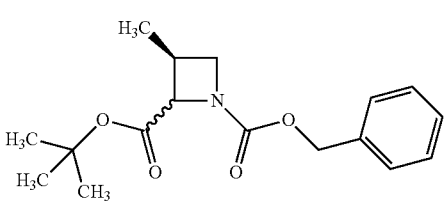
[7]

with halogenated acetic acid tert-butyl ester to give the compound of formula [8].

Item 50: The process of Item 48, further comprising the step of reacting a compound of formula [6']

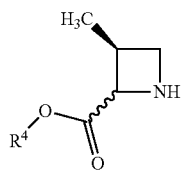

[6']

wherein R⁴ is the same as defined above, or a salt thereof with halogenated formic acid benzyl ester to give the compound of formula [7'].

Item 51: The process of Item 49, further comprising the step of reacting a compound of formula [6]

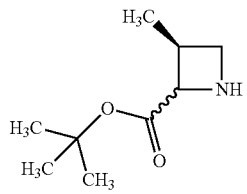

[6]

or its salt with halogenated formic acid benzyl ester to give the compound of formula [7].

Item 52: The process of Item 50, further comprising the step of removing P^N group from a compound of formula [4']

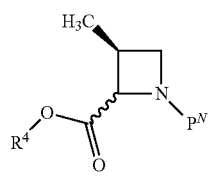

[4']

wherein R⁴ and P^N are the same as defined above, or a salt thereof to give the compound of formula [6'] or a salt thereof.

Item 53: The process of Item 51, further comprising the step of removing a protecting group from a compound of formula [4]

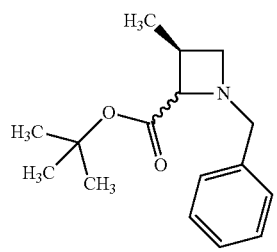

[4]

or its salt to give a compound of formula [6] or its salt.

Item 54: A process for preparing a compound of formula [11]

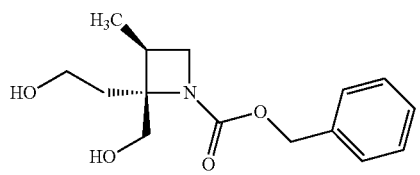

[11]

by reducing a compound of formula [10]

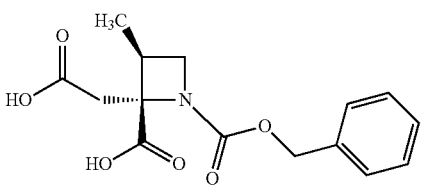

[10]

in the presence of boron trifluoride-diethyl ether complex and borane-tetrahydrofuran complex.

Item 55: A compound of formula [19]

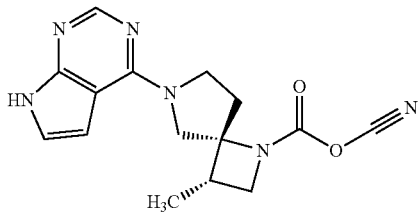

[19]

or its salt or a solvate thereof, obtained or obtainable by the process of any one of Items 1 to 19.

Item 56: A compound of formula [14]

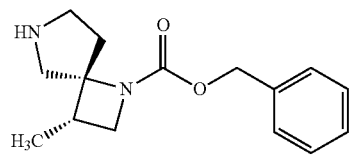

[14]

or its salt or a solvate thereof, obtained or obtainable by the process of any one of Items 26 to 43.

Item 57: A disodium salt dihydrate of the compound of formula [10]

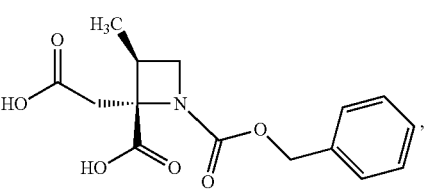

[10]

obtained or obtainable by the process of any one of Items 46 to 53.

Item 58: A compound of formula [11]

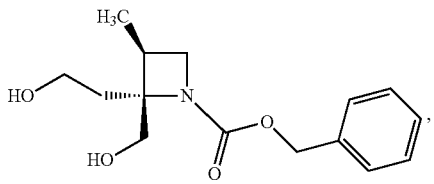

obtained or obtainable by the process of Item 54.

EXAMPLES

Specific processes for preparing compounds of the present invention, salts thereof, or solvates thereof are illustrated as examples hereinafter, but they should not be construed to be limited thereto.

In the crystallization steps in the preparations of Compound [5] (Example 1 Step-4, Example 16 Step 4), Compound [15] (Examples 11, 26), Compound [18](Example 14), and Compound A (i.e., Compound [19]) (Example 31), and the purification of Compound A (i.e., Compound [19]) (Examples 15, 30, 32), the corresponding seed crystals were used to facilitate the crystalizations, but it is possible to prepare crystals of each compound according to the processes described in the examples even without the corresponding seed crystals.

The abbreviations used herein mean the following compounds:
S-BAPO: (S)-2-(benzylamino) propan-1-ol
S-BBMO: tert-butyl (S)—N-benzyl-N-(1-hydroxypropan-2-yl)glycinate
R-BCAB: tert-butyl (R)—N-benzyl-N-(2-chloropropyl) glycinate S-MABB: tert-butyl (3S)-1-benzyl-3-methylazetidine-2-carboxylate
S-MABB-HC: tert-butyl (3S)-1-benzyl-3-methylazetidine-2-carboxylate hydrochloride S-MACB-HC: tert-butyl (3S)-3-methylazetidine-2-carboxylate hydrochloride
S-ZMAB: 1-benzyl 2-(tert-butyl) (3S)-3-methylazetidine-1,2-dicarboxylate
RS-ZMBB: 1-benzyl 2-(tert-butyl) (2R,3S)-2-(2-(tert-butoxy)-2-oxoethyl)-3-methylazetidine-1,2-dicarboxylate
RS-ZMAA: (2R,3S)-1-((benzyloxy)carbonyl)-2-(carboxymethyl)-3-methylazetidine-2-carboxylic acid
RS-ZMAA-DN 2H$_2$O: disodium (2R,3S)-1-((benzyloxy) carbonyl)-2-(carboxymethyl)-3-methylazetidine-2-carboxylate di-hydrate RS-ZMOO: benzyl (2R,3S)-2-(2-hydroxyethyl)-2-(hydroxymethyl)-3-methylazetidine-1-carboxylate
RS-ZMSS: benzyl (2R,3S)-3-methyl-2-(2-((methylsulfonyl) oxy)ethyl)-2-(((methylsulfonyl)oxy)methyl)azetidine-1-carboxylate
SR-ZMDB: benzyl (3S,4R)-6-benzyl-3-methyl-1,6-diazaspiro[3.4]octane-1-carboxylate
SR-MDOZ: benzyl (3S,4R)-3-methyl-1,6-diazaspiro[3.4] octane-1-carboxylate
SR-MDOZ-OX: benzyl (3S,4R)-3-methyl-1,6-diazaspiro [3.4]octane-1-carboxylate oxalate
SR-MDPZ: benzyl (3S,4R)-3-methyl-6-(7H-pyrrolo[2,3-d] pyrimidin-4-yl)-1,6-diazaspiro[3.4]octane-1-carboxylate
SR-MDOP: 4-[(3S,4R)-3-methyl-1,6-diazaspiro[3.4]-octan-6-yl]-7H-pyrrolo[2,3-d]pyrimidine Compound A: 3-[(3S,4R)-3-methyl-6-(7H-pyrrolo[2,3-d] pyrimidin-4-yl)-1,6-diazaspiro[3.4]octan-1-yl]-3-oxopropanenitrile
CPPY: 4-chloro-7H-pyrrolo[2,3-d]pyrimidine
DPCN: 1-cyanoacetyl-3,5-dimethyl-1H-pyrazole
TBBA: bromoacetic acid tert-butyl ester
THF: tetrahydrofuran.

The measuring instruments and measuring conditions used in the examples are as follows.

$^1$H-NMR spectra were analyzed in CDCl$_3$ or DMSO-d$_6$ using tetramethylsilane as an internal standard, and all δ values are shown as ppm. Unless otherwise indicated, a 400 MHz NMR instrument was used.

The symbols in the examples are meant as follows.
s: singlet
d: doublet
t: triplet
q: quartet
dd: double doublet
ddd: double double doublet
brs: broad singlet
m: multiplet
J: coupling constant
Ion contents in the samples were determined by averaging 3 observed data thereof.
Measuring instrument: Ion chromatograph LC-20 System (SHIMADZU)
Measuring condition: Electric-conductivity detector SHIMADZU CDD-10A VP
Column for anion analysis SHIMADZU SHIM-PAC IC-A3
Column for cation analysis SHIMADZU SHIM-PAC IC-C1
Water contents in the samples were measured by Karl Fischer's method. Measuring instrument: Karl Fischer Moisture Meter CA-06 (MITSUBISHI CHEMICAL)
Measuring Condition:
  Sample amount: about 20 mg
  Reagent:Anode solution Aquamicron AX (API Corporation)
  Catholyte Aquamicron CXU (API Corporation)
  X-ray diffractometry patterns of each sample were analyzed by powder X-ray diffractometry.
Measuring instrument: X'Pert Pro (SPECTRIS)
Measuring Condition:
  Anticathode: Cu
  Tube current and voltage of X-ray tube bulb: 45 kV, 40 mA
  Rotary speed of sample: each 1 sec.
  Incident-beam Soller slit: 0.02 rad
  Incident-beam Vertical divergence slit: 15 mm
  Incident-beam Divergence slit: Auto, Irradiation width 15 mm
  Incident-beam Scattering slit: 1°
  Diffracted-beam Filter: Nickel filter
  Diffracted-beam Soller slit: 0.02 rad
  Diffracted-beam Divergence slit: Auto, Irradiation width 15 mm
  Detector: X'Celerator
  Detector mode: Scanning
  Effective width of Detector: 2.122°
  Scan axis: Gonio.
  Scan mode: Continuing
  Scan range: 30-60°
  Time of unit step: 10 sec.
By elementary analysis, each weight % of carbon, hydrogen, and nitrogen in the samples was measured.

Example 1. Preparation of S-MABB-HC (Compound [5])

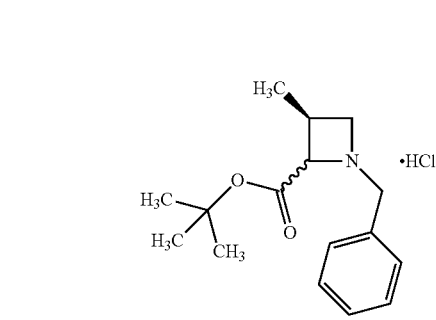

Step 1

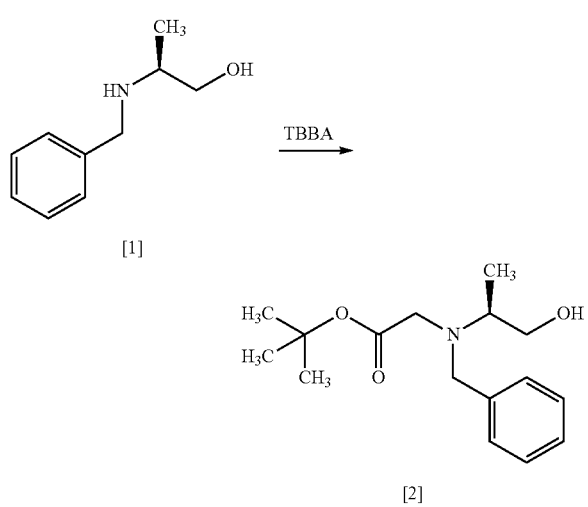

S-BAPO [1] (35.0 g, 212 mmol) was added to water (175 mL) at room temperature under nitrogen atmosphere. To the resulting suspension were added toluene (53 mL) and potassium carbonate (32.2 g, 233 mmol) at room temperature. To the resulting solution was added dropwise TBBA (434.4 g, 223 mmol) at room temperature, and then a dropping funnel used was washed with toluene (17 mL) and the washings were added to the reaction mixture. The reaction mixture was stirred at 65° C. for 21 hours, and then cooled to room temperature. After toluene (105 mL) was added to the reaction mixture and then the mixture was stirred, the organic layer was separated out. The organic layer was washed with water (175 mL), aqueous layer was removed, and then the solvent was removed out of the organic layer in vacuo. Toluene (105 mL) was added to the residue and the toluene solution was concentrated. The operation was repeated two more times to give a toluene solution of S-BBMO [2](74.0 g, 212 mmol in theory). The given toluene solution of S-BBMO was used in the next step, assuming that the yield was 100%.

A crude product of S-BBMO which was prepared by the same process was evaporated to dryness and then measured about NMR and MS.

$^1$H-NMR (DMSO-$d_6$) δ: 7.36-7.13 (5H, m), 4.26 (1H, dd, J=6.8, 3.9 Hz), 3.72 (2H, dd, J=14.2, 6.8 Hz), 3.47-3.38 (1H, m), 3.30-3.08 (3H, m), 2.79 (1H, sext, J=6.8 Hz), 1.35 (9H, s), 0.96 (3H, d, J=6.8 Hz).

MS: m/z=280 [M+H]$^+$

Step 2

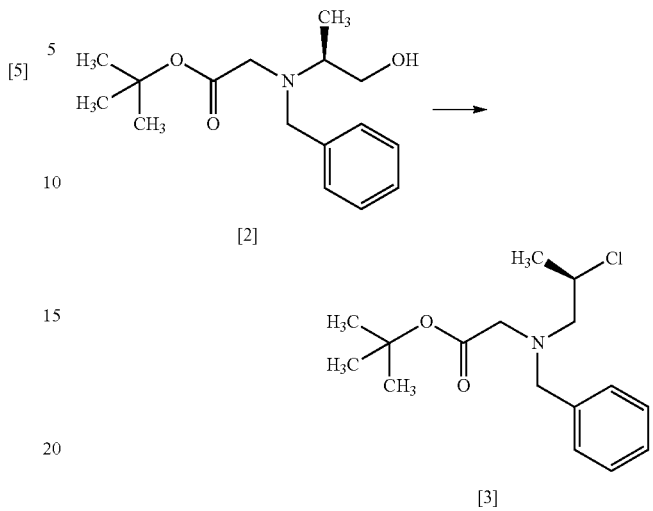

To the toluene solution of S-BBMO [2] (74.0 g, 212 mmol) were added toluene (200 mL), tetrahydrofuran (35 mL), and then triethylamine (25.7 g, 254 mmol) at room temperature under nitrogen atmosphere. To the mixture was added dropwise methanesulfonyl chloride (26.7 g, 233 mmol) at 0° C., and then a dropping funnel used was washed with toluene (10 mL) and the washings were added to the reaction mixture. The reaction mixture was stirred at room temperature for 2 hours and further at 65° C. for 22 hours, and then cooled to room temperature. After sodium bicarbonate water (105 mL) was added to the reaction mixture and then the mixture was stirred, the organic layer was separated out. The organic layer was washed with water (105 mL), aqueous layer was removed, and then the solvent was removed out of the organic layer in vacuo. Toluene (105 mL) was added to the residue, and the toluene solution was concentrated. The operation was repeated two more times to give a toluene solution of R-BCAB [3] (75.3 g, 212 mmol in theory). The given toluene solution of R-BCAB was used in the next step, assuming that the yield was 100%.

A crude product of R-BCAB which was prepared by the same process was evaporated to dryness and then measured about NMR and MS.

$^1$H-NMR (DMSO-$d_6$) δ: 7.28-7.11 (5H, m), 4.24-4.11 (1H, m), 3.80 (2H, d, J=3.6 Hz), 3.24 (2H, d, J=3.6 Hz), 2.98-2.78 (2H, m), 1.46-1.37 (12H, m).

MS: m/z=298 [M+H]$^+$

Step 3

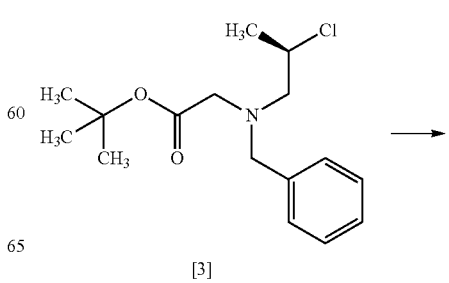

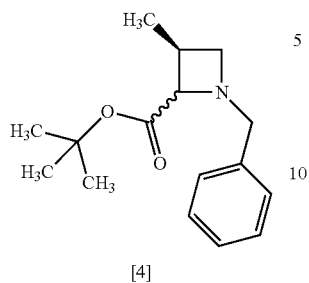

[4]

To the toluene solution of R-BCAB [3] (75.3 g, 212 mmol) were added tetrahydrofuran (88.0 mL) and 1,3-dimethyl-3,4,5,6-tetrahydro-2(1H)-pyrimidinone (42.0 mL) at room temperature under nitrogen atmosphere. To the resulting solution was added dropwise a solution of lithium bis(trimethylsilyl)amide/tetrahydrofuran (195 mL, 233 mmol) at 0° C., and then a dropping funnel used was washed with tetrahydrofuran (17.0 mL) and the washings were added to the reaction mixture. The reaction mixture was stirred at 0° C. for 1 hour, and then warmed to room temperature. After water (175 mL) and toluene (175 mL) were added to the reaction mixture and then the mixture was stirred, the organic layer was separated out. The resulting organic layer was washed with aqueous ammonium chloride (175 mL) and then water (175 mL), and the solvent was removed out of the organic layer in vacuo. Ethyl acetate (175 mL) was added to the residue and the ethyl acetate solution was concentrated. The operation was repeated two more times to give an ethyl acetate solution of S-MABB [4] (66.5 g, 212 mmol in theory). The given ethyl acetate solution of S-MABB was used in the next step, assuming that the yield was 100%.

A crude product of S-MABB which was prepared by the same process was evaporated to dryness and then measured about NMR and MS.

$^1$H-NMR (DMSO-d$_6$) δ: 7.28-7.25 (10H, m), 3.75 (1H, d, J=12.7 Hz), 3.68 (1H, d, J=1.4 Hz), 3.66 (1H, d, J=6.7 Hz), 3.46 (2H, d, J=12.7 Hz), 3.30-3.17 (2H, m), 2.95 (1H, dd, J=6.2, 1.2 Hz), 2.77 (1H, dd, J=6.1, 2.2 Hz), 2.65-2.55 (1H, m), 2.48-2.40 (2H, m), 1.35 (9H, s), 1.35 (9H, s), 1.12 (3H, d, J=7.2 Hz), 1.09 (3H, d, J=6.2 Hz).

MS: m/z=262 [M+H]$^+$

Step 4

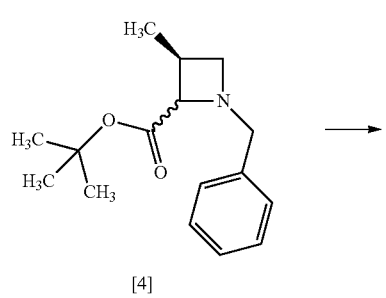

[4]

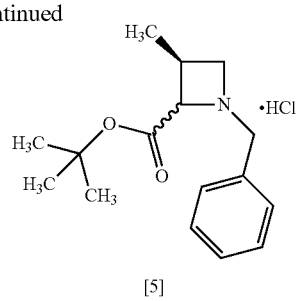

[5]

To the ethyl acetate solution of S-MABB [4] (66.5 g, 212 mmol in theory) were added ethyl acetate (175 mL) and active carbon (3.5 g) under nitrogen atmosphere, and then the mixture was stirred at room temperature for 2 hours. The active carbon was removed by filtration, and the residue on the filter was washed with ethyl acetate (175 mL). The washings were added to the filtrate. To the solution was added S-MABB-HC crystal (17.5 mg) that was prepared according to the method described herein at 0° C., and then 4 M hydrogen chloride/ethyl acetate (53.0 mL, 212 mmol) was dropped thereto at 0° C. The reaction mixture was stirred at 0° C. for 17 hours, and then the precipitated solid was collected on a filter, and washed with ethyl acetate (70 mL). The resulting wet solid was dried in vacuo to give S-MABB-HC [5](48.3 g, 162 mmol, yield: 76.4%).

S-MABB-HC which was prepared by the same process was measured about NMR, MS, and Cl-content.

$^1$H-NMR (DMSO-d$_6$) δ: 11.08 (1H, br s), 10.94 (1H, br s), 7.52-7.42 (10H, m), 5.34 (1H, t, J=8.4 Hz), 4.90 (1H, br s), 4.45-4.10 (5H, m), 3.92-3.49 (3H, br m), 3.10-2.73 (2H, br m), 1.35 (9H, s), 1.29 (9H, s), 1.24 (3H, d, J=6.7 Hz), 1.17 (3H, d, J=7.4 Hz).

MS: m/z=262 [M+H-HCl]

Cl content (ion chromatography): 11.9% (in theory: 11.9%)

Example 2. Preparation of S-MACB-HC (Compound [6])

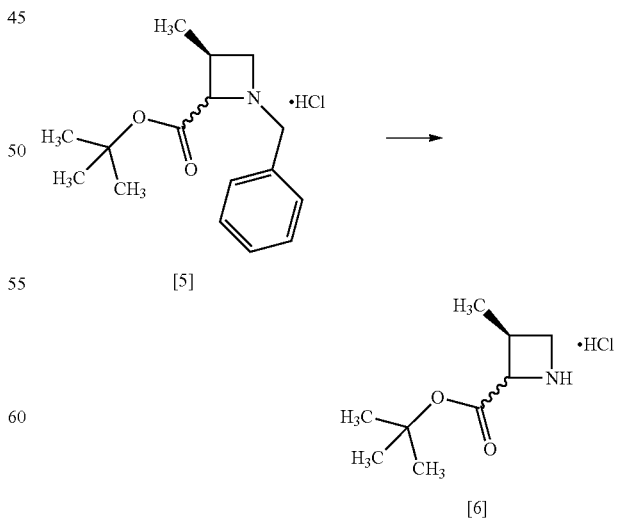

To a solution of S-MABB-HC [5] (5.0 g, 16.8 mmol) in methanol (15.0 mL) was added 5% palladium carbon (made by Kawaken Fine Chemicals Co., Ltd., PH type, 54.1% water-content 1.0 g) at room temperature under nitrogen atmosphere. The reaction vessel was filled with hydrogen, the reaction mixture was stirred at hydrogen pressure of 0.4 MPa at room temperature for 12 hours, the hydrogen in the reaction vessel was replaced with nitrogen, and then the 5% palladium carbon was removed by filtration. The reaction vessel and the 5% palladium carbon were washed with methanol (10 mL). The washings were added to the filtrate to give a methanol solution of S-MACB-HC [6] (24.8 g, 16.8 mmol in theory). The given methanol solution of S-MACB-HC was used in the next step, assuming that the yield was 100%.

A crude product of S-MACB-HC which was prepared by the same process was evaporated to dryness and then measured about NMR and MS.

$^1$H-NMR (DMSO-$d_6$) δ: 9.60 (br s, 1H), 4.97 (d, 1H, J=9.2 Hz), 4.61 (d, 1H, J=8.4 Hz), 4.01 (dd, 1H, J=10.0, 8.4 Hz), 3.78-3.74 (m, 1H), 3.54 (dd, 1H, J=9.6, 8.4 Hz), 3.35 (dd, 1H, J=10.0, 6.0 Hz), 3.15-3.03 (m, 1H), 3.00-2.88 (m, 1H), 1.49 (s, 9H), 1.47 (s, 9H), 1.22 (d, 3H, J=6.8 Hz), 1.14 (d, 3H, J=7.2 Hz).

MS: m/z=172 [M+H]$^+$ (free form)

Example 3. Preparation of S-ZMAB (Compound [7])

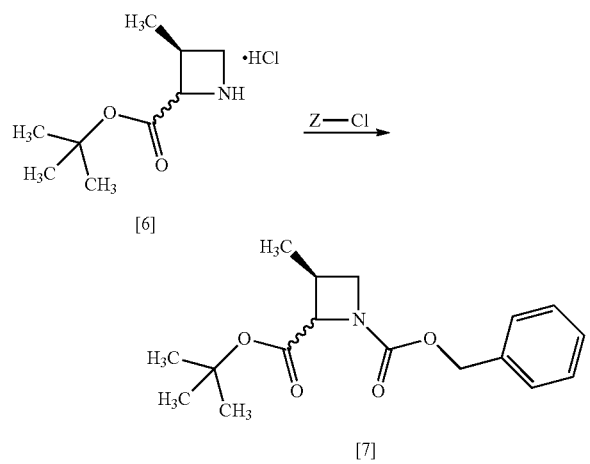

To the methanol solution of S-MACB-HC [6] (24.8 g, 16.8 mmol in theory) was added dropwise N,N-diisopropylethylamine (4.8 g, 36.9 mmol) at room temperature under nitrogen atmosphere, and then a dropping funnel used was washed with tetrahydrofuran (2.5 mL) and the washings were added to the reaction mixture. To the resulting reaction mixture was added dropwise benzyl chloroformate (3.0 g, 17.6 mmol) at 0° C., and then a dropping funnel used was washed with tetrahydrofuran (2.5 mL) and the washings were added to the reaction mixture. The reaction mixture was stirred at 0° C. for 1 hour, and then the solvent was removed in vacuo. After toluene (25.0 mL) and an aqueous solution of citric acid (25.0 mL) was added to the residue and then the mixture was stirred, the organic layer was separated out. The resulting organic layer was washed with sodium bicarbonate water (25.0 mL) and then water (25.0 mL), and the solvent in the organic layer was removed out of the organic layer in vacuo. Toluene (15.0 mL) was added to the residue and the toluene solution was concentrated. The operation was repeated one more time to give a toluene solution of S-ZMAB [7] (6.9 g, 16.8 mmol in theory). The given toluene solution of S-ZMAB was used in the next step, assuming that the yield was 100%.

A crude product of S-ZMAB which was prepared by the same process was evaporated to dryness and then measured about NMR and MS.

$^1$H-NMR (CDCl$_3$) δ: 7.38-7.28 (m, 10H), 5.16-5.04 (m, 4H), 4.60 (d, 1H, J=9.2 Hz), 4.18-4.12 (m, 2H), 4.04 (t, 1H, J=8.6 Hz), 3.66 (dd, 1H, J=7.6, 7.2 Hz), 3.50 (dd, 1H, J=8.0, 5.2 Hz), 3.05-2.94 (m, 1H), 2.60-2.50 (m, 1H), 1.43 (br s, 18H), 1.33 (d, 3H, J=6.5 Hz), 1.15 (d, 3H, J=7.2 Hz).

MS: m/z=328 [M+Na]$^+$

Example 4. Preparation of RS-ZMBB (Compound [8])

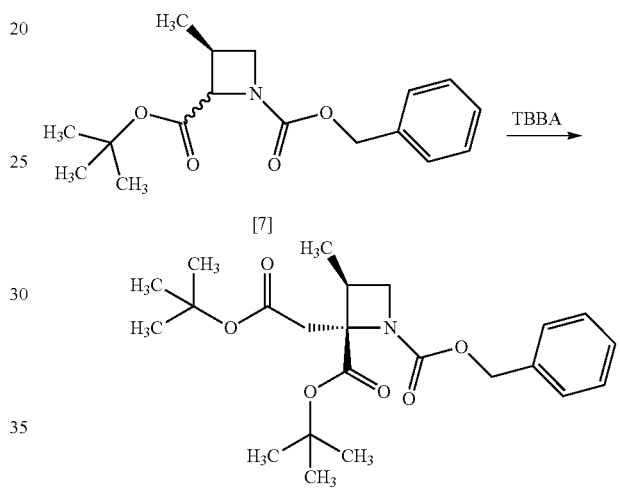

To the toluene solution of S-ZMAB [7] (6.9 g, 16.8 mmol) was added tetrahydrofuran (15.0 mL) at room temperature under nitrogen atmosphere. A solution of lithium bis(trimethylsilyl)amide/tetrahydrofuran (14.7 mL, 17.6 mmol) was added dropwise to the toluene solution at −70° C. The used dropping funnel was washed with tetrahydrofuran (2.5 mL) and the washings were added to the reaction mixture. The reaction mixture was stirred at −70° C. for 6 hours, and then a solution of TBBA (3.4 g, 17.6 mmol) in tetrahydrofuran (2.5 mL) was added dropwise to the reaction mixture at −70° C. The used dropping funnel was washed with tetrahydrofuran (2.5 mL) and the washings were added to the reaction mixture. The reaction mixture was stirred at −70° C. for 1 hour, and then warmed to room temperature. To the reaction mixture were added an aqueous ammonium chloride (25 mL) and toluene (25 mL) and then the mixture was stirred, the organic layer was separated out. The resulting organic layer was washed with an aqueous solution of citric acid (25 mL, ×2), sodium bicarbonate water (25 mL), and then water (25 mL), and then the solvent was removed out of the organic layer in vacuo. Acetonitrile (15 mL) was added to the residue and the acetonitrile solution was concentrated. The operation was repeated two more times. Acetonitrile (15 mL) and active carbon (0.25 g) were added to the residue, the mixture was stirred at room temperature for 2 hours. The active carbon was removed by filtration, and the reaction vessel and the residue on the filter was washed with acetonitrile (10 mL). The washings were added to the filtration, and then the filtration was concentrated in vacuo to give an acetonitrile solution of RS-ZMBB [8] (13.2 g, 16.8 mmol in theory). The given acetonitrile solution of RS-ZMBB was used in the next step, assuming that the yield was 100%.

A crude product of RS-ZMBB which was prepared by the same process was evaporated to dryness and then measured about NMR and MS.

$^1$H-NMR (DMSO-d$_6$) δ: 7.38-7.29 (m, 5H), 5.09-4.96 (m, 2H), 3.91 (t, 0.4H, J=8.0 Hz), 3.79 (t, 0.6H, J=8.0 Hz), 3.55 (t, 0.4H, J=7.2 Hz), 3.46 (t, 0.6H, J=7.5 Hz), 3.14-3.04 (m, 1H), 2.83-2.72 (m, 2H), 1.38 (br s, 9H), 1.37 (br s, 3.6H), 1.34 (br s, 5.4H), 1.12-1.09 (m, 3H).

MS: m/z=420 [M+H]$^+$

Example 5. Preparation of RS-ZMAA-DN.2H$_2$O (Compound [9])

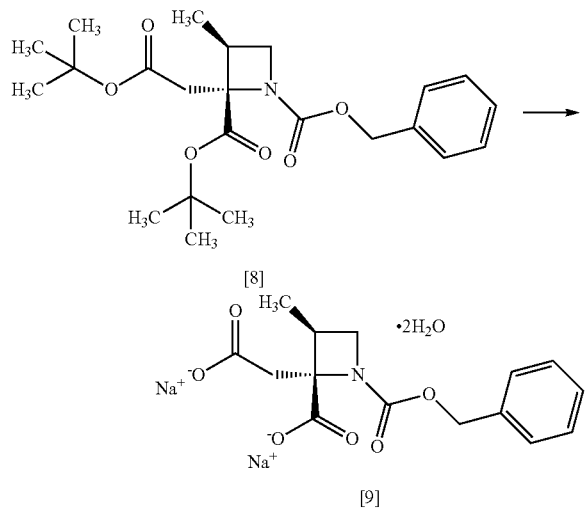

To the acetonitrile solution of RS-ZMBB [8] (13.2 g, 16.8 mmol in theory) was added acetonitrile (15 mL) at room temperature under nitrogen atmosphere. p-Toluenesulfonic acid mono-hydrate (6.4 g, 33.6 mmol) was added to the solution at room temperature. The reaction mixture was stirred at 50° C. for 12 hours, and then cooled to room temperature, and water (7.5 mL) was added dropwise to the reaction mixture. The reaction mixture was cooled to 0° C., and then 4 mol/L aqueous sodium hydroxide (17.6 mL, 70.5 mmol) was added dropwise thereto. After stirring the reaction mixture at room temperature for 1 hour, acetonitrile (75 mL) was added dropwise thereto at room temperature, and the reaction mixture was stirred for 3 hours. The precipitated solid was collected on a filter, and washed with a mixture of acetonitrile:water=4:1 (10 mL) and then acetonitrile (10 mL). The resulting wet solid was dried in vacuo to give RS-ZMAA-DN.2H$_2$O [9] (5.2 g, 13.4 mmol, yield: 85.4%).

RS-ZMAA-DN.2H$_2$O which was prepared by the same process was measured about NMR, MS, Na-content, and water-content.

$^1$H-NMR (DMSO-d$_6$) δ: 7.32-7.22 (m, 5H), 4.97 (d, 1H, J=12.7 Hz), 4.84 (d, 1H, J=12.7 Hz), 3.79 (t, 1H, J=8.0 Hz), 3.29 (d, 1H, J=14.8 Hz), 3.16-3.12 (m, 1H), 2.17-2.09 (m, 2H), 1.07 (d, 3H, J=6.9 Hz).

MS: m/z=352 [M+H]+(anhydrate)

Na content (ion chromatography): 13.3% (after correction of water content)(13.1% in theory)

Water content (Karl Fischer's method): 9.8% (9.3% in theory)

Using RS-ZMAA-DN.2H$_2$O which was prepared by the same method, the diffraction angle 2θ and diffraction intensity were measured by the powder X-ray diffractometry. The measured spectra are shown in FIG. 1.

Each peak in FIG. 1 is shown in the following table.

TABLE 1

| Diffraction angle [2θ (°)] | Relative intensity [%] | Diffraction intensity [cps] |
| --- | --- | --- |
| 4.9152 | 100.00 | 16523.88 |
| 12.3356 | 38.97 | 6440.13 |
| 14.1756 | 1.64 | 271.24 |
| 14.5417 | 3.88 | 641.71 |
| 15.0030 | 17.48 | 2888.94 |
| 15.4626 | 5.64 | 931.73 |
| 16.4596 | 5.21 | 860.16 |
| 18.1441 | 4.89 | 808.32 |
| 18.4431 | 10.79 | 1782.20 |
| 18.6450 | 12.75 | 2107.32 |
| 19.1901 | 18.89 | 3121.57 |
| 20.0093 | 8.79 | 1453.05 |
| 21.3492 | 14.85 | 2454.02 |
| 22.7211 | 17.10 | 2824.96 |
| 23.2533 | 4.42 | 730.11 |
| 24.7745 | 4.15 | 685.90 |

The crystallizing step of RS-ZMAA-DN.2H$_2$O (Compound [9]) is useful for removing its diastereomer, SS-ZMAA. The diastereomer ratio in Example 4 (Preparation of RS-ZMBB (Compound [8])) was [RS-ZMBB/SS-ZMBB=99.13%/0.87% (HPLC Area percentage)], while the diastereomer ratio in Example 6 (Preparation of RS-ZMAA (Compound [10])) prepared via the crystallizing step of Compound [9] was [RS-ZMAA/SS-ZMAA=99.98%/0.02% (HPLC Area percentage)], as shown in the following table.

TABLE 2

| Example 4 ZMBB (HPLC area ratio) | | Example 6 ZMAA (HPLC area ratio) | |
| --- | --- | --- | --- |
| RS | SS | RS | SS |
| 99.13% | 0.87% | 99.98% | 0.02% |

Example 6. Preparation of RS-ZMAA (Compound [10])

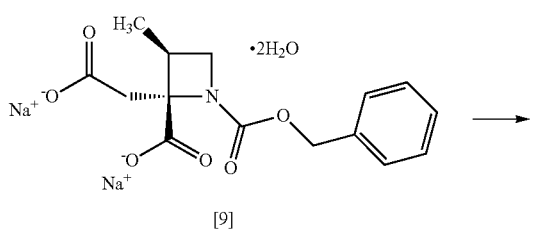

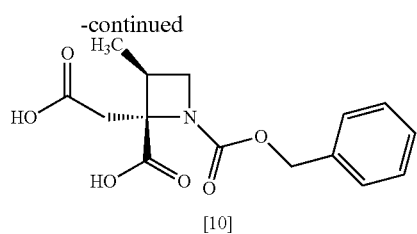

[10]

To 1 mol/L hydrochloric acid (180 mL) were added RS-ZMAA-DN.2H$_2$O [9](30 g, 77.5 mmol) and acetonitrile (60 mL), and the mixture was stirred at room temperature for about 15 minutes. After ethyl acetate (240 mL) was added to the reaction mixture and then the mixture was stirred, the organic layer was separated out. The organic layer was washed with 10% brine (60 mL×2). The organic layer was stirred with magnesium sulfate (6 g), the magnesium sulfate was removed by filtration, and the residue on the filter was washed with ethyl acetate (60 mL). The filtrate and the washings are combined, and the solvent was removed out in vacuo. Tetrahydrofuran (240 mL) was added to the residue and the tetrahydrofuran solution was concentrated. The operation was repeated two more times. Tetrahydrofuran (60 mL) was added to the residue to give a tetrahydrofuran solution of RS-ZMAA [10]. The given tetrahydrofuran solution of RS-ZMAA was used in the next step, assuming that the yield was 100%.

RS-ZMAA which was prepared by the same process was measured about NMR and MS.

$^1$H-NMR (DMSO-D$_6$) δ: 7.35-7.28 (m, 5H), 5.06-4.94 (m, 2H), 3.86 (dt, 1H, J=48.4, 7.9 Hz), 3.50 (dt, 1H, J=37.9, 7.4 Hz), 3.16-3.02 (br m, 1H), 2.91-2.77 (br m, 2H), 1.08 (d, 3H, J=6.9 Hz)

MS: m/z=308 [M+H]$^+$

Example 7. Preparation of RS-ZMOO (Compound [11])

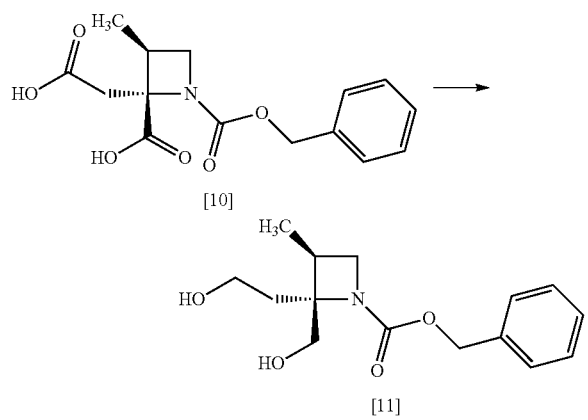

To the tetrahydrofuran solution of RS-ZMAA [10] (25.8 mmol in theory) was added tetrahydrofuran (50 mL) under nitrogen atmosphere. Boron trifluoride etherate complex (4.40 g) was added dropwise thereto at 0° C. to 5° C. The used dropping funnel was washed with tetrahydrofuran (5 mL) and the washings were added to the reaction mixture. To the reaction mixture was added dropwise 1.2 mol/L borane-tetrahydrofuran complex (43.0 mL) at 0° C. to 5° C., and the reaction mixture was stirred at 0° C. to 5° C. for about 30 minutes, and then further stirred at room temperature overnight. To the reaction mixture was added dropwise 1.2 mol/L borane-tetrahydrofuran complex (21.1 mL) at 0° C. to 5° C., and then the reaction mixture was stirred at room temperature overnight. After stirring, water (40 mL) was added dropwise to the reaction mixture at 0° C. to 15° C. To the reaction mixture was added sodium bicarbonate (5.42 g) at 0° C. to 15° C. The sodium bicarbonate left in the vessel was washed with water (10 mL), and the washings were added to the reaction mixture. The reaction mixture was stirred at room temperature for 2 hours, and then toluene (50 mL) was added thereto and the reaction mixture was further stirred. The organic layer was separated out. The resulting organic layer was washed with 10% brine (20 mL×1), a mixture (×3) of 5% sodium bicarbonate water (20 mL) and 10% brine (20 mL), a mixture (×1) of 5% aqueous potassium hydrogensulfate (10 mL) and 10% brine (10 mL), and then 10% brine (20 mL×2). The organic layer was stirred with magnesium sulfate (8.9 g), the magnesium sulfate was removed by filtration, and the residue on the filter was washed with toluene (20 mL). The washings were added to the filtration, and then the filtrate was concentrated in vacuo. To the concentrated residue was added toluene (80 mL). The solution was concentrated in vacuo, and toluene (15 mL) was added thereto to give a toluene solution of RS-ZMOO [11]. The given toluene solution of RS-ZMOO was used in the next step, assuming that the yield was 100%.

RS-ZMOO which was prepared by the same process was measured about NMR and MS.

$^1$H-NMR (CDCl$_3$) δ: 7.39-7.30 (m, 5H), 5.10 (s, 2H), 4.15-4.01 (br m, 2H), 3.83-3.73 (br m, 3H), 3.48 (dd, 1H, J=8.3, 6.4 Hz), 2.59-2.50 (br m, 1H), 2.46-2.40 (br m, 1H), 2.07-1.99 (m, 1H), 1.14 (d, 3H, J=7.2 Hz)

MS: m/z=280 [M+H]$^+$

Example 8. Preparation of RS-ZMSS (Compound [12])

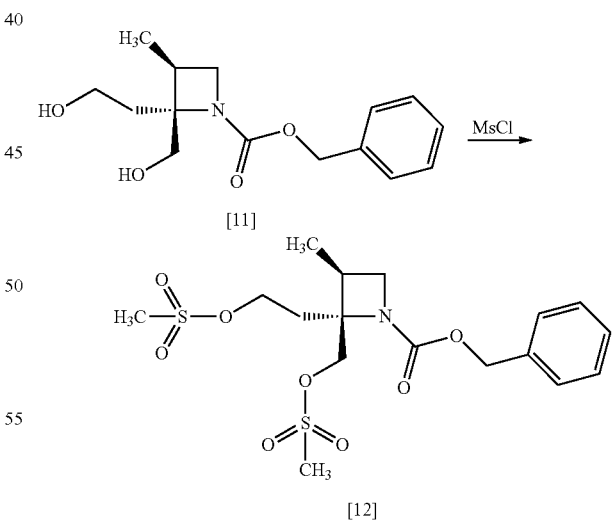

To the toluene solution of RS-ZMOO [11] (23.7 mmol in theory) was added toluene (55 mL) under nitrogen atmosphere. And, triethylamine (5.27 g) was added dropwise thereto at −10° C. to 10° C., and a dropping funnel used was washed with toluene (1.8 mL) and the washings were added to the reaction mixture. To this reaction mixture was added dropwise methanesulfonyl chloride (5.69 g) at −10° C. to 10° C., and then a dropping funnel used was washed with toluene (1.8 mL) and the washings were added to the reaction mixture. The reaction mixture was stirred at 0° C. to 10° C. for about 2 hours, and then water (28 mL) was added dropwise thereto at 0° C. to 20° C. The reaction mixture was stirred at 0° C. to 20° C. for about 30 minutes, and then, the organic layer was separated out. The resulting organic layer was washed twice with 10% brine (18 mL). The organic layer was stirred with magnesium sulfate (2.75 g), the magnesium sulfate was removed by filtration, and the residue on the filter was washed with toluene (18 mL). The washings were added to the filtrate, and then the solvent was removed from the filtrate in vacuo. To the concentrated residue was added toluene up to 18 mL to give a toluene solution of RS-ZMSS [12]. The given toluene solution of RS-ZMSS was used in the next step, assuming that the yield was 100%.

RS-ZMSS which was prepared by the same process was measured about NMR and MS.

$^1$H-NMR (DMSO-D$_6$) δ: 7.37-7.27 (br m, 5H), 5.10-4.98 (m, 2H), 4.58-4.22 (br m, 4H), 3.84 (dt, 1H, J=45.6, 8.1 Hz), 3.48-3.33 (br m, 1H), 3.17-3.10 (m, 6H), 2.81-2.74 (br m, 1H), 2.22-2.12 (m, 2H)

MS: m/z=436 [M+H]$^+$

Example 9. Preparation of SR-ZMDB (Compound [13])

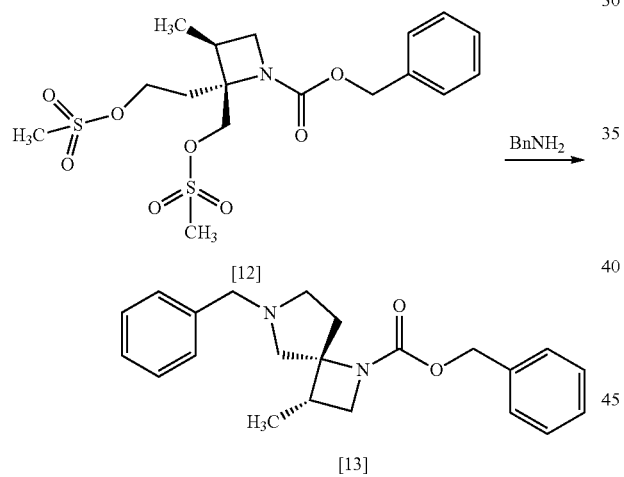

To a toluene solution of RS-ZMSS [12] (23.7 mmol in theory) was added toluene (55 mL) under nitrogen atmosphere. And, benzylamine (17.8 g) was added dropwise thereto at room temperature, and a dropping funnel used was washed with toluene (9.2 mL) and the washings were added to the reaction mixture. The reaction mixture was stirred at room temperature for about 1 hour, at 55° C. to 65° C. for about 3 hours, and then at 70° C. to 80° C. for 6 hours. After the reaction mixture was cooled to room temperature, 10% NaCl (28 mL) was added dropwise thereto, and the reaction mixture was stirred at room temperature for about 30 minutes. After toluene (37 mL) was added to the reaction mixture and then the mixture was stirred, the organic layer was separated out. The resulting organic layer was washed with a mixture (×2) of 10% brine (18 mL) and acetic acid (2.84 g), and then 10% brine (11 mL, ×1). The solvent of the organic layer was removed in vacuo to a half volume, and acetic anhydride (1.45 g) was added to the concentrated residue at room temperature. The mixture was stirred for about 3 hours. To the reaction mixture were added dropwise a solution of potassium hydrogensulfate (3.87 g) and water (92 mL) at room temperature. The reaction mixture was stirred, and then the aqueous layer was separated out. The resulting aqueous layer was washed with toluene (18 mL), and toluene (73 mL) and then sodium bicarbonate (6.56 g) were added to the aqueous layer at room temperature, and the mixture was stirred. The organic layer was separated out, and washed with 10% brine (11 mL). The organic layer was stirred with magnesium sulfate (2.75 g), the magnesium sulfate was removed by filtration. The residue on the filter was washed with toluene (18 mL), and the washings were added to the filtrate, and then the filtrate was concentrated in vacuo. Toluene (44 mL) was added to the concentrated residue to give a toluene solution of SR-ZMDB [13]. The given toluene solution of SR-ZMDB was used in the next step, assuming that the yield was 100%.

$^1$H-NMR (CDCl$_3$) δ: 7.35-7.20 (m, 10H), 5.08 (d, 2H, J=23.6 Hz), 3.94 (q, 1H, J=7.9 Hz), 3.73-3.42 (br m, 2H), 3.30-3.23 (m, 1H), 3.05 (dd, 1H, J=19.7, 9.5 Hz), 2.79 (dt, 1H, J=69.6, 6.1 Hz), 2.57-2.32 (br m, 4H), 1.96-1.89 (m, 1H), 1.09 (d, 3H, J=6.9 Hz)

MS: m/z=351 [M+H]$^+$

Example 10. Preparation of SR-MDOZ (Compound [14])

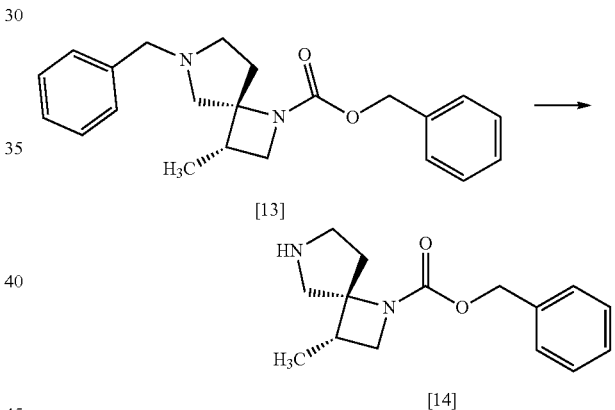

To a solution of 1-chloroethyl chloroformate (3.72 g) in toluene (28 mL) was added dropwise the toluene solution of SR-ZMDB [13] (23.7 mmol in theory) at 0° C. to 10° C. under nitrogen atmosphere, and then a dropping funnel used was washed with toluene (4.6 mL) and the washings were added to the reaction mixture. To the reaction mixture was added triethylamine (718 mg) at 0° C. to 10° C., and the reaction mixture was stirred at 15° C. to 25° C. for about 2 hours. Then, methyl alcohol (46 mL) was added to the reaction mixture, and the mixture was stirred at 50° C. to 60° for additional about 2 hours. The solvent of the reaction mixture was removed in vacuo to a volume of about less than 37 mL. To the concentrated residue was added dropwise 2 mol/L hydrochloric acid (46 mL) at 15° C. to 20° C., and the mixture was stirred, and the aqueous layer was separated out. The resulting aqueous layer was washed with toluene (28 mL, ×2). To the aqueous layer were added 20% brine (46 mL) and tetrahydrofuran (92 mL), and then 8 mol/L aqueous sodium hydroxide (18 mL) was added dropwise thereto at 0° C. to 10° C. The organic layer was separated out from the reaction mixture, washed with 20% brine (18 mL, ×2), and then the solvent of the organic layer was removed in vacuo. To the concentrated residue was added tetrahydrofuran (92 mL), and the solution was concentrated in vacuo. The operation was repeated one more time. The concentrated residue was dissolved in tetrahydrofuran (92 mL). The solution was stirred with magnesium sulfate (2.75 g), and the magnesium sulfate was removed by filtration. The residue on the filter was washed with tetrahydrofuran (28 mL), the washings were added to the filtrate, and the filtrate was concentrated in vacuo. The volume of the concentrated residue was adjusted to about 20 mL with tetrahydrofuran to give a tetrahydrofuran solution of SR-MDOZ [14] (net weight: 4.01 g, 15.4 mol, yield: 65.0%).

SR-MDOZ which was prepared by the same process was evaporated to dryness and then measured about NMR and MS.

$^1$H-NMR (CDCl$_3$) δ: 7.37-7.28 (m, 5H), 5.08 (dd, 2H, J=16.8, 12.8 Hz), 4.00 (dd, 1H, J=17.1, 8.3 Hz), 3.40-3.31 (m, 1H), 3.24 (d, 1H, J=12.7 Hz), 3.00 (dd, 1H, J=54.9, 12.4 Hz), 2.87-2.57 (m, 3H), 2.47-2.27 (m, 1H), 1.91-1.80 (m, 1H), 1.14 (d, 3H, J=7.2 Hz)

MS: m/z=261 [M+H]$^+$

Example 11. Preparation of SR-MDOZ-OX(Compound [15])

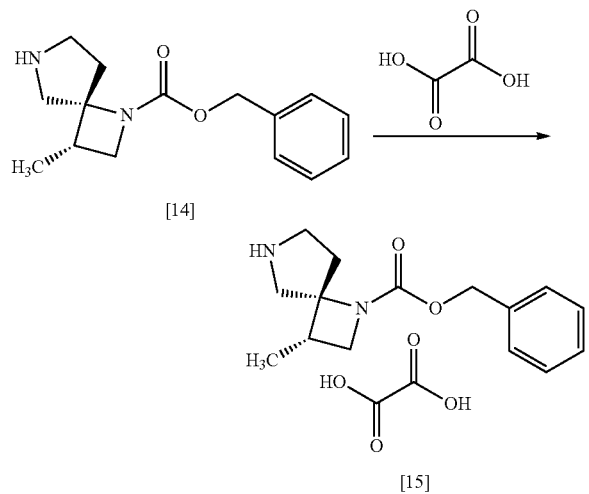

Under nitrogen atmosphere, oxalic acid (761 mg) was dissolved in tetrahydrofuran (40 mL), and the tetrahydrofuran solution of SR-MDOZ [14] (3.84 mmol in theory) was added dropwise to the solution of oxalic acid at room temperature. To the solution was added SR-MDOZ-OX crystal (1 mg) that was prepared according to the method described herein at room temperature, and the mixture was stirred at room temperature for about 3.5 hours to precipitate the crystal. To the slurry solution was added dropwise the tetrahydrofuran solution of SR-MDOZ (3.84 mmol) at room temperature, and the mixture was stirred at room temperature for about 1 hour. The slurry solution was heated, and stirred at 50° C. to 60° C. for about 2 hours, and then stirred at room temperature overnight. The slurry solution was filtrated, and the wet crystal on the filter was washed with tetrahydrofuran (10 mL), dried in vacuo to give SR-MDOZ-OX [15] (2.32 g, 6.62 mol, yield: 86.2%).

SR-MDOZ-OX which was prepared by the same process was measured about NMR, MS, and elementary analysis.

$^1$H-NMR (DMSO-D$_6$) δ: 7.37-7.30 (m, 5H), 5.15-5.01 (m, 2H), 3.92 (dt, 1H, J=43.5, 8.4 Hz), 3.48-3.12 (br m, 5H), 2.67-2.56 (m, 1H), 2.46-2.35 (m, 1H), 2.12-2.05 (m, 1H), 1.13 (d, 3H, J=6.9 Hz)

MS: m/z=261 [M+H]$^+$ elementary analysis: C, 58.4 wt %, H, 6.4 wt %, N, 7.9% wt % (theoretically, C, 58.3 wt %, H, 6.3 wt %, N, 8.0 wt %).

Using SR-MDOZ-OX which was prepared by the same method, the diffraction angle 2θ and diffraction intensity were measured by the powder X-ray diffractometry. The measured spectra are shown in FIG. 2.

Each peak in FIG. 2 is shown in the following table.

TABLE 3

| Diffraction angle [2θ (°)] | Relative intensity [%] | Diffraction intensity [cps] |
| --- | --- | --- |
| 3.2617 | 24.21 | 979.85 |
| 6.5311 | 100.00 | 4046.93 |
| 7.7614 | 13.30 | 538.07 |
| 8.2590 | 9.96 | 402.92 |
| 9.0278 | 98.44 | 3983.61 |
| 10.0085 | 10.87 | 440.07 |
| 11.1466 | 10.08 | 407.83 |
| 12.3994 | 3.76 | 152.19 |
| 13.0651 | 18.29 | 740.35 |
| 13.7251 | 18.17 | 735.28 |
| 15.1195 | 35.41 | 1433.19 |
| 15.9690 | 54.25 | 2195.26 |
| 16.3494 | 20.59 | 833.17 |
| 16.5751 | 17.44 | 705.96 |
| 17.0079 | 21.04 | 851.41 |
| 17.5271 | 49.16 | 1989.52 |
| 18.1061 | 96.32 | 3897.86 |
| 18.8710 | 18.19 | 736.31 |
| 19.5546 | 27.45 | 1110.80 |
| 20.0812 | 59.98 | 2427.38 |
| 20.9359 | 16.04 | 648.93 |
| 21.1980 | 17.41 | 704.71 |
| 21.9447 | 58.27 | 2358.05 |
| 22.6466 | 30.31 | 1226.73 |
| 22.9387 | 18.65 | 754.67 |
| 23.6203 | 29.96 | 1212.36 |
| 24.3811 | 8.21 | 332.06 |

The crystallizing step of SR-MDOZ is useful for enhancing the purity of SR-MDOZ. Namely, the HPLC area percentage of SR-MDOZ in Example 10 was 91.4%, while the HPLC area percentage of SR-MDOZ-OX prepared via the crystallizing step in Example 11 was 99.7%.

The measuring instrument and condition in HPLC are as follows.

Measuring instrument: Alliance System (Waters)

Measuring Condition:

Column: AtlantisT3: 5 μm 250×4.6 mm (Waters)

Column temperature: 40° C.

Flow rate: 0.8 mL/min.

Analytic time: 45 min.

Detector wave length: UV (210 nm)

Mobile phase A: 5 mM phosphate buffer (Phosphate Buffere)

0.39 g of Sodium dihydrogenphosphate di-hydrate and 0.89 g of disodium hydrogenphosphate 12-hydrate are dissolved in 1 L of water. The solution is filtrated with a filter (0.45 μm) and degassed to be used.

Mobile phase B: acetonitrile

Gradient condition:

0 min: B 20%, A 80%

5 min: B 20%, A 80%

20 min: B 80%, A 20%

35 min: B 80%, A 20%

36 min: B 20%, A 80%

45 min: stop

Each retention time of the subject compounds in the above HPLC measuring condition was about 16 minutes for SR-MDOZ and about 2.8 minutes for oxalic acid.

The results of the HPLC analysis with SR-MDOZ in Example 10 are shown in FIG. 3 and the following table.

TABLE 4

|  | Retention time (min.) | Area (μV sec.) | Height (μV) | % Area | Division type |
|---|---|---|---|---|---|
| 1 | 3.055 | 6080 | 1367 | 0.0661 | bb |
| 2 | 5.477 | 10401 | 1204 | 0.1130 | bb |
| 3 | 8.605 | 4401 | 517 | 0.0478 | bb |
| 4 | 12.454 | 159893 | 20953 | 1.7372 | bb |
| 5 | 13.255 | 9220 | 1148 | 0.1002 | bb |
| 6 | 14.790 | 8321 | 984 | 0.0904 | bb |
| 7 | 16.027 | 8408397 | 494224 | 91.3573 | bb |
| 8 | 18.956 | 2637 | 446 | 0.0287 | bb |
| 9 | 19.757 | 4332 | 479 | 0.0471 | bb |
| 10 | 22.533 | 3339 | 482 | 0.0363 | bb |
| 11 | 24.152 | 5010 | 504 | 0.0544 | bb |
| 12 | 26.487 | 183767 | 20491 | 1.9966 | bv |
| 13 | 26.913 | 73190 | 5699 | 0.7952 | vb |
| 14 | 33.958 | 324866 | 20737 | 3.5297 | bb |

The results of the HPLC analysis with SR-MDOZ-OX prepared via the crystallizing step in Example 11 are shown in FIG. 4 and the following table.

TABLE 5

|  | Retention time (min.) | Area (μV sec.) | Height (μV) | % Area | Division type |
|---|---|---|---|---|---|
| 1 | 2.769 | 496262 | 77347 | 7.1696 | bv |
| 2 | 3.026 | 3074 | 707 | 0.0444 | vb |
| 3 | 5.464 | 1009 | 131 | 0.0146 | bb |
| 4 | 12.399 | 1402 | 170 | 0.0203 | bb |
| 5 | 16.237 | 6406900 | 278383 | 92.5617 | bb |
| 6 | 19.762 | 4691 | 382 | 0.0678 | bb |
| 7 | 22.492 | 1593 | 145 | 0.0230 | bb |
| 8 | 26.478 | 5232 | 420 | 0.0756 | bb |
| 9 | 33.867 | 1596 | 110 | 0.0231 | bb |

To a solution of SR-MDOZ (1.000 g, 3.841 mmol) in ethyl acetate (4 mL) and ethyl alcohol (1 mL) was added L-tartaric acid (605 mg) at room temperature. The reaction mixture was stirred for about 2 hours, the precipitated crystal was collected on a filter, and washed with ethyl acetate (2 mL), and dried at 40° C. in vacuo to give SR-MDOZ mono-L-tartrate (1.418 g, 3.455 mmol, yield: 90.0%).

To a solution of SR-MDOZ (500 mg, 1.92 mmol) in ethyl acetate (2 mL) and ethyl alcohol (0.5 mL) was added D-tartaric acid (303 mg) at room temperature. The crystal was deposited under ultrasonication and the mixture was stirred for 3 hours. The deposited crystal was collected on a filter, washed with ethyl acetate (2 mL), and dried at 40° C. in vacuo to give SR-MDOZ mono-D-tartrate (643 mg, 1.57 mmol, yield: 81.8%).

To a solution of SR-MDOZ (500 mg, 1.92 mmol) in ethyl acetate (2 mL) and ethyl alcohol (0.5 mL) was added terephthalic acid (167.5 mg) at room temperature. After stirring the mixture at room temperature, the crystal was deposited under ultrasonication. To the suspension were added ethyl acetate (2 mL) and ethyl alcohol (0.5 mL), and the mixture was stirred at room temperature. The precipitated crystal was collected on a filter, washed with ethyl acetate (2 mL), and dried at 40° C. in vacuo to give SR-MDOZ 0.5-terephthalate.0.5-ethanolate (635 mg, 1.73 mmol, yield: 90.3

To a solution of SR-MDOZ (1.00 g, 3.84 mmol) in ethyl acetate (10 mL) was added terephthalic acid (326 mg) at room temperature. The mixture was stirred at room temperature for about 6 hours, and the precipitated crystal was collected on a filter, washed with ethyl acetate (6 mL), and dried at 40° C. in vacuo to give SR-MDOZ 0.5-terephthalate (868 mg, 2.53 mmol, yield: 65.9%).

To a solution of SR-MDOZ (1.00 g, 3.84 mmol) in ethyl acetate (4 mL) was added sulfuric acid (197 mg) at 0° C., and the weighing container was washed with ethyl acetate (1 mL). After the mixture was stirred at 0° C. and a precipitate appeared, ethyl acetate was added thereto at room temperature, and the mixture was stirred at room temperature for 1 hour. The precipitated crystal was collected on a filter, washed with ethyl acetate (1 mL), and dried at 40° C. in vacuo to give SR-MDOZ 0.5-sulfate (773 mg, 2.50 mmol, yield: 65.0%).

To a solution of SR-MDOZ (1.00 g, 3.84 mmol) in ethyl acetate (4 mL) and ethyl alcohol (1 mL) was added oxalic acid (176 mg) at room temperature. After the mixture was stirred at room temperature for more than 10 minutes and a precipitate appeared, ethyl acetate (4 mL) and ethyl alcohol (1 mL) were added thereto. The reaction mixture was stirred at room temperature for 30 minutes, and then the precipitated crystal was collected on a filter, washed with ethyl acetate (4 mL), and dried in vacuo to give SR-MDOZ 0.5-oxalate (1.08 g, 3.54 mmol, yield: 92.2%).

To a solution of SR-MDOZ (3.273 g, 12.57 mmol) in ethyl acetate (49 mL) and ethyl alcohol (6.5 mL) was added fumaric acid (1.60 g) at room temperature. The mixture was stirred at room temperature for about 1 hour, at 50° C. to 60° C. for about 2 hours, and further at room temperature overnight. The precipitated crystal was collected on a filter, washed with ethyl acetate (15 mL), and dried at 50° C. in vacuo to give SR-MDOZ mono-fumarate (4.295 g, 11.41 mmol, yield: 90.8%).

Each melting point of the prepared SR-MDOZ salts was measured.

TABLE 6

| Salt of SR-MDOZ | MP (DSC) | Solvent | Yield |
|---|---|---|---|
| mono oxalate | 139° C. | THF | 86.2% |
| mono L-tartrate | 151° C. | EtOAc, EtOH | 90.0% |
| mono D-tartrate | 132, 133° C. | EtOAc, EtOH | 81.8% |
| 0.5-terephthalate•0.5-ethanolate | — | EtOAc, EtOH | 90.3% |
| 0.5 terephthalate (anhydride crystal) | 151° C. | EtOAc | 65.9% |
| 0.5 sulfate | 176° C. | EtOAc | 65.0% |
| 0.5 oxalate | 170° C. | EtOAc, EtOH | 92.2% |
| mono fumarate | — | EtOAc, EtOH | 90.8% |

Example 12. Preparation of SR-MDPZ (Compound [16])

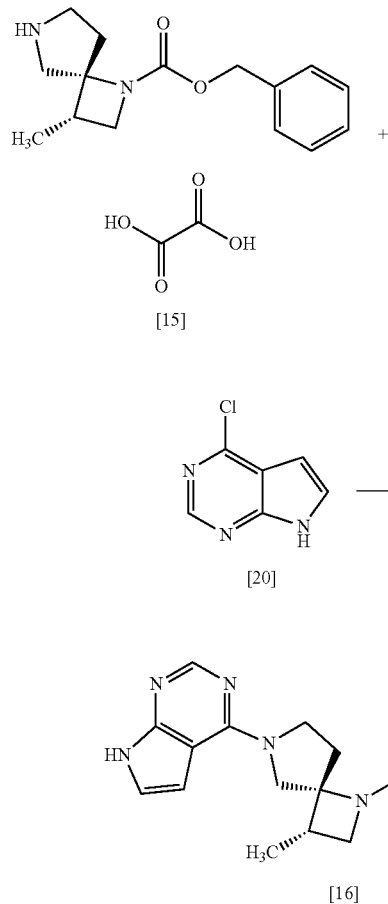

To SR-MDOZ-OX [15] (12.0 g, 34.2 mmol) were added ethanol (36 mL), water (72 mL), CPPY [20] (5.36 g, 34.9 mmol), and then $K_3PO_4$ (21.8 g, 103 mmol) under nitrogen atmosphere. The reaction mixture was stirred at 80° C. for 5 hours, and then cooled to 40° C. Toluene (120 mL) was added thereto at 40° C., and the organic layer was separated out. The resulting organic layer was washed with 20% aqueous potassium carbonate (48 mL), followed by washing twice with water (48 mL). The solvent of the organic layer was then removed in vacuo. tert-butanol (60 mL) was added to the residue and the tert-butanol solution was concentrated. The operation was repeated two more times. tert-Butanol (36 mL) was added to the concentrated residue to give a solution of SR-MDPZ [16] in tert-butanol (61.1 g, 34.2 mmol in theory). The given tert-butanol solution of SR-MDPZ was used in the next step, assuming that the yield was 100%.

SR-MDPZ which was prepared by the same process was isolated as a solid from a mixture of ethyl acetate and n-heptane, and then measured about NMR and MS.

$^1$H-NMR (DMSO-$d_6$) δ: 11.59 (br s, 1H), 8.08 (s, 1H), 7.41-7.26 (br m, 3H), 7.22-7.08 (br m, 3H), 6.64-6.51 (br m, 1H), 5.07-4.91 (br m, 2H), 4.09-3.67 (br m, 5H), 3.47-3.32 (br m, 1H), 2.67-2.55 (br m, 2H), 2.21-2.15 (br m, 1H), 1.11 (d, 3H, J=6.9 Hz).

MS: m/z=378 [M+H]$^1$

Example 13. Preparation of SR-MDOP (Compound [17])

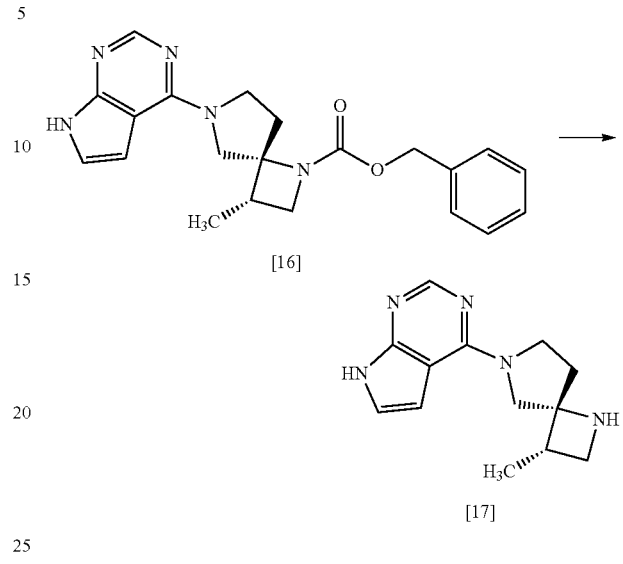

To the solution of SR-MDPZ [16] in tert-butanol (34.2 mmol in theory) were added ammonium formate (10.8 g, 171 mmol), water (60 mL), and 10% palladium carbon (made by Kawaken Fine Chemicals Co., Ltd., M type, 52.6% water-content, 1.20 g) under nitrogen atmosphere. The reaction mixture was stirred at 40° C. for 13 hours, and then cooled to room temperature, and the resulting precipitate was removed by filtration. The reaction vessel and the residue on the filter were washed with tert-butanol (24 mL), the washings was added to the filtrate, and 8 M aqueous sodium hydroxide (25.7 mL, 205 mmol) and sodium chloride (13.2 g) were added to the filtrate. The reaction mixture was stirred at 50° C. for 2 hours, and then toluene (84 mL) was added thereto at room temperature, and the organic layer was separated out. The resulting organic layer was washed with 20% brine (60 mL), stirred with anhydrous sodium sulfate, and then the sodium sulfate was removed by filtration. The residue on the filter was washed with a mixture of toluene:tert-butanol=1:1 (48 mL), the washings was added to the filtrate, and the filtrate was concentrated in vacuo. To the concentrated residue was added toluene (60 mL), and the solution was stirred at 50° C. for 2 hours, and then the solvent was removed in vacuo. To the concentrated residue was added toluene (60 mL) again, and the solution was concentrated. To the concentrated residue was added toluene (48 mL), and the solution was stirred at room temperature for 1 hour, and then at ice temperature for 1 hour. The precipitated solid was collected on a filter, and washed with toluene (24 mL). The resulting wet solid was dried in vacuo to give SR-MDOP [17] (7.07 g, 29.1 mmol, yield: 84.8%).

SR-MDOP which was prepared by the same process was measured about NMR and MS.

$^1$H-NMR (DMSO-$d_6$) δ: 11.57 (br s, 1H), 8.07 (s, 1H), 7.10 (d, 1H, J=3.2 Hz), 6.58 (d, 1H, J=3.2 Hz), 3.92-3.59 (br m, 4H), 3.49 (dd, 1H, J=8.3, 7.2 Hz), 2.93 (dd, 1H, J=7.2, 6.1 Hz), 2.61-2.53 (m, 2H), 2.12-2.01 (br m, 2H), 1.10 (d, 3H, J=6.9 Hz).

MS: m/z=244 [M+H]$^+$

Example 14. Preparation of Compound A mono-ethanolate (Compound [18])

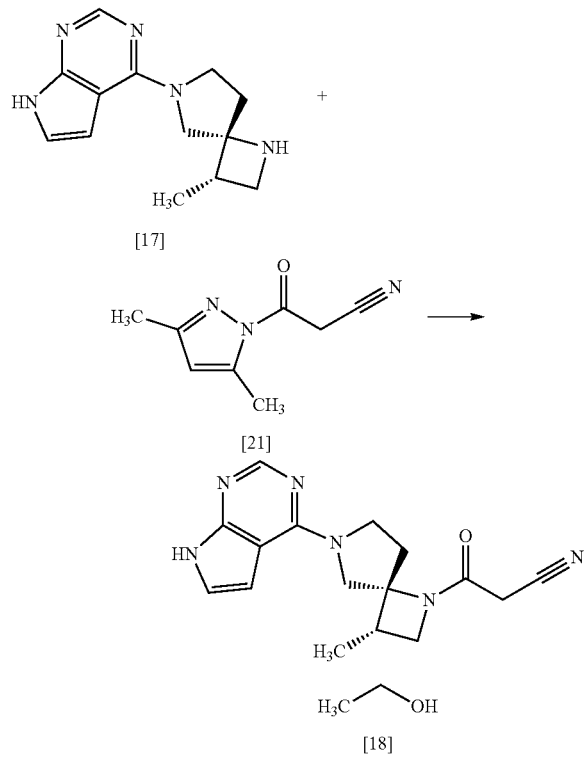

Under nitrogen atmosphere, acetonitrile (60 mL) and triethylamine (416 mg, 4.11 mmol) were added to SR-MDOP [17] (5.00 g, 20.5 mmol), and to the solution was added dropwise a solution of DPCN [21] (3.69 g, 22.6 mmol) in acetonitrile (35 mL) at 45° C., and then a dropping funnel used was washed with acetonitrile (5.0 mL) and the washings were added to the reaction mixture. The reaction mixture was stirred at 45° C. for 3 hours, and then cooled to room temperature. After 5% sodium bicarbonate water (25 mL), 10% brine (25 mL), and ethyl acetate (50 mL) were added to the reaction mixture and then the mixture was stirred, the organic layer was separated out. The solvent of the organic layer was removed out in vacuo. Tetrahydrofuran (50 mL) was added to the residue and the tetrahydrofuran solution was concentrated. The operation was repeated three more times. To the concentrated residue was added tetrahydrofuran (50 mL), and water was added the solution to adjust the water content to 5.5%. The resulting precipitate was removed by filtration. The reaction vessel and the residue on the filter were washed with tetrahydrofuran (15 mL), the washings were added to the filtrate, and the solvent was removed out of the filtrate in vacuo. To the concentrated residue were added ethanol (50 mL) and Compound A crystal (5.1 mg) that was prepared according to the method described in the following Example 15. The mixture was stirred at room temperature for 1 hour, and concentrated in vacuo. To the residue was ethanol (50 mL), and the solution was concentrated again. To the concentrated residue was added ethanol (15 mL), and the solution was stirred at room temperature for 1 hour. The precipitated solid was collected on the filter, and washed with ethanol (20 mL). The resulting wet solid was dried in vacuo to give Compound A mono-ethanolate [18] (6.26 g, 17.6 mmol, yield: 85.5%).

Compound A mono-ethanolate which was prepared by the same process was measured about NMR and MS.

$^1$H-NMR (DMSO-$d_6$) δ: 11.59 (br s, 1H), 8.08 (s, 1H), 7.11 (dd, 1H, J=3.5, 2.3 Hz), 6.58 (dd, 1H, J=3.5, 1.8 Hz), 4.34 (t, 1H, J=5.1 Hz), 4.16 (t, 1H, J=8.3 Hz), 4.09-3.92 (m, 3H), 3.84-3.73 (m, 1H), 3.71 (d, 1H, J=19.0 Hz), 3.65 (d, 1H, J=19.0 Hz), 3.58 (dd, 1H, J=8.2, 5.9 Hz), 3.44 (dq, 2H, J=6.7, 5.1 Hz), 2.69-2.60 (m, 2H), 2.23-2.13 (br m, 1H), 1.12 (d, 3H, J=7.1 Hz), 1.06 (t, 3H, J=6.7 Hz).

MS: m/z=311 [M+H]$^+$

Using Compound A mono-ethanolate obtained in Example 14, the diffraction angle 2θ and diffraction intensity were measured by the powder X-ray diffractometry.

The measured spectra are shown in FIG. 5.

Each peak in FIG. 5 is shown in the following table.

TABLE 7

| Diffraction angle [2θ (°)] | Relative intensity [%] | Diffraction intensity [cps] |
|---|---|---|
| 8.2766 | 100.00 | 5242.96 |
| 10.1326 | 7.13 | 373.78 |
| 10.9878 | 4.24 | 222.35 |
| 11.9948 | 17.20 | 901.98 |
| 12.6891 | 62.55 | 3279.46 |
| 12.9878 | 51.01 | 2674.69 |
| 13.9008 | 22.41 | 1174.98 |
| 16.5531 | 8.88 | 465.41 |
| 16.9986 | 8.63 | 452.65 |
| 18.1198 | 5.16 | 270.43 |
| 20.0465 | 61.93 | 3246.78 |
| 22.1386 | 5.14 | 269.54 |
| 23.2037 | 12.32 | 645.87 |
| 24.0783 | 38.48 | 2017.27 |

Using Compound A mono-ethanolate which was prepared by the same method, the diffraction angle 2θ and diffraction intensity were measured by the powder X-ray diffractometry. The measured spectra are shown in FIG. 6.

Each peak in FIG. 6 is shown in the following table.

TABLE 8

| Diffraction angle [2θ (°)] | Relative intensity [%] | Diffraction intensity [cps] |
|---|---|---|
| 8.2697 | 100.00 | 5765.29 |
| 10.0967 | 7.73 | 445.63 |
| 11.0161 | 4.77 | 275.16 |
| 11.9986 | 19.17 | 1105.32 |
| 12.6933 | 63.30 | 3649.39 |
| 12.9629 | 58.64 | 3380.72 |
| 13.8549 | 25.71 | 1482.08 |
| 14.8506 | 4.53 | 261.35 |
| 16.5910 | 10.63 | 613.11 |
| 17.0458 | 10.84 | 624.86 |
| 18.1156 | 6.92 | 399.14 |
| 20.0496 | 64.61 | 3724.97 |
| 22.1288 | 6.60 | 380.77 |
| 23.1059 | 13.68 | 788.68 |
| 24.0968 | 38.33 | 2209.75 |

Example 15. Purification of Compound A (Compound [19])

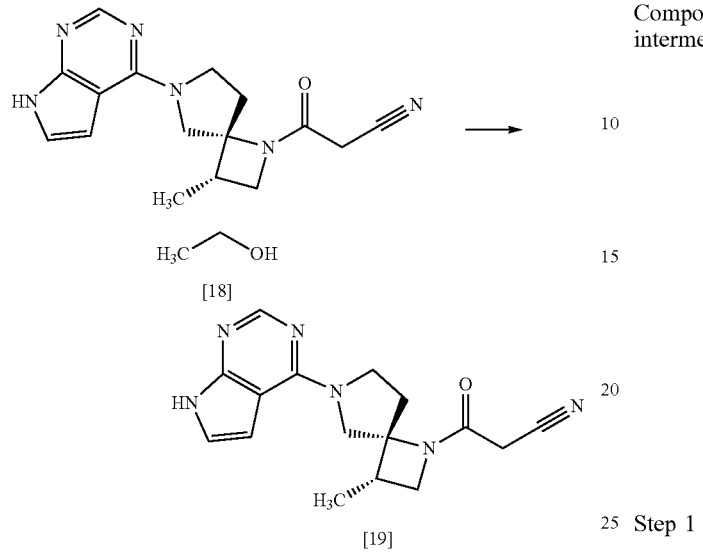

Compound A mono-ethanolate [18] (4.00 g, 11.2 mmol) and n-butanol (32 mL) were mixed under nitrogen atmosphere, and the mixture was dissolved at 110° C. The mixture was cooled to 85° C., and Compound A crystal (4.0 mg) that was prepared according to the method described herein was added thereto, and the mixture was stirred at 85° C. for 2 hours, at 75° C. for 1 hour, and then at room temperature for 16 hours. The precipitated solid was collected on a filter, and washed with n-butanol (8.0 mL) and then ethyl acetate (8.0 mL). The resulting wet solid was dried in vacuo to give Compound A [19] (3.18 g, 10.2 mmol, yield: 91.3%).

Compound A which was prepared by the same process was measured about NMR and MS.

$^1$H-NMR (DMSO-$d_6$) δ: 11.59 (br s, 1H), 8.08 (s, 1H), 7.11 (dd, 1H, J=3.5, 2.5 Hz), 6.58 (dd, 1H, J=3.5, 1.8 Hz), 4.16 (t, 1H, J=8.3 Hz), 4.09-3.93 (m, 3H), 3.84-3.73 (m, 1H), 3.71 (d, 1H, J=19.0 Hz), 3.65 (d, 1H, J=19.0 Hz), 3.58 (dd, 1H, J=8.2, 5.9 Hz), 2.69-2.59 (m, 2H), 2.23-2.13 (m, 1H), 1.12 (d, 3H, J=7.2 Hz).

MS: m/z=311 [M+H]$^+$

Using Compound A which was prepared by the same method, the single crystal X-ray analysis was carried out.

(1) Preparation of Single Crystal

To 10 mg of Compound A in a LaPha ROBO Vial® 2.0 mL wide-mouthed vial was added 0.5 mL of chloroform. The vial was covered with a cap, in which Compound A was completely dissolved. In order to evaporate the solvent slowly, a hole was made on the septum attached in the cap with a needle of a TERUMO® syringe, and the vial was still stood at room temperature. The resulting single crystal was used in the structural analysis.

(2) Measuring Instrument

Beam line: SPring-8 BL32B2

Detector: Rigaku R-AXIS V diffractometer (3) Measuring Method

The radiant light of 0.71068 Å was irradiated to the single crystal to measure X-ray diffraction data.

(4) Assay Method

Using the X-ray anomalous scattering effect of the chlorine atom in the resulting Compound A chloroform-solvate, the absolute configuration of Compound A was identified as (3S,4R). Based on the obtained absolute configuration of Compound A, the absolute configurations of each process intermediate were identified.

Example 16. Preparation of S-MABB-HC (Compound [5])

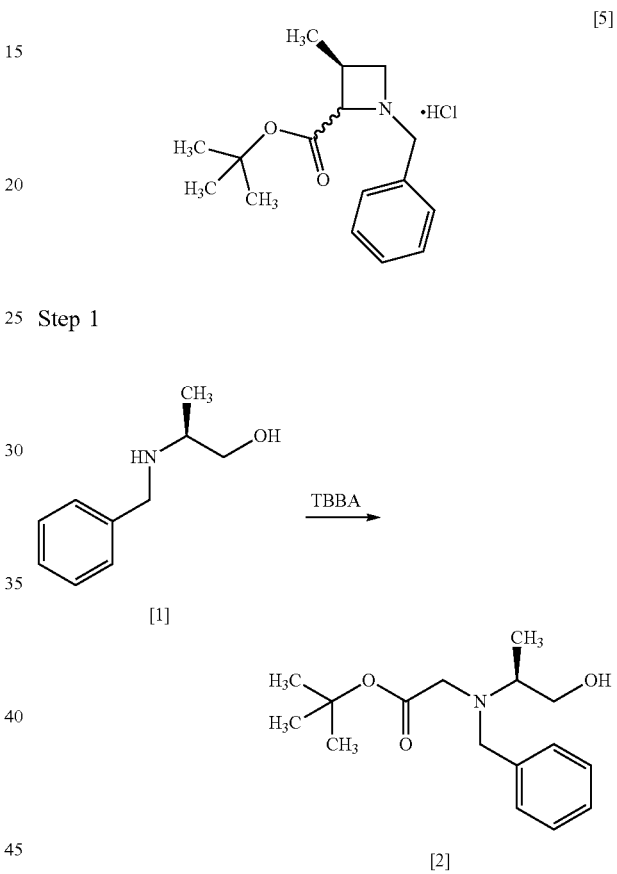

Step 1

S-BAPO [1] (90.0 kg, 545 mol) was added to tetrahydrofuran (450 L) at room temperature under nitrogen atmosphere. To the resulting suspension were added potassium carbonate (135.5 g, 981 mol) at room temperature. To the resulting solution was added TBBA (148.7 kg, 763 mol) at room temperature, and then a dropping funnel used was washed with tetrahydrofuran (45 L) and the washings were added to the reaction mixture. The reaction mixture was stirred at 55° C. for 22 hours, and then cooled to room temperature. After water (450 L) and n-heptane (450 L) were added to the reaction mixture and then the mixture was stirred, the organic layer was separated out. After 10% aqueous sodium chloride (450 L) was added to the resulting organic layer and then the mixture was stirred, the organic layer was separated out. The organic layer was stirred with 2 mol/L hydrochloric acid (450 L), and then the aqueous layer was separated out. To the resulting aqueous layer was added dropwise 4 mol/L aqueous sodium hydroxide solution to adjust the pH to 7.0 to 8.0 at 15° C. to 30° C. The aqueous layer was stirred with toluene (450 L), and the organic layer was separated out. The organic layer was stirred with water (450 L), and the organic layer was separated out. The solvent of the organic layer was removed in vacuo to a volume of 180 L at 50° C. of the outside temperature. To the concentrated residue was added toluene (270 L), and the solution was concentrated in vacuo to a volume of 180 L at 50° C. of the outside temperature. The given toluene solution of S-BBMO [2] was used in the next step, assuming that the yield was 100%.

Step 2

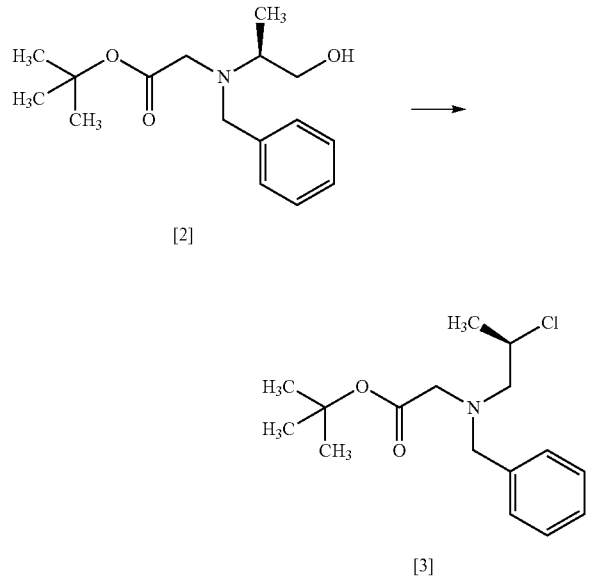

To the toluene solution of S-BBMO [2] (545 mol in theory) were added tetrahydrofuran (450 L) and triethylamine (82.7 kg, 818 mol) at room temperature under nitrogen atmosphere. The used dropping funnel was washed with tetrahydrofuran (45 L) and the washings were added to the reaction mixture. To the mixture was added dropwise methanesulfonyl chloride (74.9 kg, 654 mol) at 0° C. to 30° C., and then a dropping funnel used was washed with tetrahydrofuran (45 L) and the washings were added to the reaction mixture. The reaction mixture was stirred at 0° C. to 30° C. for 0.5 hour and further at 55° C. for 17 hours, and then cooled to room temperature. After water (450 L) and n-heptane (450 L) were added to the reaction mixture and then the mixture was stirred, the organic layer was separated out. After 5% aqueous solution of citric acid (450 L) was added to the organic layer and then the mixture was stirred, the organic layer was separated out. After 5% sodium bicarbonate water (450 L) was added to the organic layer and then the mixture was stirred, the organic layer was separated out. The resulting organic layer was washed with water (450 L), the aqueous layer was removed, and the solvent of the organic layer was removed in vacuo to a volume of 180 L at 50° C. of the outside temperature. To the concentrated residue was added tetrahydrofuran (450 L), and the solution was concentrated in vacuo to a volume of 180 L at 50° C. of the outside temperature. The given tetrahydrofuran solution of R-BCAB [3] was used in the next step, assuming that the yield was 100%.

Step 3

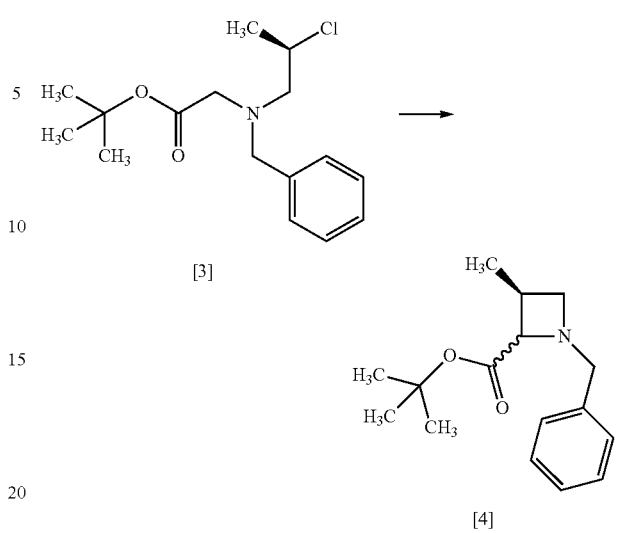

To the tetrahydrofuran solution of R-BCAB [3] (545 mol in theory) were added tetrahydrofuran (585 L) and 1,3-dimethyl-3,4,5,6-tetrahydro-2(1H)-pyrimidinone (108 L) at room temperature under nitrogen atmosphere. To the mixture was added dropwise a solution of 20% lithium bis(trimethylsilyl)amide/tetrahydrofuran (524 kg) at −10° C. to 5° C. The reaction mixture was stirred at −10° C. to 5° C. for 3.5 hours, and then warmed to room temperature. After water (450 L) and n-heptane (450 L) were added to the reaction mixture and then the mixture was stirred, the organic layer was separated out. After 25% aqueous ammonium chloride (450 L) was added to the resulting organic layer and then the mixture was stirred, the organic layer was separated out. After 2 mol/L hydrochloric acid (900 L) was added to the organic layer and then the mixture was stirred, the aqueous layer was separated out. To the resulting aqueous layer was added dropwise 4 mol/L aqueous sodium hydroxide solution to adjust the pH to 7.0 to 8.0 at 15° C. to 30° C. After ethyl acetate (450 L) was added to the aqueous layer and then the mixture was stirred, the organic layer was separated out. After water (450 L) was added to the organic layer and then the mixture was stirred, the organic layer was separated out. To the organic layer was added active carbon (18 kg) and the mixture was stirred, and then the active carbon was removed by filtration. The dropping funnel and the active carbon were washed with ethyl acetate (450 L), and the washings were added to the filtration. The solvent of the filtrate was removed in vacuo to a volume of 180 L at 50° C. of the outside temperature. To the concentrated residue was added ethyl acetate (270 L), and the solution was concentrated in vacuo to a volume of 180 L at 50° C. of the outside temperature. The given ethyl acetate solution of S-MABB [4] was used in the next step, assuming that the yield was 100%.

Step 4

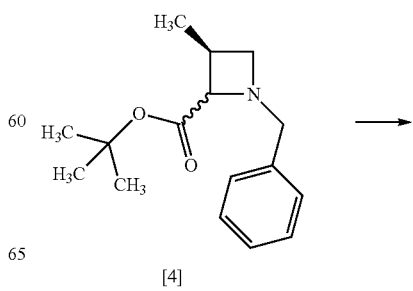

-continued

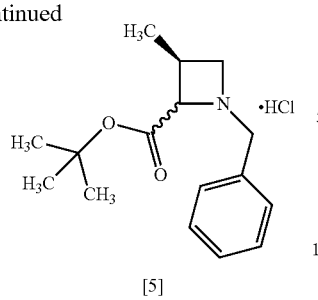

[5]

To the ethyl acetate solution of S-MABB [4] (545 mol in theory) were added isopropyl acetate (1080 L) and S-MABB-HC crystal (225 g) that was prepared according to the method described herein under nitrogen atmosphere. A solution of 4 mol/L hydrogen chloride/ethyl acetate (136 L) was added dropwise thereto at 0° C. to 30° C. The reaction mixture was stirred at 0° C. to 30° C. for 24 hours, and then the precipitated solid was collected on a filter, and washed with isopropyl acetate (360 L). The resulting wet solid was dried in vacuo to give S-MABB-HC [5] (111.9 kg, 376 mol, yield: 69.0% from S-BAPO [1]).

Example 17. Preparation of S-MACB-HC (Compound [6])

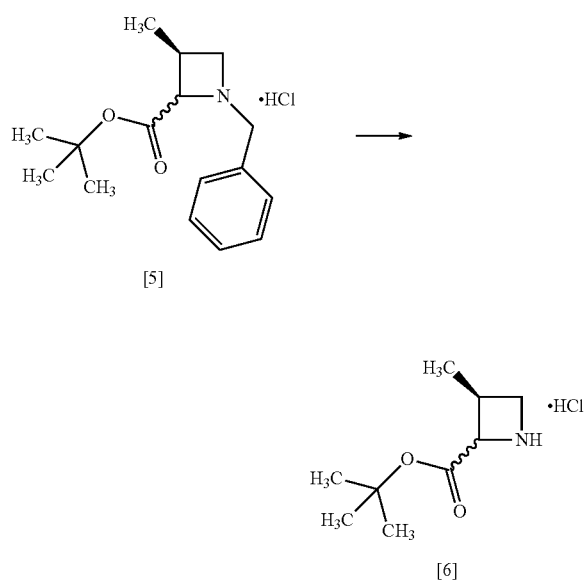

Methanol (336 L) was added to S-MABB-HC [5] (111.9 kg, 376 mol) under nitrogen atmosphere. To the mixture were added a suspension of 10% palladium carbon (50% water-content, 11.2 kg) and methanol (112 L). The mixture was stirred at hydrogen pressure of 0.4 MPa for 11 hours, and then the palladium carbon was removed by filtration. The reaction vessel and the palladium carbon were washed with methanol (224 L), and then the washings were added to the filtration. The given methanol solution of S-MACB-HC [6] was used in the next step, assuming that the yield was 100%.

Example 18. Preparation of S-ZMAB (Compound [7])

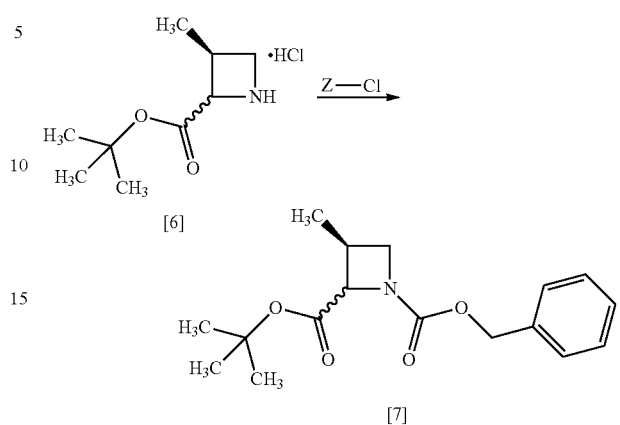

To the methanol solution of S-MACB-HC [6] (376 mol in theory) was added N,N-diisopropylethylamine (106.8 kg, 827 mol) under nitrogen atmosphere. The used dropping funnel was washed with tetrahydrofuran (56 L) and the washings were added to the reaction mixture. To the resulting reaction mixture was added dropwise benzyl chloroformate (64.1 kg, 376 mol) at 0° C. to 15° C. The used dropping funnel was washed with tetrahydrofuran (56 L) and the washings were added to the reaction mixture. The reaction mixture was stirred at 0° C. for 2 hours, and then concentrated in vacuo to a volume of 224 L at 50° C. of the outside temperature. To the concentrated residue was added ethyl acetate (560 L), and the solution was concentrated in vacuo to a volume of 224 L at 50° C. of the outside temperature. The operation was repeated one more time. After water (560 L) and ethyl acetate (1119 L) were added to the residue and then the mixture was stirred, the organic layer was separated out. After 5% aqueous solution of citric acid (560 L) was added to the organic layer and then the mixture was stirred, the organic layer was separated out. After 5% sodium bicarbonate water (560 L) was added to the resulting organic layer and then the mixture was stirred, the organic layer was separated out. After water (560 L) was added to the organic layer and then the mixture was stirred, the organic layer was separated out. The solvent of the organic layer was removed in vacuo to a volume of 224 L at 50° C. of the outside temperature. To the concentrated residue was added tetrahydrofuran (224 L), and the solution was concentrated in vacuo to a volume of 224 L at 50° C. of the outside temperature. The operation was repeated one more time. The given tetrahydrofuran solution of S-ZMAB [7] was used in the next step, assuming that the yield was 100%.

Example 19. Preparation of RS-ZMBB (Compound [8])

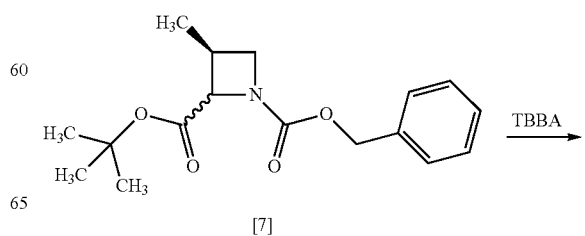

-continued

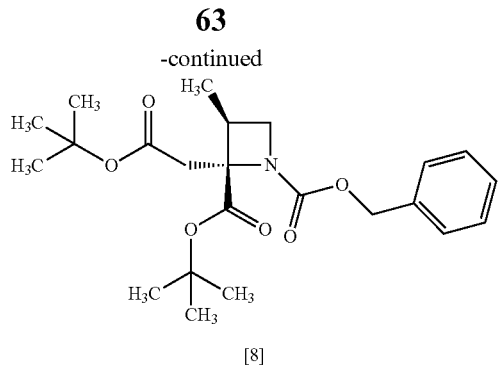

[8]

To the tetrahydrofuran solution of S-ZMAB [7] (188 mol in theory) was added tetrahydrofuran (308 L) under nitrogen atmosphere. To the solution was added dropwise a solution of 20% lithium bis(trimethylsilyl)amide/tetrahydrofuran (188.8 kg) at −70° C. to −60° C., and then the reaction mixture was stirred at −70° C. to −60° C. for 3 hours. To the reaction mixture was added dropwise a solution of TBBA (44 kg, 226 mol) in tetrahydrofuran (84 L) at −70° C. to −60° C. The used dropping funnel was washed with tetrahydrofuran (28 L) and the washings were added to the reaction mixture. The reaction mixture was stirred at −70° C. to −60° C. for 2.5 hours, and then warmed to 0° C. After 15% aqueous ammonium chloride (280 L) and ethyl acetate (560 L) were added to the reaction mixture at 0° C. to 30° C. and then the mixture was stirred, the organic layer was separated out. The resulting organic layer was washed with 10% aqueous citric acid (280 L, ×2), 8.5% aqueous sodium bicarbonate (280 L), and then water (280 L), and then the solvent of the organic layer was removed in vacuo to a volume of 112 L at 50° C. of the outside temperature. To the concentrated residue was added acetonitrile (280 L), and the solution was concentrated in vacuo to a volume of 112 L at 50° C. of the outside temperature. The given acetonitrile solution of RS-ZMBB [8] was used in the next step, assuming that the yield was 100

Example 20. Preparation of RS-ZMAA-DN.2H$_2$O (Compound [9])

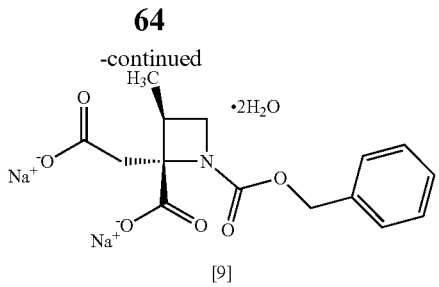

[9]

To the acetonitrile solution of RS-ZMBB [8] (376 mol in theory) were added acetonitrile (280 L) and phosphoric acid (346.5 kg) under nitrogen atmosphere. The used vessel was washed with acetonitrile (56 L), and the washings were added to the reaction mixture. The reaction mixture was stirred at 55° C. to 65° C. for 9 hours, and then cooled to room temperature. After 5% aqueous sodium chloride (560 L) and ethyl acetate (1119 L) were added to the reaction mixture and then the mixture was stirred, the organic layer was separated out. The organic layer was stirred with 5% aqueous sodium chloride (560 L), and then the organic layer was separated out. The operation was repeated one more time. After water (560 L) was added to the resulting organic layer and then the mixture was stirred, the organic layer was separated out. The solvent of the organic layer was removed in vacuo to a volume of 224 L at 50° C. of the outside temperature. To the concentrated residue was added acetonitrile (560 L), and the solution was concentrated in vacuo to a volume of 224 L at 50° C. of the outside temperature. The operation was repeated one more time. The resulting acetonitrile solution of RS-ZMAA [10] was used in the next step to prepare RS-ZMAA-DN [9], assuming that the yield was 100%. To an acetonitrile solution of RS-ZMAA [10] were added acetonitrile (1063 L) and water (168 L). 4 mol/L Aqueous sodium hydroxide (188 L, 752 mol) was added dropwise at 0° C. to 30° C. The reaction mixture was stirred at room temperature for 1 hour, acetonitrile (336 L) was added dropwise thereto at room temperature, and then the reaction mixture was stirred at room temperature for another 1 hour. The precipitated solid was collected on a filter, and washed with a mixture of acetonitrile:water=4:1 (224 L) and then acetonitrile (224 L). The resulting wet solid was dried in vacuo to give RS-ZMAA-DN.2H$_2$O [9] (88.2 kg, 251 mol, yield: 66.8% from S-MABB-HC [6]).

Example 21. Preparation of RS-ZMAA (Compound [10])

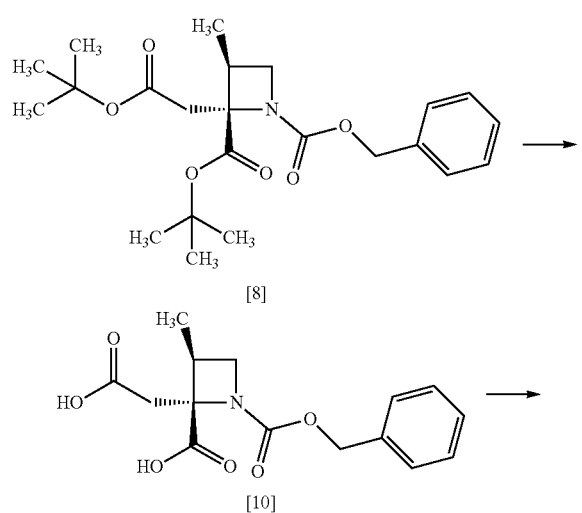

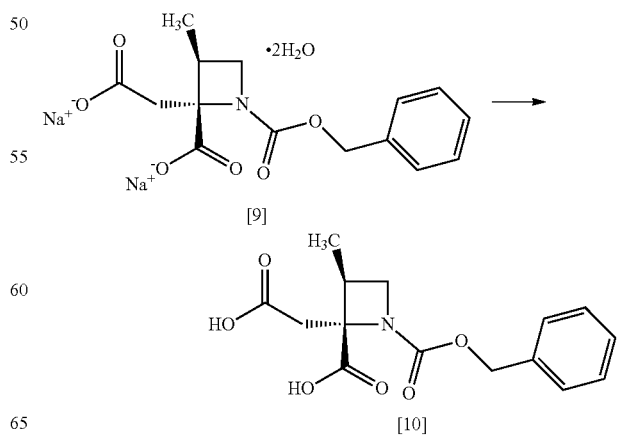

To 1 mol/L hydrochloric acid (697 kg) were added RS-ZMAA-DN.2H$_2$O [9](115 kg, 297 mol) and acetonitrile (181 kg), and the mixture was stirred at room temperature for about 30 minutes, and then ethyl acetate (828 kg) was added thereto. To the reaction solution was added concentrated hydrochloric acid (3 kg) at room temperature. The pH of the aqueous layer was adjusted to 1, and then the organic layer was separated out. The organic layer was washed with 10% brine (248 kg×2). The organic layer was passed through a filter bedded with magnesium sulfate (25 kg), and the filter was washed with ethyl acetate (207 kg). The washings were added to the filtrate, and then the solvent was removed out of the filtrate in vacuo. Tetrahydrofuran (920 L) was added to the residue and the tetrahydrofuran solution was concentrated. The operation was repeated one more time. To the concentrated residue was added tetrahydrofuran (230 L) to give a tetrahydrofuran solution of RS-ZMAA [10]. The given tetrahydrofuran solution of RS-ZMAA [10] was used in the next step, assuming that the yield was 100%.

Example 22. Preparation of RS-ZMOO (Compound [11])

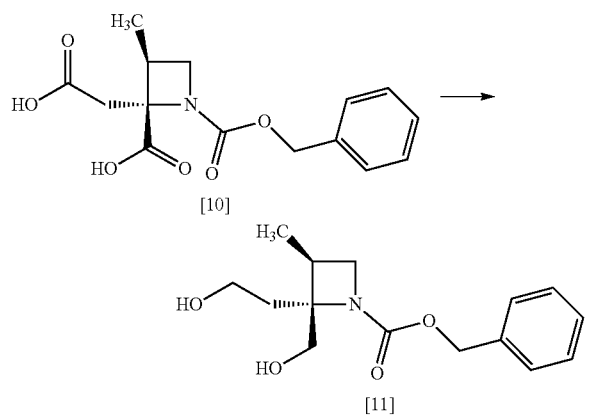

To the tetrahydrofuran solution of RS-ZMAA [10] (297 mol in theory) was added tetrahydrofuran (633 L) under nitrogen atmosphere. Boron trifluoride etherate complex (50.6 kg) was added dropwise thereto at −5° C. to 5° C. And, 1.7% borane-tetrahydrofuran complex (486 kg) was added dropwise thereto at −5° C. to 5° C., and the reaction mixture was stirred at −5° C. to 5° C. for about 30 minutes, and further at room temperature overnight. To the reaction mixture was added dropwise water (575 L) at 0° C. to 15° C., then sodium bicarbonate (62.4 kg) at 0° C. to 15° C., and the mixture was stirred at room temperature for about 2 hours. After toluene (575 L) was added to the reaction mixture at room temperature and then the mixture was stirred, the organic layer was separated out. The resulting organic layer was washed with 10% brine (248 kg×1), an aqueous solution (485.3 kg×3) of sodium bicarbonate (11.8 kg) and sodium chloride (24.8 kg), an aqueous solution (242.7 g, ×1) of potassium hydrogensulfate (5.9 kg) and sodium chloride (12.4 kg), and then 10% brine (248.4 kg, ×2). The organic layer was passed through a filter bedded with magnesium sulfate (58 kg) and a filter bedded with magnesium sulfate (30 kg), and each filter was washed with toluene (230 L). The washings were added to the filtrate, and then the solvent of the filtrate was removed in vacuo. To the concentrated residue was added toluene (920 L), the solution was concentrated in vacuo, and then toluene (621 L) was added to the residue to give a toluene solution of RS-ZMOO [11]. The given toluene solution of RS-ZMOO [11] was used in the next step, assuming that the yield was 100%.

Example 23. Preparation of RS-ZMSS (Compound [12])

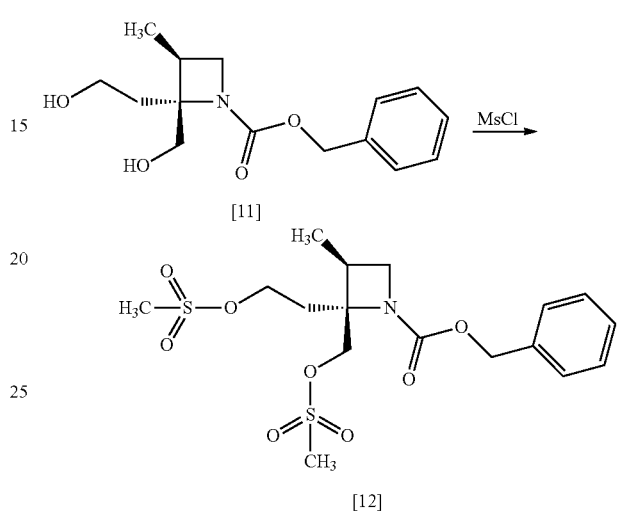

To the toluene solution of RS-ZMOO [11] (297 mol in theory) was added dropwise triethylamine (66.1 kg) at −10° C. to 10° C. under nitrogen atmosphere. To this reaction mixture was added dropwise methanesulfonyl chloride (71.4 kg) at −10° C. to 10° C., and the mixture was stirred at 0° C. to 10° C. for about 4 hours. To the reaction mixture was added dropwise water (345 L) at 0° C. to 20° C. The reaction mixture was stirred at 0° C. to 20° C. for about 30 minutes, and the organic layer was separated out. The resulting organic layer was washed with 10% brine (248 kg, ×2). The organic layer was passed through a filter bedded with magnesium sulfate (35 kg), and the filter was washed with toluene (230 L). The washings were added to the filtrate, and the solvent was removed out of the filtrate in vacuo. To the concentrated residue was added toluene (690 L) to give a toluene solution of RS-ZMSS [12]. The given toluene solution of RS-ZMSS [12] was used in the next step, assuming that the yield was 100%.

Example 24. Preparation of SR-ZMDB (Compound [13])

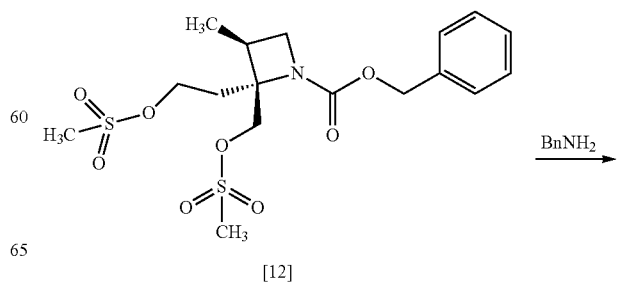

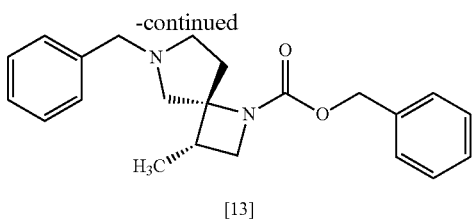

[13]

To the toluene solution of RS-ZMSS [12] (297 mol in theory) was added dropwise benzylamine (222.7 kg) at room temperature under nitrogen atmosphere. The reaction mixture was stirred at room temperature for about 1 hour and 20 minutes, at 55° C. to 65° C. for about 3 hours, and then at 70° C. to 80° C. for about 8 hours. After the reaction mixture was cooled to room temperature, 10% brine (373 kg) dropwise was added thereto and further toluene (460 L) was added thereto, the mixture was stirred, and then the organic layer was separated out. The resulting organic layer was washed with a solution (×2) of 10% brine (248 kg) and acetic acid (32.1 kg), and then 10% brine (149 kg, ×1). The solvent of the organic layer was removed in vacuo to a half volume, and acetic anhydride (18.2 kg) was added thereto at room temperature. The mixture was stirred for about 2 hours. To the reaction mixture were added dropwise a solution of potassium hydrogensulfate (48.5 kg) and water (1150 kg) at room temperature. The reaction mixture was stirred, and then the aqueous layer was separated out. The resulting aqueous layer was washed with toluene (230 L), and toluene (920 L) and then sodium bicarbonate (82.3 kg) were added to the aqueous layer at room temperature, and the mixture was stirred. The organic layer was separated out, and washed with 10% brine (149 kg). The organic layer was passed through a filter bedded with magnesium sulfate (35 kg), and the filter was washed with toluene (230 L). The washings were added to the filtrate, and then the filtrate was concentrated in vacuo. Toluene (460 L) was added to the concentrated residue to give a toluene solution of SR-ZMDB [13]. The given toluene solution of SR-ZMDB [13] was used in the next step, assuming that the yield was 100%.

Example 25. Preparation of SR-MDOZ (Compound [14])

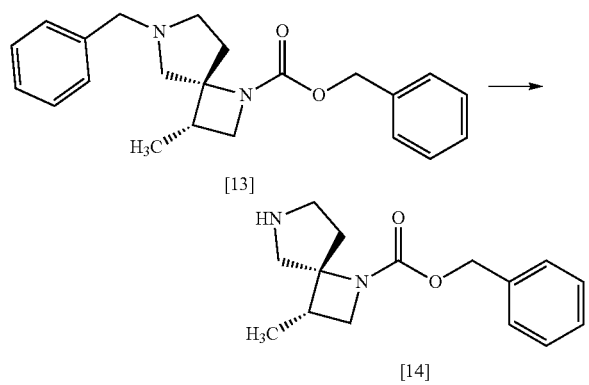

1-Chloroethyl chloroformate (46.7 kg) was dissolved in toluene (345 L), and thereto was added dropwise the toluene solution of SR-ZMDB [13] (297 mol in theory) at 0° C. to 10° C. under nitrogen atmosphere. The vessel that contained the SR-ZMDB toluene solution was washed with toluene (58 L) and the washings were added to the reaction mixture. To the reaction mixture was added dropwise triethylamine (9.0 kg) at 0° C. to 10° C., and the reaction mixture was stirred at 15° C. to 25° C. for about 3 hours. Then, methyl alcohol (454 kg) was added to the reaction mixture, and the mixture was stirred at 50° C. to 60° C. for about 2 hours. The reaction solution was concentrated in vacuo to a volume of about 460 L. To the concentrated residue was added dropwise 2 mol/L hydrochloric acid (621 kg) at 15° C. to 30° C., and then the aqueous layer was separated out. The resulting aqueous layer was washed with toluene (345 L, ×2). To the aqueous layer were added 20% brine (661 kg) and tetrahydrofuran (1150 L), and then 8 mol/L aqueous sodium hydroxide (292 kg) was added dropwise thereto at 0° C. to 15° C. The organic layer was separated out from the reaction mixture, washed with 20% brine (265 kg, ×2), and then the solvent of the organic layer was removed in vacuo. Tetrahydrofuran (1150 L) was added to the residue and the tetrahydrofuran solution was concentrated. The operation was repeated one more time. The concentrated residue was dissolved in tetrahydrofuran (1150 L). The solution was passed through a filter bedded with magnesium sulfate (35 kg). The filter was washed with tetrahydrofuran (345 L), and the washings were added to the filtrate. The solvent of the filtrate was removed in vacuo to a volume of about less than 230 L. Tetrahydrofuran (30 L) was added to the given residue to give a tetrahydrofuran solution of SR-MDOZ [14] (net weight 51.9 kg, 199 mol, yield: 67.0

Example 26. Preparation of SR-MDOZ-OX (Compound [15])

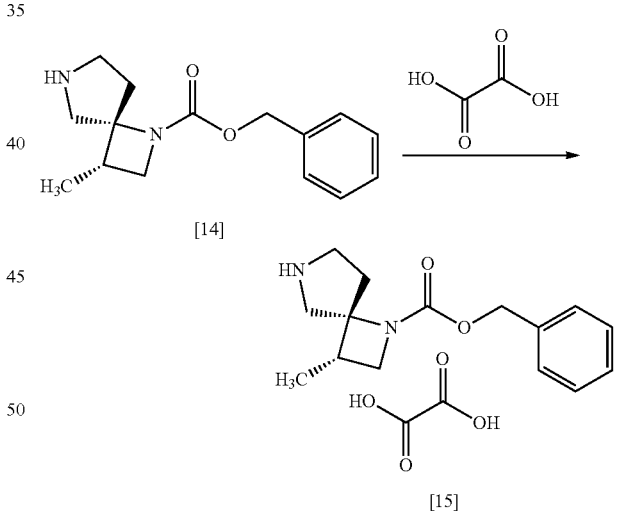

Under nitrogen atmosphere, oxalic acid (19.7 kg) was dissolved in tetrahydrofuran (1038 L), and to the solution was added dropwise a tetrahydrofuran solution of SR-MDOZ [14] (99.5 mol) at room temperature. To the solution was added SR-MDOZ-OX crystal (26 g) that was prepared according to the method described herein at room temperature, and the mixture was stirred at room temperature for about 2.5 hours to precipitate the crystal. To the given slurry solution was added dropwise the tetrahydrofuran solution of SR-MDOZ (99.5 mol). The vessel wherein the tetrahydrofuran solution of SR-MDOZ was contained was washed with tetrahydrofuran (52 L), and then the washings were added to the slurry solution. The mixture was stirred at room temperature for about 1 hour. The slurry solution was heated, and stirred at 50° C. to 60° C. for about 2 hours, and then stirred at room temperature overnight. The slurry solution was filtrated, and the wet crystal on the filter was washed with tetrahydrofuran (350 L), dried in vacuo to give a crystal of SR-MDOZ-OX [15] (61.8 kg, 176 mol 1, yield: 88.4%).

Example 27. Preparation of SR-MDPZ (Compound [16])

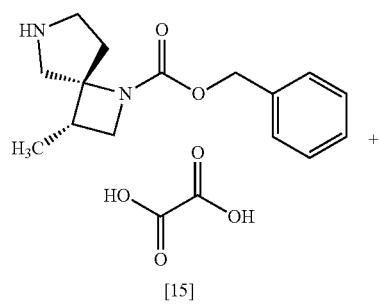

[15]

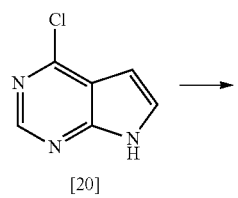

[20]

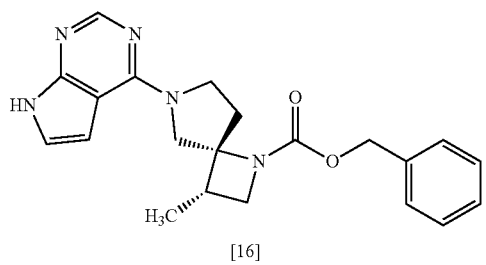

[16]

To SR-MDOZ-OX [15] (32.0 kg, 91.3 mol) were added ethanol (77 kg), water (190 L), CPPY [20] (14.3 kg, 93.1 mol), and then K$_3$PO$_4$ (58.2 kg, 274 mol) under nitrogen atmosphere. The reaction mixture was stirred at 75° C. to 85° C. for 3.5 hours, and then cooled to 30° C. to 40° C. Toluene (280 kg) was added thereto at 30° C. to 40° C., and the organic layer was separated out. The resulting organic layer was washed with 20% aqueous potassium carbonate (126 kg) followed by washing twice with water (130 L). The solvent of the organic layer was then removed in vacuo. tert-Butanol (120 kg) was added to the residue and the tert-butanol solution was concentrated. The operation was repeated two more times. To the concentrated residue were added tert-butanol (67 kg) and water (16 L) to give a solution of SR-MDPZ/water-containing tert-butanol (210 kg, 91.3 mol in theory). The given solution of SR-MDPZ [16] in water-containing tert-butanol was used in the next step, assuming that the yield was 100%.

Example 28. Preparation of SR-MDOP (Compound [17])

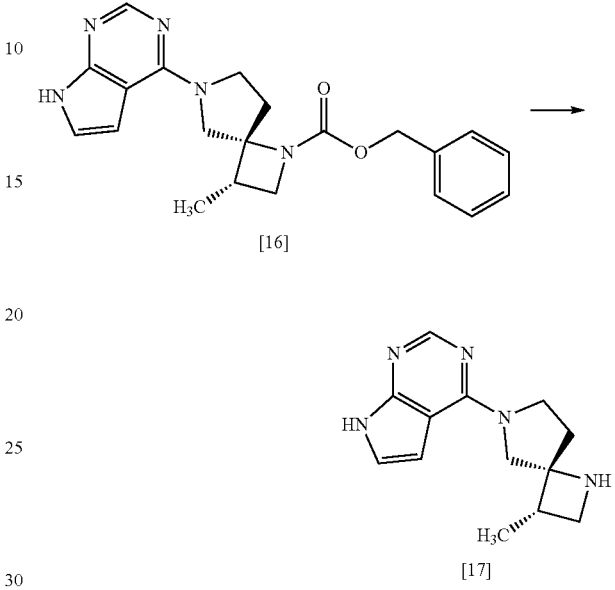

To the solution of SR-MDPZ [16] in water-containing tert-butanol (91.3 mol in theory) were added ammonium formate (28.9 kg, 458 mol), water (147 L), and 10% palladium carbon (made by Kawaken Fine Chemicals Co., Ltd., M type, 52.6% water-content, 3.20 kg) under nitrogen atmosphere. The reaction mixture was stirred at 35° C. to 45° C. for 12 hours, and then cooled to 15° C. to 30° C., and the resulting precipitate was removed by filtration. The reaction vessel and the residue on the filter were washed with tert-butanol (48 kg), the washings were added to the filtrate, and 8 M aqueous sodium hydroxide (88.0 kg, 547 mol) and sodium chloride (35.0 kg) were added to the filtrate. The reaction mixture was stirred at 40° C. to 50° C. for 2 hours, and then toluene (190 kg) was added thereto at room temperature, and the organic layer was separated out. The resulting organic layer was washed with 20% brine (162 kg), stirred with anhydrous sodium sulfate (48.0 kg), and then the sodium sulfate was removed by filtration. The residue on the filter was washed with a mixture of toluene: tert-butanol=1:1 (103 kg), the washings were added to the filtrate, and the filtrate was concentrated in vacuo. To the concentrated residue was added toluene (140 kg), and the solution was stirred at 40° C. to 50° C. for 1 hour, and then concentrated in vacuo. To the concentrated residue was added toluene (140 kg) again, and the solution was concentrated. To the concentrated residue was added toluene (133 kg), and the solution was stirred at 15° C. to 30° C. for 1 hour, and then at 0° C. to 10° C. for 1 hour. The precipitated solid was collected on a filter, and washed with toluene (55 kg). The resulting wet solid was dried in vacuo to give SR-MDOP [17] (19.1 kg, 78.5 mol 1, yield: 85.9%).

Example 29. Preparation of Compound A mono-ethanolate (Compound [18])

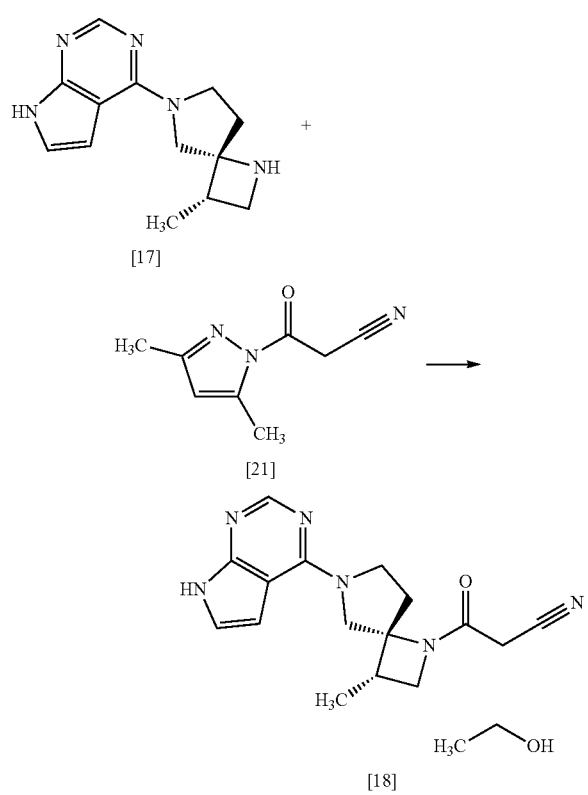

Under nitrogen atmosphere, acetonitrile (170 kg) and triethylamine (1.55 kg, 15.3 mol) were added to SR-MDOP [17] (18.6 kg, 76.4 mol), and to the solution was added dropwise a solution of DPCN [21] (13.7 kg, 83.9 mol) in acetonitrile (100 kg) at 40° C. to 50° C., and then a dropping funnel used was washed with acetonitrile (15 kg) and the washings were added to the reaction mixture. The reaction mixture was stirred at 40° C. to 50° C. for 20 hours, and then cooled to 15° C. to 30° C. After 5% sodium bicarbonate water (93.7 kg), 10% brine (93.3 kg), and ethyl acetate (170 kg) were added to the reaction mixture, the organic layer was separated out. The solvent was removed out of the organic layer in vacuo. Tetrahydrofuran (170 kg) was added to the residue and the tetrahydrofuran solution was concentrated. The operation was repeated two more times. To the concentrated residue was added tetrahydrofuran (170 kg), and the resulting precipitate was removed by filtration. The reaction vessel and the residue on the filter were washed with tetrahydrofuran (50 kg), the washings were added to the filtrate, and the solvent was removed out of the filtrate in vacuo. To the concentrated residue was added ethanol (150 kg), and the solution was stirred at 15° C. to 30° C. for 1 hour and concentrated in vacuo. To the residue was ethanol (150 kg), and the solution was concentrated again. To the concentrated residue was added ethanol (50 kg), and the solution was stirred at 0° C. to 10° C. for 1 hour. The precipitated solid was collected on the filter, and the resulting wet solid was dried in vacuo to give Compound A mono-ethanolate [18] (24.2 kg, 67.9 mol, yield: 88.8%).

Example 30. Purification of Compound A (Compound [19])

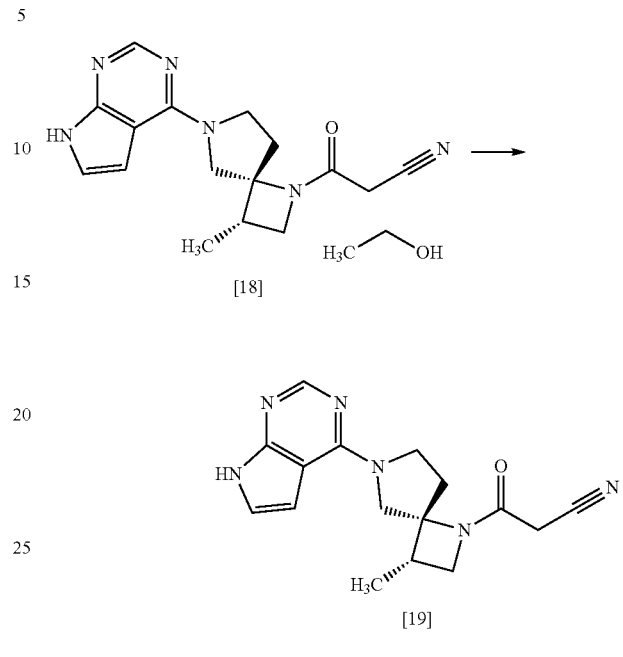

Compound A mono-ethanolate [18] (24.0 kg, 67.3 mol) and n-butanol (146 kg) were mixed under nitrogen atmosphere, and the mixture was dissolved at 100° C. to 110° C. The mixture was filtrated at 95° C. to 110° C., the previous container and the residue on the filter were washed with n-butanol (9.8 kg), and the washings were added to the filtrate. The filtrate was cooled to 80° C. to 85° C., and Compound A crystal (24 g) that was prepared according to the method described herein was added thereto, and the mixture was stirred at 80° C. to 85° C. for 2 hours, and then at 70° C. to 75° C. for 1 hour. The mixture was then cooled to 20° C. to 25° C. over 5 hours, and the stirred at 15° C. to 25° C. for 13 hours. The precipitated solid was collected on a filter, and washed with n-butanol (38 kg) and then ethyl acetate (44 kg). The resulting wet solid was dried in vacuo to give Compound A [19] (19.1 kg, 61.5 mol, yield: 91.3%). The given compound was measured about powder X-ray diffraction, infrared spectroscopy, etc. to identify Compound A.

Example 31. Preparation of Compound A (Compound [19])

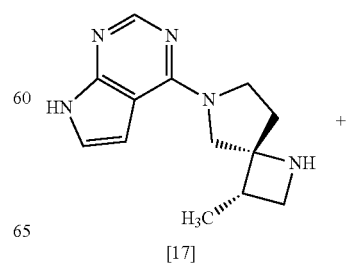

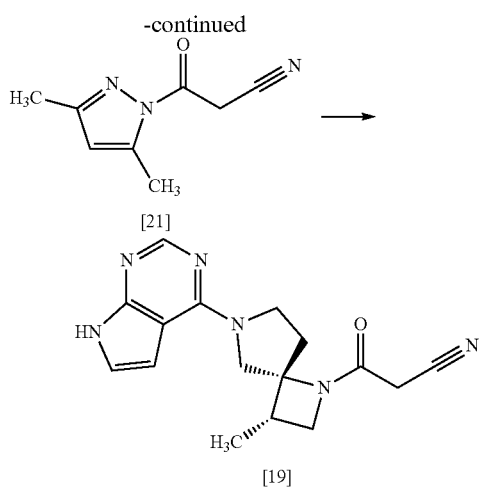

Under nitrogen atmosphere, acetonitrile (900 mL) was added to SR-MDOP [17] (90.0 g, 370 mmol), and then to the mixture was added dropwise a solution of DPCN [21] (63.5 g, 389 mmol) in acetonitrile (540 mL) at 70° C. to 80° C. The dropping funnel used was washed with acetonitrile (90 mL), and the washing was added to the reaction mixture. The reaction mixture was stirred at 70° C. to 80° C. for 1.5 hours, and then to the mixture was added n-butanol (900 mL). The solvent was removed under reduced pressure. n-Butanol (900 mL) was added to the concentrated residue, and the mixture was concentrated again. n-Butanol was added to the concentrated residue so that the total amount of the mixture was adjusted to be 2.1 L, and then the mixture was dissolved with heating at 90° C. to 100° C. The solution was cooled to 60° C. to 70° C., and then thereto was added a crystal of Compound A (90 mg) that was prepared in advance in the same manner as this procedure. The mixture was stirred at 60° C. to 70° C. for 2 hours, and was then cooled to 30° C. over 4 hours. The mixture was stirred at 20° C. to 30° C. for 1 hour, and was then stirred at 0° C. to 5° C. for 4 hours. The precipitated solid was collected on a filter, and the resulted solid was washed with sequentially n-butanol (180 mL) and ethyl acetate (180 mL). The resulted wet solid was dried under reduced pressure to give Compound A [19] (104 g, 335 mmol) in 90.5% yield.

NMR and MS were measured for Compound A that was synthesized in the same manner as this procedure.

$^1$H-NMR (DMSO-$d_6$) δ: 11.60 (s, 1H), 8.09 (s, 1H), 7.12 (dd, 1H, J=3.0, 2.7 Hz), 6.58 (br s, 1H), 4.16 (t, 1H, J=8.4 Hz), 4.11-3.91 (m, 3H), 3.88-3.72 (m, 1H), 3.68 (d, 2H, J=2.1 Hz), 3.57 (dd, 1H, J=8.4, 6.0 Hz), 2.70-2.56 (m, 2H), 2.24-2.10 (m, 1H), 1.12 (d, 3H, J=7.2 Hz).

MS: m/z=311 [M+H]$^+$

Example 32. Purification of Compound a (Compound [19])

Under nitrogen atmosphere, Compound A [19] (100 g, 322 mmol) that was prepared in Example 31 was mixed with n-butanol (1.8 L), and was dissolved therein at 90° C. to 100° C. The solution was filtered at 85° C. to 100° C., and the vessel that had contained the solution and the filtered residue were washed with n-butanol (200 mL). The washing was added to the filtrate. The filtrate was cooled to 60° C. to 70° C., and then thereto was added a crystal of Compound A (100 mg) that was prepared in advance in the same manner as this procedure. This mixture was stirred at 60° C. to 70° C. for 2 hours, and was then cooled to 30° C. over 3 hours. The mixture was stirred at 20° C. to 30° C. for 1 hour, and was then stirred at 0° C. to 5° C. for 4 hours. The precipitated solid was collected on a filter, and the resulted solid was washed with sequentially n-butanol (200 mL) and ethyl acetate (200 mL). The resulted wet solid was dried under reduced pressure to give Compound A [19] (91.7 g, 295 mmol) in 91.7% yield. The resuled compound was analyzed with powder X-ray diffraction, etc. to identify Compound A.

NMR and MS were measured for Compound A that was synthesized in the same manner as this procedure.

$^1$H-NMR (DMSO-$d_6$) δ: 11.60 (s, 1H), 8.09 (s, 1H), 7.12 (dd, 1H, J=2.7, 2.4 Hz), 6.59 (br s, 1H), 4.16 (t, 1H, J=8.2 Hz), 4.11-3.91 (m, 3H), 3.86-3.72 (m, 1H), 3.68 (d, 2H, J=2.1 Hz), 3.58 (dd, 1H, J=8.1, 6.0 Hz), 2.71-2.56 (m, 2H), 2.27-2.09 (m, 1H), 1.12 (d, 3H, J=6.9 Hz).

MS: m/z=311 [M+H]$^+$

INDUSTRIAL APPLICABILITY

The compounds of the present invention are useful as a synthetic intermediate for preparing Compound A. The processes for preparation in the present invention provide a method for stably preparing Compound A in a good chemical and optical purity. The processes for preparation in the present invention may also stably provide Compound A in a good yield, and are useful for an industrially large scale synthesis. The processes for preparation of synthetic intermediates of Compound A in the present invention provide a method for stably preparing RS-ZMAA-DN and SR-MDOZ-OX, the synthetic intermediates of Compound A, in a good chemical and optical purity.

The invention claimed is:

1. A disodium salt dihydrate of a compound of formula [10]

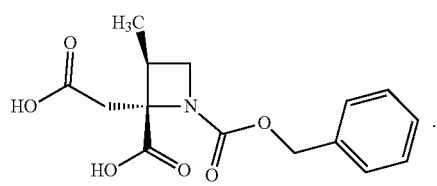

2. A crystal of a disodium salt dihydrate of a compound of formula [10]

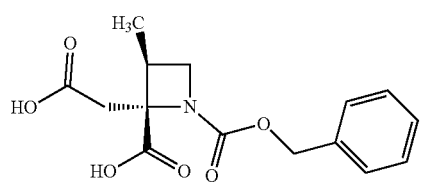

showing a powder X-ray diffraction pattern having peaks at 4.9°±0.2°, 12.3°±0.2°, 15.0°±0.2°, 19.2°±0.2°, Of and 22.7°±0.2° of a diffraction angle (2θ) determined by using CuKα radiation.

3. A process for preparing a disodium salt dihydrate of a compound of formula [10]

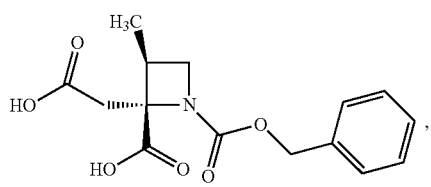

comprising:
reacting a compound of formula [8]

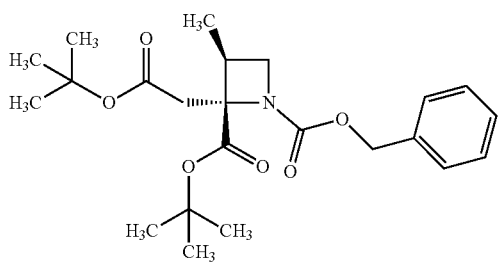

with acid followed by treatment with aqueous sodium hydroxide.

4. The process of claim 3, further comprising the step of reacting a compound of formula [7]

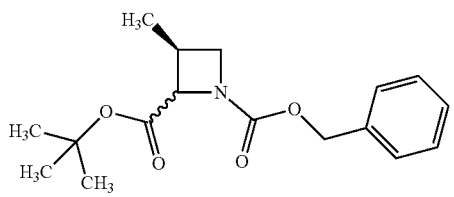

with halogenated acetic acid tert-butyl ester to give the compound of formula [8].

5. The process of claim 4, further comprising the step of reacting a compound of formula [6]

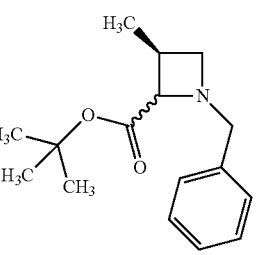

or its salt with halogenated formic acid benzyl ester to give the compound of formula [7].

6. The process of claim 5, further comprising the step of removing a protecting group from a compound of formula [4]

or its salt to give a compound of formula [6] or its salt.

* * * * *

UNITED STATES PATENT AND TRADEMARK OFFICE
CERTIFICATE OF CORRECTION

Page 1 of 1

PATENT NO. : 10,822,354 B2
APPLICATION NO. : 15/741926
DATED : November 3, 2020
INVENTOR(S) : Takahiro Yamasaki et al.

It is certified that error appears in the above-identified patent and that said Letters Patent is hereby corrected as shown below:

In the Claims

<u>Column 74</u>
Claim 2, Line 63, before "and" delete "Of".

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*